United States Patent
Semprini et al.

(10) Patent No.: US 11,845,927 B2
(45) Date of Patent: Dec. 19, 2023

(54) BIOREMEDIATION USING CO-METABOLISM SUBSTRATES

(71) Applicants: Oregon State University, Corvallis, OR (US); North Carolina State University, Raleigh, NC (US)

(72) Inventors: Lewis Semprini, Corvallis, OR (US); Mitchell Rasmussen, Corvallis, OR (US); Michael R. Hyman, Raleigh, NC (US)

(73) Assignees: Oregon State University, Corvallis, OR (US); North Carolina State University, Raleigh, NC (US)

( * ) Notice: Subject to any disclaimer, the term of this patent is extended or adjusted under 35 U.S.C. 154(b) by 260 days.

(21) Appl. No.: 16/689,978

(22) Filed: Nov. 20, 2019

(65) Prior Publication Data

US 2020/0157523 A1    May 21, 2020

Related U.S. Application Data

(60) Provisional application No. 62/770,554, filed on Nov. 21, 2018.

(51) Int. Cl.
   *C12N 11/10* (2006.01)
   *C12N 9/02* (2006.01)
   (Continued)

(52) U.S. Cl.
   CPC .............. *C12N 11/10* (2013.01); *C07F 7/025* (2013.01); *C12N 1/14* (2013.01); *C12N 1/20* (2013.01); *C12N 9/0071* (2013.01)

(58) Field of Classification Search
   None
   See application file for complete search history.

(56) References Cited

U.S. PATENT DOCUMENTS 6,472,198 B1    10/2002   Semprini et al.
6,905,288 B2    6/2005    Miyazaki
(Continued)

FOREIGN PATENT DOCUMENTS

CN    100427594 C    * 10/2008
CN    105087540 A    * 11/2015

OTHER PUBLICATIONS

Russell, H. et al. 1992. Ground Water Issue: TCE removal from Contaminated Soil and Ground Water. Environmental Protection Agency publication. p. 1-10 (Year: 1992).*

(Continued)

*Primary Examiner* — Allison M Fox
*Assistant Examiner* — Qing Xu
(74) *Attorney, Agent, or Firm* — Klarquist Sparkman, LLP

(57) ABSTRACT

Certain disclosed embodiments concern a bioremediation composition comprising microbial cells, at least one co-metabolism substrate to induce selected enzyme production by the microbial cells, and a bead or gel encapsulating the microbial cells, such as bacterial or fungi cells, and the at least one co-metabolism substrate. For certain embodiments, the substrate is a slow release compound, such as an orthosilicate that hydrolyzes to produce an alcohol growth substrate. Embodiments of a method for using the composition to transform contaminants of concern also are disclosed.

2 Claims, 40 Drawing Sheets
(40 of 40 Drawing Sheet(s) Filed in Color)

(51) Int. Cl.
*C07F 7/02* (2006.01)
*C12N 1/14* (2006.01)
*C12N 1/20* (2006.01)

(56) References Cited

U.S. PATENT DOCUMENTS

| | | |
|---|---|---|
| 8,241,500 B2 | 8/2012 | Saul |
| 2003/0113903 A1 | 6/2003 | Miyazaki |
| 2014/0051144 A1* | 2/2014 | Wackett .................. C12N 11/04 435/176 |
| 2015/0125901 A1 | 5/2015 | Razavi-Shirazi et al. |

OTHER PUBLICATIONS

Moslemy et al. Bioprocess Biosyst. Engineer. (2004) 26: 197-204 (Year: 2004).*
Machine translation for Li et al. (CN 106011124) published 2016, downloaded from the EPO website Sep. 29, 2021 (Year: 2016).*
Mosmeri et al. J. Tiawan Institute of Chem. Engineers (20017) 78: 299-306 (Year: 2017).*
Rolston et al. AGU Fall Meeting Abstracts (2016) page H23C1556R (Year: 2016).*
Kuntz et al. J. Ind. Microbial. Biotechnol. (2002) 30: 651-655 (Year: 2002).*
Emblem et al. J. Appl. Chem. Biotechnol. (1971) 21: 317-318 (Year: 1971).*
Vancheeswaran et al. Environ. Sci. Technol. (1999) 33: 1077-1085 (Year: 1999).*
Semprini et al. (urrent Opinions Biotechnol. (1997) 8: 296-307 (Year: 1997).*
Moslemy et al. from "Methods in Biotechnology: Immobilization of Enzymes and Cells" (2006), pp. 415-426 (Year: 2006).*
Moslemy et al. (Enzyme Microb. Technol. (2002) 30: 10-18 (Year: 2002).*
Razavi-Shirazi et al. (Water Environmental Res. (2000) 72(4): 460-468 (Year: 2000).*
Machine translation of Gao et al. (CN 100427594C, published Oct. 22, 2008, downloaded from the EPO on Aug. 17, 2022 (Year: 2008).*

* cited by examiner

BIOREMEDIATION USING CO-METABOLISM SUBSTRATES

CROSS REFERENCE TO RELATED APPLICATIONS

This application claims the benefit under 35 U.S.C. § 119(e) of the Nov. 21, 2018 earlier filing date of U.S. provisional patent application No. 62/770,554. U.S. provisional patent application No. 62/770,554 is incorporated herein by reference in its entirety.

ACKNOWLEDGMENT OF GOVERNMENT SUPPORT

This invention was made with government support under Grant No. W912HQ17C0048 awarded by United States Department of Defense—SERDP. The government has certain rights in the invention.

FIELD

This application concerns transformation of contaminants using selected microorganisms and slow release substrates co-encapsulated in a bead or gel to promote contaminant transformation.

BACKGROUND

Mixtures of contaminates of concern (COCs) are present in ground water at many Department of Defense (DoD) sites as well as industrial facilities. A recent review indicated that 59% of DoD sites have more than one contaminant present, often in commingled plumes. Most frequently observed COCs include chlorinated and non-chlorinated VOCs. PCBs, metals, inorganics, perchlorate, PFCs, NDMA, and munitions. 1,4-Dioxane (14D) also is often present in mixtures of chlorinated aliphatic hydrocarbons (CAHs), due to its use as a stabilizer in commercial solvent formulations. In a multisite survey of 2000 sites in California, 14D was detected at 194 sites with 95% of these containing one or more chlorinated solvents. In 76% of these sites both 14D and 1,1,1-trichlorethance (1,1,1-TCA) were present, and in 59 sites 14D was present with 1,1,1-TCA, trichloroethene (TCE), and 1,1-diochloroethen (11DCE). While 1,1,1-TCA is thought to be the likely source of most 14D plumes, 64% of 14D detections at USAF installations were associated with only TCE. Thus, an effective contaminant removal process must be able to treat mixtures of contaminates, including mixtures of TCE and 14D. Adamson et al. found that in 62% of the plumes studied, the CAH plume was longer than the 14D plume. Thus, zones where 14D and CAHs co-occur and where in-situ treatment may be applied are common.

This environmental problem is not limited to DOD sites and instead is a nation-wide problem. A USGS survey of 1255 domestic drinking water wells and 242 public supply wells in the United States that found 14 compounds (seven VOCs, six pesticides, and nitrate) represented 95% of the detected contaminant mixtures. The seven VOCs and their rank order of detection were: CF, (4), PCE (5); 11ITCA (8); MTBE (10): TCE (11I); 11DCA (12) and 11DCE (13).

Environmental remediation of these compounds typically requires specialized microorganisms with unusual metabolic capabilities. High concentrations of individual COCs are also usually needed to supply sufficient carbon and energy to support growth of these microorganisms.

In situ bioremediation via aerobic co-metabolism could potentially provide a large cost savings for treatment of COC in mixtures, especially for mixtures that include 1,4D. Accordingly, new compositions and methods for in situ via aerobic co-metabolism are needed.

SUMMARY

The present invention concerns embodiments of a composition and method for transformation of contaminants, such as in situ co-metabolic bioremediation of contaminants of concern.

Certain embodiments of the present invention concern a composition comprising microbial cells, at least one co-metabolism substrate to induce selected enzyme production by the microbial cells, and a bead or gel encapsulating the microbial cells and the at least one co-metabolism substrate. Exemplary enzymes include monooxygenases, short chain alkane monooxygenases (SCAM), dioxygenases, toluene oxygenases, or combinations thereof. This first composition can be used to contact a contaminant, such as a contaminant of concern, which then may form a second composition comprising the contaminant. The co-metabolism substrate may be a gas, an alcohol, a slow release compound, or combinations thereof.

For particular embodiments, the co-metabolism substrate is a slow release compound suitable to produce a growth substrate. Exemplary slow release compounds include slow release orthosilicates; organic esters that hydrolyze to form an organic acid and an alcohol; oils that ferment and hydrolyze to form organic acids; polymers that hydrolyze to form lactate or lactate-like substrates; oils that slowly dissolve into solution, but can be directly utilized by bacteria; and combinations thereof. Certain embodiments used orthosilicates that hydrolyze to produce an alcohol or carboxylic acid growth substrate having Formula 1

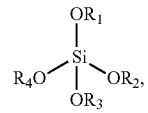

Formula 1 wherein $R_1$-$R_4$ are independently selected from aliphatic and aryl substituents, such as propyl, butyl and phenyl substituents. Exemplary orthosilicates used for certain disclosed embodiments include tetrabutyl orthosilicate (TBOS), tetra-sec-butyl orthosilicate (T2BOS), tetraisopropoxysilane (T2POS), tetraphenyl-orthosilicate, and combinations thereof.

Slow release compounds hydrolyze at different rates. Accordingly, slow release compounds can be selected to hydrolyze to provide a growth substrate at a particular rate. For example, a slow release compound can be selected to hydrolyze at a rate suitable for long term contaminant transformation, such as for periods of days, months or years.

The composition can include slow release compound co-encapsulated with the microbial cells at various amounts suitable for particular applications. For example, compositions can include a slow release compound, or compounds, co-encapsulated with the microbial cells at a high mass loading of 10% (w/w) or greater.

For certain compositions the microbial cells are bacterium or combinations of bacteria, including *Rhodococus jostii* RHA1, *Mycobacterium vaccae* (austroafricanum) JOB5

(ATCC 29678), *Rhodococcus rhodochrous* (ATCC 21198), *Rhodococcus rhodochrous* (ATCC 21197), *Brevibacterium butanicum* (ATCC 21196), *Brevibacterium parafinoliticum* (ATCC 21195), *Rhodococcus ruber* ENV425, *Sphingopyxis* sp. AX-A, *Pseudonocardia dioxanivorans* CB1190, *Mycobacterium* sp. PH-06, *Acinetobacter baumannii* DD1, *Mycobacterium austroafricanum* IFP2016, *Pseudonocardia* sp, strain ENV478, *Rhodococcus* sp. RR1 N/A, *Flavobacterium* N/A, *Pseudonocardia tetrahydrofuranoxidans* K1, *Burkholderia vietnamiensis* G4, *Ralstonia pickettii* PKO1, *Pseudomonas mendocina* KR1, *Pseudomonas putida* F1, *Pseudomonas putida* mt2, *Aureobasidium pullmans* NRRL 21064, *Graphium* sp. (ATCC 58400) (fungus), *Xanthobacter autotrophicus* Py2, *Rhodococcus rhodochrous* B-276, *Nitrosomonas europaea, Ralstonia eutrophus* JMP 134, *Thauera butanivorans, Methylosinus trichosporium* OB3b, *Methylomonas methanica* 68-1, *Methylococcus capsulatus* (Bath), *Pseudomonas stutzeri* OX1, *Pseudomonas* sp. DCA1, *Rhodococcus erythropolis. Alcaligenes denitrificans. Pseudomonas* sp. PS14, *Pseudomonas putida* GPo1, *Arthrobacter* sp. (ATCC 27779), *Corynebacterium alkanum* (ATCC 21194), *B. butanicum* (ATCC 21196). *Arthrobacter* sp. (ATCC 27779), *Mycobacterium vaccae* JOB5 (ATCC 29678*) *R. wratislaviensis* PD630 (DSM 44193*), *Sphingomonas* sp. PH-07, *Sphingomonas* sp, strain PheB4, and *Sphingopyxis* KCY 1, or combinations thereof. Particular working examples used *Rhodococcus rhodochrous* ATCC 21198 and *Burholderia vietnamiensis* strain G4 to exemplify this aspect of the invention. In other embodiments, the microbial cells are fungi, such as *Graphium* sp. (ATCC 58400) (fungus), *Armillaria* sp. F022 (white-rot fungus), and *Pycnoporus sanguineus*, or combinations thereof.

The microbial cells and least one co-metabolism substrate are encapsulated in a bead or gel. Any suitable material useful for forming beads or gels can be used, including a polysaccharide, alginate, gellan gum, chitosan, carrageenan, polyvinyl alcohol (PVA) and cellulose triacetate. Beads may be formed from these materials to have any desired shape and size, as exemplified by substantially spherical, cylindrical, square, rectangular or oblate beads, and including both macro beads having at least one dimension of 1 millimeter or greater and micro beads having at least one dimension of 100 μm or less.

The contaminant can be any contaminant, particularly contaminants of concern selected from 1,4-dioxane (1,4-dialkoxybenzenes), 1,3-dioxane (1,3-dialkoxybenzenes), tetrahydrofuran, 1,3-dioxalone, and tetrahydropyran; chlorinated ethenes, such as trichloroethene (TCE), 1,2-cis-dichlorethene (cis-DCE), 1,1-dichloroethene (1,1-DCE), 1,2-trans-dichloroethene (trans-DCE), and vinyl chloride (chloroethene) (VC); halogenated alkanes, such as, 1,2,2-tetrachloroethane, 1,1,1-trichloroethane (1,1,1-TCA), 1,1,2-trichloroethene (1,1,2-TCA), 1,1-dichloroethane (1,1-DCA), 1,2-dichloroethane (1,2-DCA), 1,1,1,2-tetrachloroethane, chloroethane, bromoethane, 1,2,3-trichloropropane (TCP), 1,2-dichloropropane, chloroform (trichloromethane), dichloromethane(methylene chloride), chloromethane, bromomethane, dichlorofluoromethane, freons, and difluoromethane (refrigerant); disinfection byproducts, such as N-nitrosodimethylamine (NDMA), chloroform, bromoform, bromodichloromethane, and chlorodibromomethane; halogenated aromatics, such as 1,2-dichlorobenzene, 1,4-dichlorobenzene, chlorophenol, 4-chlorophenol, dichlorophenol, 1,3-dichlorophenol, 2,5-dichlorophenol, pentachlorophenol, and 1,2,4,5-tetrachlorobenzene; perflourinated compounds, such as perfluoropentanoate (PFPeA), perfluorohexanoate (PFHxA), perfluoroheptanoate (PFHpA), perfluorooctanoate (PFOA), perfluorononanoate (PFNA), perfluorodecanoate (PFDA), perfluoroundecanoate (PFUnDA), perfluorohexanesulfonate (PFHxS), and per-fluorooctanesulfonate (PFOS); explosives, including nitroaromatics, such as trinitrotoluene, 2,4,6-trinitrotoluene, cyclotrimethylenetrinitramine (RDX), and nitrobenzene; pesticides, such as bentazone; ethers, such as methyl tertiary butyl ether (MTBE), ethyl tertiary butyl ether (ETBE), tertiary amyl methyl ether (TAME), diisopropyl ether (DIPE), tertiary butyl alcohol (TBA), dimethyl ether (DME), bis(2-chloroethyl)ether (BCEE), and bis(2-chloroisopropyl)ether (BCIP); nitrosamines, such as N-nitrosomorpholine and N-nitrosodimethylamine (NDMA); phthalates, such as di-2-ethylhexyl phthalate, bisphenol A, tetrabromobisphenol A (TBBPA) and 4,4'-diaminostilbene-2,2'-disulfonic acid (DSDA); antibiotics, such as sulfamethoxazole (SMX), pharmaceutically active compounds (PHACs), triclosan, bisphenol, ibuprofen, atenolol, naproxen, ketoprofen, diclofenac, clofibric acid, bezafibrate; natural and synthetic estrogens, such as 17β-estradiol (E2), α-estriol (E3), and 17α-ethinylestradiol (EE2); nonylphenols, such as 4-nonylphenols, 2-nonylphenols, decylphenol, and brominated octylphenoxyacetic acid; polycyclic aromatic hydrocarbons, such as naphthalene, fluorene, phenanthrene, anthracene, fluoranthene, pyrene, benzo[a]pyrene (BaP), benz[a]anthracene, and dibenz[a,h]anthracene; and any and all combinations of these contaminants.

Compositions according to the present invention can also include at least one additional remediation material. For example, such compositions can include activated carbon.

Compositions according to the present invention can be used to make contaminant remediation devices. One example of such a device is a flow-through column packed with an effective composition, such as beads comprising a suitable composition or compositions.

Embodiments of a method for using the compositions and devices also are disclosed. One embodiment comprises using a disclosed composition or device to transform a contaminant in a material, such as a gas, fluid and/or solid material. Exemplary materials include soils, sediments, aquifer materials, rock, gravel, sand, silt, ice, glaciers, snowfields, air, oxygen, industrial gases, helium, hydrogen, nitrogen, volatile organic compounds, drinking water, water intended for household uses, wastewater, wells, groundwater, ponds, rivers, lakes, oceans, organic liquids, and any and all combinations of such materials.

A particular disclosed embodiment comprises providing a composition comprising bacterial cells selected from *Rhodococcus rhodochrous* ATCC 21198. *Burholderia vietnamiensis* strain G4, or combinations thereof, at least one orthosilicate slow release compound that hydrolyzes to produce an alcohol and/or carboxylic acid growth substrate that induces selected oxygenase enzyme production by the bacterial cells, and an alginate and/or gellan gum macro- or micro-bead encapsulating the bacterial cells and the at least one orthosilicate slow release compound. A material comprising a contaminant is contacted with the composition.

The foregoing and other objects, features, and advantages of the invention will become more apparent from the following detailed description, which proceeds with reference to the accompanying figures.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

I. Definitions and Abbreviations

Figure 1:
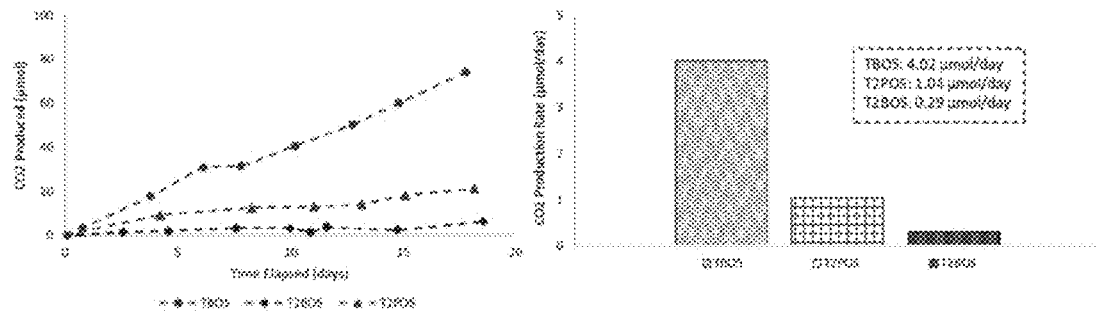
FIG. 1 is a graph illustrating production of $CO_2$ produced versus time to compare the release of alcohols from orthosilicate slow release compounds and the microbial utilization of the alcohols.

The following explanations of terms and abbreviations are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

The disclosure of numerical ranges should be understood as referring to each discrete point within the range, inclusive of endpoints, unless otherwise noted. Unless otherwise indicated, all numbers expressing quantities of components, molecular weights, percentages, temperatures, times, and so forth, as used in the specification or claims are to be understood as being modified by the term "about." Accordingly, unless otherwise implicitly or explicitly indicated, or unless the context is properly understood by a person of ordinary skill in the art to have a more definitive construction, the numerical parameters set forth are approximations that may depend on the desired properties sought and/or limits of detection under standard test conditions/methods as known to those of ordinary skill in the art. When directly and explicitly distinguishing embodiments from discussed prior art, the embodiment numbers are not approximates unless the word "about" is recited.

Although there are alternatives for various components, parameters, operating conditions, etc. set forth herein, that does not mean that those alternatives are necessarily equivalent and/or perform equally well. Nor does it mean that the alternatives are listed in a preferred order unless stated otherwise.

Definitions of common terms in chemistry may be found in Richard J. Lewis, Sr. (ed.), *Hawley's Condensed Chemical Dictionary*, published by John Wiley & Sons, Inc., 2016 (ISBN 978-1-118-13515-0). Definitions of common terms in molecular biology may be found in Benjamin Lewin, *Genes VII*, published by Oxford University Press, 2000 (ISBN 019879276X); Kendrew et al. (eds.), *The Encyclopedia of Molecular Biology*, published by Blackwell Publishers, 1994 (ISBN 0632021829); and Robert A. Meyers (ed.), *Molecular Biology and Biotechnology: a Comprehensive*

*Desk Reference*, published by Wiley, John & Sons, Inc., 1995 (ISBN 0471186341); and other similar references.

In order to facilitate review of the various embodiments of the disclosure, the following explanations of specific terms are provided:

Alcohol: An organic compound including at least one hydroxyl group. Alcohols may be monohydric (including one —OH group), dihydric (including two —OH groups; diols, such as glycols), trihydric (including three —OH; triols, such as glycerol) groups, or polyhydric (including three or more —OH groups; polyols). The organic portion of the alcohol may be aliphatic, cycloaliphatic (alicyclic), heteroaliphatic, cycloheteroaliphatic (heterocyclic), polycyclic, aryl, or heteroaryl, and may be substituted or unsubstituted.

Aliphatic: A substantially hydrocarbon-based group or moiety. An aliphatic group or moiety can be acyclic, including alkyl, alkenyl, or alkynyl groups, cyclic versions thereof, such as cycloaliphatic groups or moieties including cycloalkyl, cycloalkenyl or cycloalkynyl, and further including straight- and branched-chain arrangements, and all stereo and position isomers as well. Unless expressly stated otherwise, an aliphatic group contains from one to twenty-five carbon atoms ($C_{1-25}$); for example, from one to fifteen ($C_{1-15}$), from one to ten ($C_{1-10}$) from one to six ($C_{1-6}$), or from one to four carbon atoms ($C_{1-4}$) for an acyclic aliphatic group or moiety, or from three to fifteen ($C_{3-15}$) from three to ten ($C_{3-10}$), from three to six ($C_{3-6}$), or from three to four ($C_{3-4}$) carbon atoms for a cycloaliphatic group or moiety. An aliphatic group may be substituted or unsubstituted, unless expressly referred to as an "unsubstituted aliphatic" or a "substituted aliphatic." An aliphatic group can be substituted with one or more substituents (up to two substituents for each methylene carbon in an aliphatic chain, or up to one substituent for each carbon of a —C=C— double bond in an aliphatic chain, or up to one substituent for a carbon of a terminal methine group).

Lower aliphatic: An aliphatic group containing from one to ten carbon atoms ($C_{1-10}$), such as from one to six ($C_{1-6}$), or from one to four ($C_{1-4}$) carbon atoms; or from three to ten ($C_{3-10}$), such as from three to six ($C_{3-6}$) carbon atoms for a lower cycloaliphatic group.

Alkoxy: Refers to the group —OR, where R is a substituted or unsubstituted alkyl or a substituted or unsubstituted cycloalkyl group. In certain examples R is a $C_{1-6}$ alkyl group or a $C_{3-6}$ cycloalkyl group. Methoxy (—OCH$_3$) and ethoxy (—OCH$_2$CH$_3$) are exemplary alkoxy groups. In a substituted alkoxy, R is substituted alkyl or substituted cycloalkyl, examples of which include haloalkoxy groups, such as —OCF$_2$H, or —OCF$_3$.

Alkyl: Refers to a saturated aliphatic hydrocarbyl group having from 1 to 25 ($C_{1-25}$) or more carbon atoms, more typically 1 to 10 ($C_{1-10}$) carbon atoms such as 1 to 6 ($C_{1-6}$) carbon atoms or 1 to 4 ($C_{1-4}$) carbon atoms. An alkyl moiety may be branched, substituted or unsubstituted. This term includes, by way of example, linear and branched hydrocarbyl groups such as methyl (CH$_3$), ethyl (—CH$_2$CH$_3$), n-propyl (—CH$_2$CH$_2$CH$_3$), isopropyl (—CH(CH$_3$)$_2$), n-butyl (—CH$_2$—CH$_2$CH$_2$CH$_3$), isobutyl (—CH$_2$CH(CH$_3$)$_2$), sec-butyl (—CH(CH$_3$)(CH$_2$CH$_3$), t-butyl (—C(CH$_3$)$_3$), n-pentyl (—CH$_2$CH$_2$CH$_2$CH$_2$CH$_3$), and neopentyl (—CH$_2$C(CH$_3$)$_3$).

Aromatic or aryl: An unsaturated, cyclic hydrocarbons having alternate single and double bonds. Benzene, a 6-carbon ring containing three double bonds, is a typical aromatic compound.

Aryl: A monovalent aromatic carbocyclic group of, unless specified otherwise, from 6 to 15 carbon atoms having a single ring (e.g., phenyl) or multiple condensed rings in which at least one ring is aromatic (e.g., quinoline, indole, benzodioxole, and the like), provided that the point of attachment is through an atom of an aromatic portion of the aryl group and the aromatic portion at the point of attachment contains only carbons in the aromatic ring. If any aromatic ring portion contains a heteroatom, the group is a heteroaryl and not an aryl. Aryl groups are monocyclic, bicyclic, tricyclic or tetracyclic.

Bacteria: Single-cell, prokaryotic (i.e., without a nucleus) organisms.

Co-metabolism: Growth and activity of a microorganism is promoted by addition of an exogenous primary growth-supporting substrate and target contaminants of concern are then degraded by enzymes expressed to enable microbial growth on the primary substrate.

Contacting: Placement that allows association between two or more moieties, particularly direct physical association, for example both in solid form and/or in liquid form (for example, the placement of a biological sample, such as a biological sample affixed to a slide, in contact with a composition, such as a solution containing the compositions disclosed herein).

Control: A sample or procedure performed to assess test validity. In one example, a control is a quality control, such as a positive control. For example, a positive control is a procedure or sample, such as a tissue or cell, that is similar to the actual test sample, but which is known from previous experience to give a positive result. A positive control confirms that the basic conditions of the test produce a positive result, even if none of the actual test samples produce such result. In a particular example, a positive control is a sample known by previous testing to contain the suspected antigen.

In other examples, a control is a negative control. A negative control is a procedure or test sample known from previous experience to give a negative result. The negative control demonstrates the base-line result obtained when a test does not produce a measurable positive result; often the value of the negative control is treated as a "background" value to be subtracted from the test sample results. In a particular example, a negative control is a reagent that does not include the specific primary antibody. Other examples include calibrator controls, which are samples that contain a known amount of a control antigen. Such calibrator controls have an expected signal intensity, and therefore can be used to correct for inter- or intra-run staining variability.

Enzyme: A protein molecule that is capable of catalyzing a chemical reaction. For example, monooxygenase is an enzyme that incorporates one hydroxyl group into substrates.

Ester: A chemical compound derived from an organic acid (general formula: RCO$_2$H) where the hydrogen of the —OH (hydroxyl) group is replaced by an aliphatic, alkyl or aryl group. A general formula for an ester derived from an organic acid is shown below:

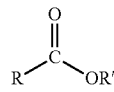

where R and R' denote virtually any group, including aliphatic, substituted aliphatic, aryl, arylalkyl, heteroaryl, etc.

Ether: A class of organic compounds containing an ether group, that is an oxygen atom connected to two aliphatic and/or aryl groups, and having a general formula R—O—R', where R and R' may be the same or different.

Functional group: A specific group of atoms within a molecule that is responsible for the characteristic chemical reactions of the molecule. Exemplary functional groups include, without limitation, alkyl, alkenyl, alkynyl, aryl, halo (fluoro, chloro, bromo, iodo), epoxide, hydroxyl, carbonyl (ketone), aldehyde, carbonate ester, carboxylate, carboxyl, ether, ester, peroxy, hydroperoxy, carboxamide, amino (primary, secondary, tertiary), ammonium, imide, azide, cyanate, isocyanate, thiocyanate, nitrate, nitrite, nitrile, nitroalkyl, nitroso, pyridyl, phosphate, sulfonyl, sulfide, thiol (sulfhydryl), disulfide.

Fungi: A diverse group of eukaryotic single-celled or multinucleate organisms and includes any of about 144,000 known species of organisms of the kingdom Fungi, such as yeasts, rusts, smuts, mildews, molds, and mushrooms.

Gel: A colloidal system comprising a solid three-dimensional network within a liquid. By weight, a gel is primarily liquid, but behaves like a solid due to a three-dimensional network of entangled and/or crosslinked molecules of a solid within the liquid.

Gelling agent: A substance that stabilizes and/or thickens a liquid or sol (colloidal suspension) to provide a gel. A thermogelling agent is a substance that forms a three-dimensional network within a liquid when subjected to a temperature change. Some thermogelling agents form a gel when heated above a certain temperature; other thermogelling agents form a gel when the temperature is decreased below a certain threshold.

Gelling aid: A substance (e.g., a compound or ion) that facilitates, or is required for, gelation of a gelling agent. For example, certain cations, such as $Ba^{2+}$ and $Ca^{2+}$ facilitate gelation of gellan gum.

Halo, halide or halogen: Refers to fluoro, chloro, bromo or iodo.

Haloalkyl: An alkyl moiety substituted with one or more halogens. Exemplary haloalkyl moieties include —$CH_2F$, —$CHF_2$ and —$CF_3$.

Hydroxyl: Refers to the group —OH.

Hydrogel: A cross-linked three-dimensional network of polymeric chains that are capable of absorbing and retaining molecules (e.g., water, polar solvents, non-polar solvents, drugs in liquid form, or the like) in their three-dimensional networks. Hydrogel-forming polymeric chains comprise one or more hydrophilic functional groups in their polymeric structures, such as amino ($NH_2$), hydroxyl (OH), amide (—CONH—, —$CONH_2$), sulfate (—$SO_3H$), or any combination thereof, and can be natural-, or synthetic-polymeric-based networks. In some embodiments, the polymeric chains can comprise a plurality of the same monomeric units. In other embodiments, the polymeric chains can comprise a plurality of different monomeric units. Exemplary hydrogels may include, but are not limited to, proteins (e.g., collagen, gelatin, or the like), denatured proteins (e.g., methacrylated gelatin [GelMA], methacrylated collagen [Col-MA], or the like), polysaccharide (chitosan, starch, alginate, or the like), synthetic hydrogels (e.g., poly(ethylene glycol) diacrylate [PEGDA]).

Lower: Refers to organic compounds having 10 or fewer carbon atoms in a chain, including all branched and stereochemical variations, particularly including methyl, ethyl, propyl, butyl, pentyl, hexyl, heptyl, octyl, nonyl, and decyl.

Molecular weight: The sum of the atomic weights of the atoms in a molecule. As used herein with respect to polymers, the terms molecular weight, average molecular weight, and mean molecular weight refer to the number-average molecular weight, which corresponds to the arithmetic mean of the molecular weights of individual macromolecules. The number-average molecular weight may be determined by any method generally known by persons of ordinary skill in the art, such as chromatographic methods.

Silyl ester: A functional group with the formula:

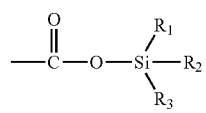

where $R_1$-$R_3$ independently are selected from various groups, including by way of example aliphatic, substituted aliphatic, cyclic aliphatic, substituted cyclic aliphatic, aryl, substituted aryl, heteroaryl, and substituted heteroaryl.

Silyl ether: A functional group with the formula:

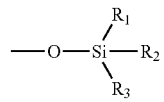

where $R_1$-$R_3$ independently are selected from various groups, including by way of example aliphatic, substituted aliphatic, cyclic aliphatic, substituted cyclic aliphatic, aryl, substituted aryl, heteroaryl, and substituted heteroaryl.

Soluble: Capable of becoming molecularly or ionically dispersed in a solvent to form a homogeneous solution. U.S. Pharmacopeia definitions: very soluble: more than 1000 mg/ml, freely soluble: 100-1000 mg/ml, soluble: 30-100 mg/ml, sparingly soluble: 10-30 mg/ml, slightly soluble: 1-10 mg/ml, very slightly soluble: 0.1-1 mg/ml, practically insoluble or insoluble: <0.1 mg/ml.

Solution: A homogeneous mixture composed of two or more substances. A solute (minor component) is dissolved in a solvent (major component). A plurality of solutes and/or a plurality of solvents may be present in the solution.

Substrate: A molecule acted upon by a catalyst, such as an enzyme.

The following abbreviations may be used to described certain embodiments of the present invention.

1,1,1-TCA 1,1,1-Trichloroethane
cis-DCE cis-Dichloroethene
1,4-D 1,4-Dioxane
21198 *Rhodococcus rhodochrous* ATC®
AB1 21198™
AB2 Active Bottle 1
ABL Active Bottle 2
Ace Activity Based Labeling
ATCC Acetylene
CAS No. American Type Culture Collection
COC Chemical Abstracts Service Number
DI Contaminants of Concern
DoD Deionized Water
ECD Department of Defense
EPA Electron Capture Detector
FID Environmental Protection Agency GC Flame Ionization Detector
GG Gas Chromatograph
IB Gellan Gum
$K_{ow}$ Isobutane
LNAPL Octanol-Water Partition Coefficient
MCL Light Non-Aqueous Phase Liquid
MS Maximum Contaminant Level
MSM Mass Spectrometer
NCSU Minimal Salts Media
NPL North Carolina State University
OD600 National Priorities List
P Optical Density at 600 nm
ppm Poisoned
sBA parts per million
SCAM sec-Butyl Acetate
SG Short-Chain Alkane Monooxygenase
SRCs Specific Gravity
SVE Slow-Release Compounds
T2BOS Soil Vapor Extraction
T2POS Tetra-s-butyl orthosilicate
TBOS Tetraisopropoxysilane
TCE Tetrabutyl orthosilicate
THF Trichloroethene
TKEBS Tetrahydrofuran
TSGA Tetrakis(2-ethylbutoxy)silane
TSS Tryptic Soy Growth Agar
VC Total Suspended Solids
Vinyl Chloride

II. Introduction

Compositions, and methods for making and using disclosed compositions, are disclosed, where the compositions comprise co-encapsulated substrates, particularly slow release compounds (SRC), with viable microbial cells. The compositions may be encapsulated in, for example, alginate and gellan gum hydrogel beads. These compositions are useful for in-situ, aerobic co-metabolic treatment of contaminants of concern (CoCs) in soil and water, such as contaminated wells and groundwater. CoCs include, but are not limited to, 1,4-dioxane and halogenated, e.g. chlorinated aliphatic hydrocarbons.

Any suitable microbial cells can that are useful for the disclosed purpose may be used to practice the disclosed embodiments. For certain embodiments. *Rhodococcus rhodochrous* ATCC 21198 (ATCC 21198) was used to co-metabolically transform mixtures of CoCs when grown on isobutane as the primary substrate. In addition to isobutane inducing co-metabolic transformation, research conducted concurrently to this project has shown that the growth of ATCC 21198 on non-gaseous substrates, like aliphatic alcohols, typically lower alkyl alcohols, such as 2-butanol, stimulate production of suitable bioremediation enzymes, such as the short chain alkane monooxygenase (SCAM) enzyme of ATCC 21198 that may be responsible for the co-metabolic transformation of CoCs as disclosed herein. The present application also discloses using slow release compounds, such as, for example, without limitation, tetrabutylorthosilicate (TBOS) and tetrasec-butylorthosilicate ($T_2BOS$), which hydrolyze slowly at ester bonds to produce 1- and 2-butanol, respectively, which may exist in pure phase as light non-aqueous phase liquids (LNAPL).

Certain disclosed embodiments concern LNAPL SRCs (e.g. TBOS and $T_2BOS$) co-encapsulated in alginate or gellan gum matrices at high mass loadings, such as mass loadings of greater than >10% (w/w), and co-encapsulated with microbial cells that facilitate COC transformation, such as, for example, ATCC 21198. These co-encapsulated formulations consume SRC products (e.g. 1- and 2-butanol) prior to diffusion from beads. The energy gained from using 1- and 2-butanol by encapsulated cultures increased the survivability, overall activity, and contaminant transformation rate and capacity of initially augmented biomass. For example, in batch systems cells co-encapsulated with SRCs can maintain co-metabolic transformation potential for over 70 days. Conversely similar cellular biomass suspended in media lost the majority of CoC transformation potential after the first 12 days. Also, co-encapsulated cultures were able to transform 2-4 times more contaminants than suspended cultures over the 70-day period, and transformation within co-encapsulated systems was continuing.

The co-encapsulated SRCs produce an exclusive controlled source of an inducing growth substrate that supports the co-encapsulated microbial populations, extend the remediation duration, and increase the transformation capacity of initially augmented cultures. In addition to supporting a targeted microbial species, the inclusion of an SRC mitigated issues with current bioaugmentation methods that result in excess cellular growth, oxygen depletion, and the need for recurring low concentration injections of gaseous substrates.

Thus, SRCs can be combined with specific microorganisms, such as microorganisms whose monooxygenase or dioxygenase enzymes are induced by substrates that are produced in situ, such as by hydrolysis reactions. The rate of release of the substrate can be modified based on the structure of the SRC. For example, for the TBOS and $T_2BOS$ SRC, TBOS is hydrolyzed at faster rates than $T_2BOS$. Thus, the rate of release can be selected and modified as desired for a specific application and a specific mixture of contaminants.

Formulation in beads also permits mixing different substrates and microorganisms together to develop mixed beaded systems to transform a broad range of contaminants. For example, one disclosed embodiment expresses short chain monooxygenase enzymes that transformed 1,4-dioxane, 1,1,1-trichloroethene and 1,1-dichloroethene using *Rhodococcus rhodochrous* 21198. Another disclosed embodiment concerns using toluene monooxygenase from *Burholderia vietnamiensis* strain G4 to transform trichloroethene (TCE), 1,1-dichloroethene, cis-dichloroethene, and vinyl chloride.

High concentrations of microorganisms can be encapsulated in beads that use their internal energy reserves to promote the transformation of mixtures of chlorinated aliphatic hydrocarbons (CAHs). These high microbial density beads can transform the contaminant mixtures for extended periods of time, such as days, weeks, months, and even years.

The present disclosure provides examples of using such compositions for bioremediation. For example, such compositions can be used as passive barriers to promote the co-metabolism of problematic mixtures of contaminants including chlorinated solvents and the emerging contaminants such as 1,4-dioxane. Barrier walls can be constructed to intercept plumes. Beads could be injected in near zones of low permeability that are slowly diffusing the contaminants. The beads also could be used in well treatment systems, such as recirculation wells.

In sediments, disclosed embodiment could be used to promote the oxidation of PAH contamination. For domestic wastewater reuse, for both potable and non-potable reuse emerging contaminant treatment to very low concentrations may be required. 1,4,dioxane, for example, is not being effectively removed by tertiary treatment systems.

The present compositions also may be used in combination with other remediation materials and methodologies. For example, disclosed embodiments might be used in combination with activated carbon treatment.

The beaded systems might also be used for anaerobic reductive dehalogenation systems were the dehalogenating microorganisms are coencapsulated with slow release substrates to promote more effective anaerobic systems.

III. Contaminants

The present application concerns metabolic transformation, particularly co-metabolic transformation, of contaminants of concern (CoCs), such as by enzymatic degradation of CoCs. The present invention can be used to transform any CoC amenable to such metabolic transformation. Examples of such contaminants include, but are not limited to, cyclic ethers, such as 1,4-dioxane (1,4-dialkoxybenzenes), 1,3-dioxane (1,3-dialkoxybenzenes), tetrahydrofuran, 1,3-dioxalone, and tetrahydropyran; chlorinated ethenes, such as trichloroethene (TCE), 1,2-cis-dichlorethene (cis-DCE), 1,1-dichloroethene (1,1-DCE), 1,2-trans-dichloroethene (trans-DCE), and vinyl chloride (chloroethene) (VC); halogenated alkanes, such as, 1,2,2-tetrachloroethane, 1,1,1-trichloroethane (1,1,1-TCA), 1,1,2-trichloroethene (1,1,2-TCA), 1,1-dichloroethane (1,1-DCA), 1,2-dichloroethane (1,2-DCA), 1,1,1,2-tetrachloroethane, chloroethane, bromoethane, 1,2,3-trichloropropane (TCP), 1,2-dichloropropane, chloroform (trichloromethane), dichloromethane(methylene chloride), chloromethane, bromomethane, dichlorofluoromethane, freons, and difluoromethane (refrigerant); disinfection byproducts, such as N-nitrosodimethylamine (NDMA), chloroform, bromoform, bromodichloromethane, and chlorodibromomethane; halogenated aromatics, such as 1,2-dichlorobenzene, 1,4-dichlorobenzene, chlorophenol, 4-chlorophenol, dichlorophenol, 1,3-dichlorophenol, 2,5-dichlorophenol, pentachlorophenol, and 1,2,4,5-tetrachlorobenzene; perflourinated compounds, such as perfluoropentanoate (PFPeA), perfluorohexanoate (PFHxA), perfluoroheptanoate (PFHpA), perfluorooctanoate (PFOA), perfluorononanoate (PFNA), perfluorodecanoate (PFDA), perfluoroundecanoate (PFUnDA), perfluorohexanesulfonate (PFHxS), and per-fluorooctanesulfonate (PFOS); explosives, including nitroaromatics, such as trinitrotoluene, 2,4,6-trinitrotoluene, cyclotrimethylenetrinitramine (RDX), and nitrobenzene; pesticides, such as bentazone; ethers, such as methyl tertiary butyl ether (MTBE), ethyl tertiary butyl ether (ETBE), tertiary amyl methyl ether (TAME), diisopropyl ether (DIPE), tertiary butyl alcohol (TBA), dimethyl ether (DME), bis(2-chloroethyl)ether (BCEE), and bis(2-chloroisopropyl)ether (BCIP); nitrosamines, such as N-nitrosomorpholine and N-nitrosodimethylamine (NDMA); phthalates, such as di-2-ethylhexyl phthalate, bisphenol A, tetrabromobisphenol A (TBBPA) and 4,4'-diaminostilbene-2,2'-disulfonic acid (DSDA); antibiotics, such as sulfamethoxazole (SMX), pharmaceutically active compounds (PHACs), triclosan, bisphenol, ibuprofen, atenolol, naproxen, ketoprofen, diclofenac, clofibric acid, bezafibrate; natural and synthetic estrogens, such as 17β-estradiol (E2), α-estriol (E3), and 17α-ethinylestradiol (EE2); nonylphenols, such as 4-nonylphenols, 2-nonylphenols, decylphenol, and brominated octylphenoxyacetic acid; polycyclic aromatic hydrocarbons, such as naphthalene, fluorene, phenanthrene, anthracene, fluoranthene, pyrene, benzo[a] pyrene (BaP), benz[a]anthracene, and dibenz[a,h]anthracene; and any and all combinations of these contaminants.

IV. Microorganisms

One aspect of the present disclosure is the selection of microorganisms that can effectively metabolize CoCs of interest. The present application is exemplified primarily by reference to bacteria and fungi. Certain embodiments of the present application are exemplified by using bacteria that include *Rhodococcus rhodochrous*, particularly *Rhodococcus rhodochrous* ATCC 21198 (21198) NS, *Burkholderia vietnamiensis*, particularly *Burkholderia vietnamiensis* strain G4 KR1. However, a person of ordinary skill in the art will also appreciate that the presently disclosed embodiments could be practiced with other bacteria, and the scope of the invention is not limited to using solely *Rhodococcus rhodochrous* ATCC 21198 (21198) NS, or *Burkholderia vietnamiensis* strain G4. A person of ordinary skill in the art will also appreciate that multiple different microorganisms might be used in combination. For example, *Rhodococcus rhodochrous* and *Burkholderia vietnamiensis* might be used in combination, particularly if each can be induced to metabolize different CoCs of interest.

Additional examples of bacteria suitable for practicing the present invention include *Rhodococus jostii* RHA1, *Mycobacterium vaccae* (austroafricanum) JOB5 (ATCC 29678), *Rhodococcus rhodochrous* (ATCC 21198), *Rhodococcus rhodochrous* (ATCC 21197), *Brevibacterium butanicum* (ATCC 21196), *Brevibacterium paraffinoliticum* (ATCC 21195), *Rhodococcus ruber* ENV425, *Sphingopyxis* sp. AX-A, *Pseudonocardia dioxanivorans* CB1190, *Mycobacterium* sp. PH-06, *Acinetobacter baumannii* DD1, *Mycobacterium austroafricanum* IFP2016, *Pseudonocardia* sp, strain ENV478, *Rhodococcus* sp. RR1 N/A, *Flavobacterium* N/A, *Pseudonocardia tetrahydrofuranoxidans* K1, *Burkholderia vietnamiensis* G4, *Ralstonia pickettii* PKO1, *Pseudomonas mendocina* KR1, *Pseudomonas putida* F1, *Pseudomonas putida* mt2, *Aureobasidium pullmans* NRRL 21064, *Graphium* sp. (ATCC 58400) (fungus), *Xanthobacter autotrophicus* Py2, *Rhodococcus rhodochrous* B-276, *Nitrosomonas europaea*, *Ralstonia eutrophus* JMP 134, *Thauera butanivorans*, *Methylosinus trichosporium* OB3b, *Methylomonas methanica* 68-1, *Methylococcus capsulatus* (Bath), *Pseudomonas stutzeri* OX1, *Pseudomonas* sp. DCA1, *Rhodococcus erythropolis*, *Alcaligenes denitrificans*, *Pseudomonas* sp. PS14, *Pseudomonas putida* GPo1, *Arthrobacter* sp. (ATCC 27779), *Corynebacterium alkanum* (ATCC 21194), *B. butanicum* (ATCC 21196), *Arthrobacter* sp. (ATCC 27779), *Mycobacterium vaccae* JOB5 (ATCC 29678*) *R. wratislaviensis* PD630 (DSM 44193*), *Sphingomonas* sp. PH-07, *Sphingomonas* sp, strain PheB4, and *Sphingopyxis* KCY 1.

Fungus, or fungi, also can be used. Examples include *Graphium* sp. (ATCC 58400) (fungus), *Armillaria* sp. F022 (white-rot fungus), and *Pycnoporus sanguineus*.

V. Slow Release Compounds

Certain growth substrates induce production of enzymes that are suitable for metabolic degradation of CoCs. Certain of these growth substrates that are suitable to drive metabolic decontamination are alcohols. Aliphatic carboxylic acids are another example of a suitable growth substrate. Particular embodiments concern lower alkyl alcohols, such as butanol, and aryl alcohols, such as phenol. Suitability may also depend on the regio-position of the hydroxyl functional group for particularly alcohols, such as 1-butanol and 2-butanol.

Another aspect of the present invention is to use slow release compounds that produce growth substrates by hydrolysis over a period of time. As used herein, slow release means that the compounds have half lives on the order of at least one month, more typically 2 to 12 months, and potentially at least one year.

One example of a family of slow-release compounds that has been used for working examples are orthosilicates. Orthosilicates include a silicon atom that can couple with organic moieties such as alcohols and esters. For example, orthosilicates can include four ether linkages attached to alcohol side groups that are released by hydrolysis to produce an alcohol and silicic acid. Orthosilicates also can include different ethers that hydrolyze to produce mixtures of different alcohols. Alcohols have been shown to induce expression of the same monooxygenases expressed by the same bacterial strain when it is grown on isobutane, and these monooxygenase enzymes are useful for transforming contaminants. One compelling benefit of using alcohols to promote cometabolic COC degradation is that these compounds can lead to more effective remediation by eliminating competitive interactions between gaseous growth substrates, such as isobutane and COCs. Accordingly, tetraalkoxysilanes, as alcohol-releasing slow release compounds (SRCs), can be used to support cometabolic COC-degradation by isobutane-oxidizing bacteria. Microcosm studies have established that TCE and cis-DCE co-metabolism can be supported by n-butanol and 2-ethylbutanol released by abiotic hydrolysis of the tetraalkoxysilanes, TBOS and TKEBS. The general equation for the hydrolysis of tetraalkoxysilanes is provided below:

$$Si(OR)4+H2O \rightarrow 4ROH+Si(OH)4$$

The rates of hydrolysis are dependent on pH and the OR group, with longer and more branched OR groups hydrolyzing more slowly.

Another way to slowly release alcohols is by hydrolysis of carboxylic acid esters. Ester hydrolysis releases both alcohols and organic acids and, like tetraalkoxysilanes, the hydrolysis rate is based on the chemical structure of the ester. Carboxylic esters and orthosilicates vary in solubility from slightly soluble smaller compounds, such as sec-butyl acetate with an estimated solubility of 3520 mg/L, to heavier compounds such as benzyl benzoate and tetra-sec-butyl orthosilicate with estimated solubilities' of 15.4 and 3.8 mg/L, respectively. These liquids have the potential to produce non-aqueous phase liquids (NAPL) in solution, which limits the interaction of water molecules with the SRCs due to the surface area and decreases the hydrolysis rate. A range of SRCs can be used to produce various organic acids and alcohols that then induce enzyme pathways that are suitable to co-metabolize COCs.

Certain suitable orthosilicates that have been used with exemplary embodiments have Formula 1.

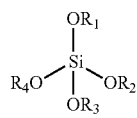

Formula 1

With reference to formula 1, $R_1$-$R_4$ are independently selected from aliphatic and aryl compounds, as exemplified by alkyl groups and phenyl groups. Particular examples of alkyl groups include lower alkyl groups, such as propyl and butyl groups, including branched chain versions thereof, such as isopropyl and sec-butyl. One disclosed embodiment involved growing *Rhodococcus rhodochrous* 21198 in the presence of trichloroethane (1,1,1-TCA) and cis-dichloroethene (cis-DCE) and 1,4-D as common groundwater contaminants along with slow release compounds (SRC) to generate growth substrates to drive the co-metabolic process. The following slow-release compounds have been used as examples with such *Rhodococcus rhodochrous* 21198 transformation examples to exemplify certain features of the present invention:

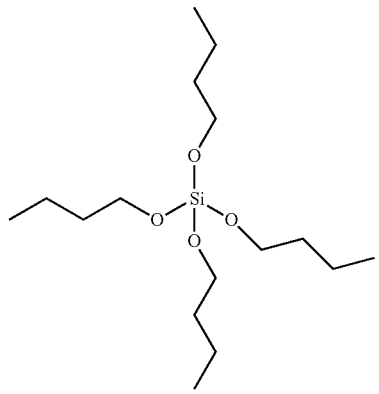

Tetrabutyl orthosilicate (TBOS) -
Hydrolysis Produces 1-Butanol

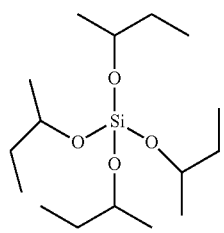

Tetra-sec-butyl orthosilicate (T2BOS) -
Hydrolysis Produces 2-Butanol

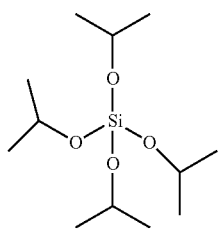

Tetraisopropoxysilane (T2POS) -
Hydrolysis Produces Isopropanol

Through hydrolysis, these compounds produce 1-butanol, 2-butanol, and 2-propanol, respectively. The tetraphenyl-orthosilicate, shown below, that produces phenol upon hydrolysis was used in tests with G4 to cometabolize trichloroethene (TCE), cis-DCE and vinyl chloride (VC).

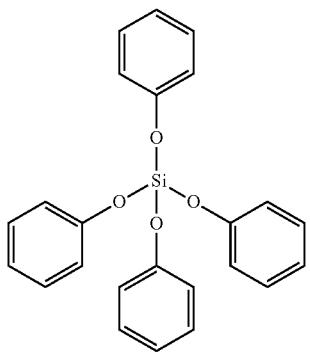

Tetraphenyl-orthosilicate -
Hydrolysis Produces Phenol

Tetra-sec-butyl orthosilicate hydrolyzes to form 2-butanol and silicic acid. Tetrabutyl orthosilicate (TBOS) stimulates both anaerobic and aerobic chlorinated solvent transformation through the hydrolytic release of 1-butanol. In an aerobic and abiotic system, TBOS hydrolysis was most rapid at acidic and basic conditions. For a microbial community enriched on TBOS, hydrolysis rates increased rapidly, suggesting some microbes have an enzyme system able to increase the hydrolysis rate of the ester linkages. A similar compound tetrakis(2-ethylbutoxy)silane (TKEBS) releases 2-ethylbutanol, a branched alcohol, and was found to have an abiotic hydrolysis rate an order of magnitude slower, indicating that hydrolysis rates likely change based on alcohol chain length and linearity.

A person of ordinary skill in the art will appreciate that a number of alcohols and organic acids may be used to form slow release compounds that will function as desired according to the present invention. Table 1 below provides additional information concerning possible acids and alcohols useful for this purpose.

| SUBSTRATE | AMOUNT MMOL | FINAL OD(550) | % REMOVAL | |
|---|---|---|---|---|
| | | | Cis-DCE | TCE |
| Ethanol | 162 | 0.24 | 32% | ND |
| 1-Propanol | 108 | 0.24 | 44% | ND |
| 1-Buntaol | 81 | 0.24 | 98% | 16% |
| Acetate | 243 | 0.33 | 73% | ND |
| Propionate | 139 | 0.30 | 42% | ND |
| Butyrate | 97 | 0.40 | 93% | 9% |
| Benzoate | 65 | 0.24 | 84% | 6% |
| Acetone | 122 | 0.22 | 58% | ND |
| Phenol | 69 | 0.21 | 100% | 100% |
| p-cresol | 57 | 0.19 | 100% | 100% |
| 3-buten-2-ol | 88 | 0.03 | ND | ND |
| 3-buten-1-ol | 88 | .022 | 89% | 21% |
| 2-buten-1-ol | 88 | .023 | 67% | 20% |
| Glucose | 81 | 0.40 | 93% | 44% |
| Benzyl alcohol | 57 | .018 | 100% | 100% |

Figure 2:
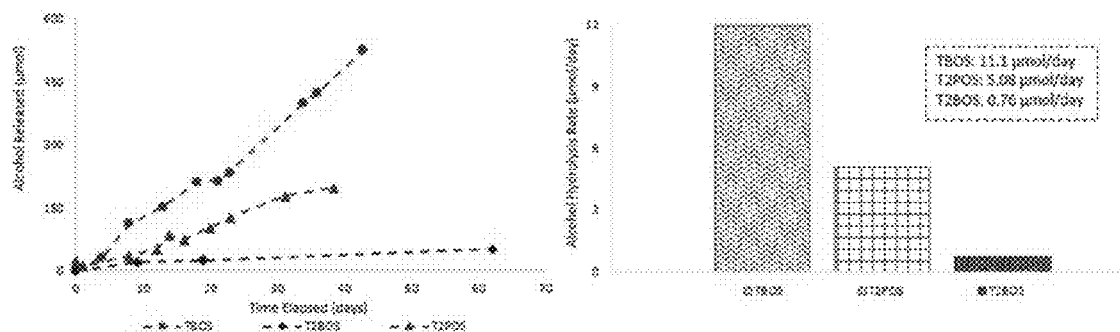
FIG. 2 is a graph of alcohol released versus time to compare the release of alcohols from orthosilicate slow release compounds and the microbial utilization of the alcohols.
Figure 3:
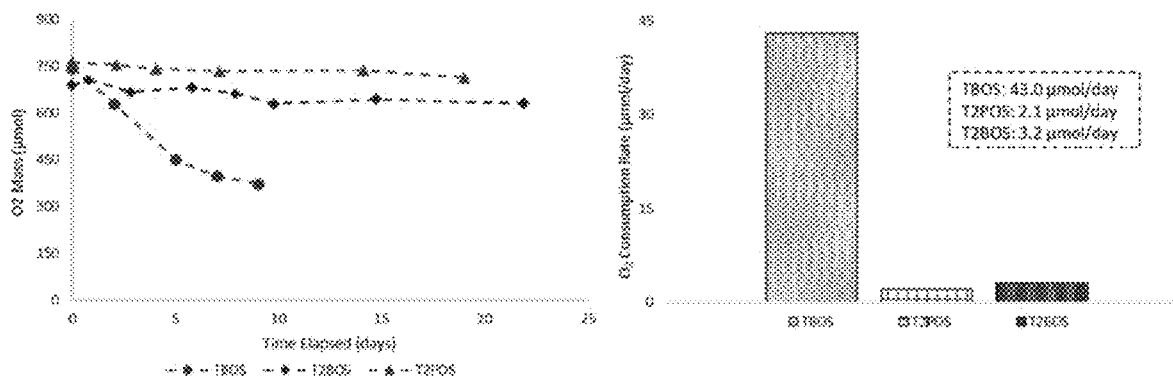
FIG. 3 is a graph of O2 mass consumed versus time (days) to compare the release of alcohols from orthosilicate slow release compounds and the microbial utilization of the alcohols.

To compare the release of alcohols from the orthosilicates and the microbial utilization of the alcohols, $CO_2$ production (FIG. 1), alcohol release (FIG. 2), and $O_2$ consumption (FIG. 3) were plotted for the three exemplary orthosilicates. The rate of alcohol release from the parent orthosilicate were as follows: TBOS>T2POS>T2BOS. The rate of production of $CO_2$ was consistent with the rate of alcohol production, while the rate of $O_2$ consumption correlated with the rate of $CO_2$ production. Branched R groups on ether linkages create some steric hindrance that slows the hydrolysis reactions. T2BOS therefore hydrolyses at a rate roughly an order of magnitude slower than TBOS. Additionally, it is theorized that chain length plays a factor in hydrolysis rates, with longer substituted groups hydrolyzing more slowly than smaller ones, explaining why T2POS releases 2-propanol more rapidly than T2BOS releases 2-butanol.

Particular disclosed examples focus on the orthosilicates as SRCs and their co-encapsulation in hydrogel beads. However, a person of ordinary skill in the art will appreciate that other compounds can be used as SRCs according to the present disclosure. For example, additional examples of SRCs include oils, including vegetable oils, that ferment and hydrolyze to form organic acids; polymers that hydrolyze to form lactate or lactate-like substrates; and oils that slowly dissolve into solution, but can be directly utilized by bacteria, such as limonene.

VI. Encapsulation

Certain disclosed embodiments concern co-encapsulating microbial cells and SRCs inside an encapsulating material, such as a gel or a bead, to produce compositions sufficiently robust and efficacious to metabolically degrade CoCs. A person of ordinary skill in the art will appreciate that any material capable of co-encapsulating microorganisms and slow release materials for the purpose of metabolic remediation can be used to practice the present invention.

Beads and encapsulating materials are exemplified herein by reference to natural polysaccharide hydrogels, such as alginate and gellan gum matrices. Accordingly, methods were developed for co-encapsulation of slow release compounds (SRC), such as TNOS and T2BOS, with bacterial cultures, typically pure cultures, in alginate and gellan gum hydrogel beads. The gum matrices can be loaded with any amount of both an SRC and microbial cells that can be accepted by such materials, but are particularly suitable for high mass loadings. High mass loadings as referred to herein means a mass loading of at least 10% (w/w), and typically greater than 10% (w/w). Co-encapsulated bacterial cultures consumed SRC products, such as 1- and 2-butanol, before these substrates diffuse from the beads.

Figure 4:
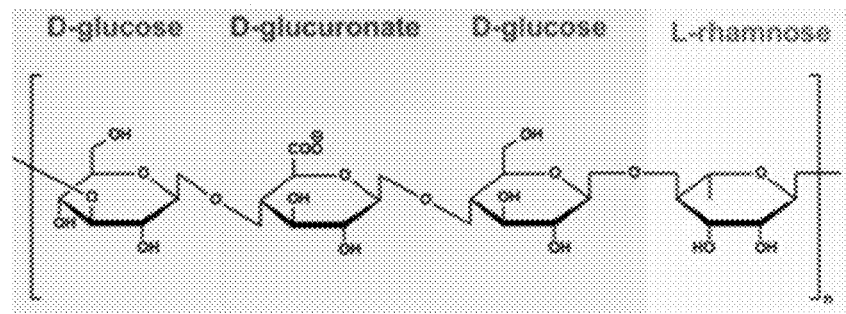
FIG. 4 provides the structure of the polysaccharide gellan gum.

Gellan gum microbeads can be produced to sub-millimeter diameters (12-135 μm) with superior rheological properties to agar and carrageenans. Gellan gum (GG) is a relatively newly discovered natural gelling polysaccharide produced primarily by Sphingomonas elodea, and includes chains of glucose, glucuronic acid, and rhamnose molecules (FIG. 4). Similar to alginate, the gelation of GG occurs via ionic crosslinking; however, in contrast to alginate, crosslinking can occur with a variety of mono and divalent cations. Though GG gelation is ionically activated, the gelation process is more similar to the thermal hysteresis type gelation of agar and agarose. GG gelation temperatures are dependent on the type and concentration of crosslinking cations, concentration of GG, and concentration of chelating agents. GG replaced hydrogel matrices like agar and alginate because it has been found to have superior rheological properties, chemical stability, temperature resistance, enzyme resistance, and clarity at lower concentrations of hydrogel and ionic crosslinkers. GG has a similar structure, but is more durable and similarly biocompatible at lower concentrations, than other natural polysaccharides, which decreases operational costs of producing large quantities of bioactive beads.

Microbial encapsulation with gellan gum involves heating a pre-gel solution to at least 60° C. followed by a direct addition of crosslinking cation salts or solutions and cooling typically to about 35° C. to initiate gelation. The temperature dependent crosslinking of GG provides simple emulsification internal gelation that can be used to create highly stable spherical micro-beads ranging in size from below 20 μm to above 150 um.

An emulsification-internal gelation method has been used to create sub millimeter microbeads with encapsulated pure cultures. In this method a 0.75% (w/v) dispersion on gellan gum in sterile water is heated to 75° C. to dissolve and form a pregel solution (sol). A suspension of cells in 0.1% (w/v) $CaCl_2$ is mixed with the sol after it cools to 45° C. The sol/gel mixture is then emulsified in canola oil and a non-ionic oil soluble surfactant, Span 80. The mixture is emulsified at high mixing speeds and gelation is then initiated by rapidly lowering the temperature to 15° C. with continued stirring. The oil is removed by aspiration as the microbeads partition into the water. The beads are washed repeatedly with a Tween 80 solution. This process produced microbeads in the size range of 15-30 μm using mixing speeds of 4,500 rpm and a 10-minute emulsification period.

Gellan-gum matrices tend to be more robust than alginate, and gellan-gum matrices therefore were selected for certain long-term tests. However, different crosslinking methodologies may be used to tailor the mechanical strength and chemical stability of encapsulating materials for a particular desired result. For example, crosslinking the encapsulating material can affect mechanical strength and chemical stability of the encapsulating material, as can the method used to crosslink. Alginate can be crosslinked using $Ca^{2+}$ salts; however, when $Ca^{2+}$ salts are replaced by $Ba^{2+}$ salts as the cross-linking agent, beads are formed that have increased mechanical and chemical stability. Similar improvements can be made using gellan-gum A wide range of encapsulating compounds and procedures can be used. Alginate has been frequently used and enables cell encapsulation in a hydrogel. Other potential encapsulation materials include agarose, chitosan, carrageenan, cellulose triacetate, gellan-gum, polyvinylalcohol (PVA) and polyalkylene alcohols, such as polyethethylene glycol. To increase biocompatibility and mechanical stability, alginate is often mixed with other immobilizing compounds, such as agarose, chitosan, poly-L-ornithine, and cellulose sulfate.

Encapsulation provides certain benefits over non-encapsulated cultures. For example, SRCs can be encapsulated with microorganisms in hydrogels to promote long term cometabolic treatment systems. Furthermore, the energy gained from using 1- and 2-butanol by encapsulated cultures increased the survivability, overall activity, and contaminant transformation rate and capacity of initially augmented biomass. For example, in batch systems, cells co-encapsulated with SRCs were able to maintain co-metabolic transformation potential for over 300 days. In contrast, similar cellular biomass suspended in media lost the majority of CoC transformation potential after the first 12 days. Repeated transformation of a mixture of 1,1,1-TCA, cis-DCE and 1,4-D was achieved over a period to 300 days of incubation. 1,4-D transformation followed first-order transformation kinetics, and concentrations below 1 μg/L could be achieved. Higher rates of metabolism and co-metabolism were observed with cells co-encapsulated with TBOS compared to $T_2BOS$, due to the higher rate of hydrolysis. Much lower rates of $O_2$ consumption were achieved by the $T_2BOS$ system, potentially making it more attractive for passive in-situ treatment.

Encapsulating beads can be made in a variety of shapes and sizes. For example, both microbeads and macrobeads can be produced. Microbeads at sizes less than 100 μm may facilitate transport in porous media, and provide improved contaminant transformation results. Macrobeads have a dimension greater than 100 μm, typically at least 1 mm.

Figure 5:
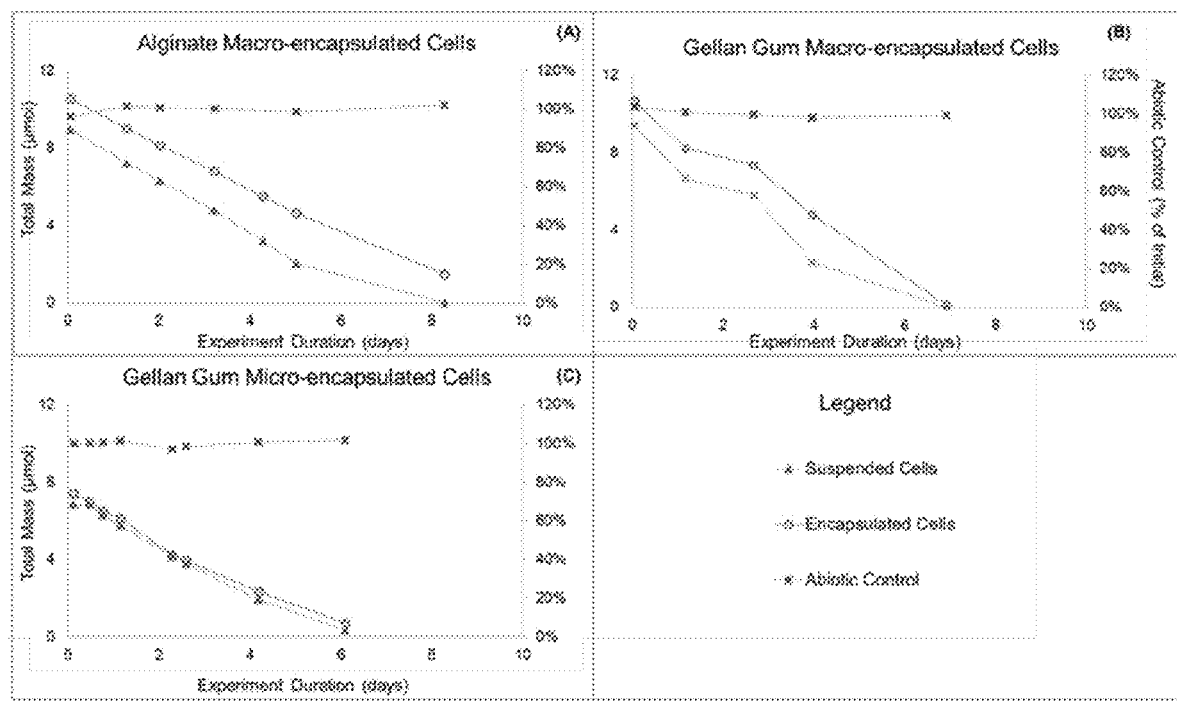
FIG. 5 provides isobutane utilization curves measured for ATCC 21198 suspended and encapsulated in (A) spherical alginate macro-beads ~2 mm in diameter, (B) cylindrical gellan gum macro-beads ~2 mm×2 mm and, (C) spherical gellan gum micro-beads ~10-100 µm in diameter where all data points are averages of duplicate reactors.

Embodiments of the present invention have established that microbial cells can be encapsulated and that the encapsulated cells maintain their viability. For example, it was determined that ATCC 21198 could be encapsulated in both alginate and gellan gum matrices with minimal to no loss of cell viability, as determined via comparison to suspended cell substrate utilization rates (Table 2) (FIG. 5).

TABLE 2

| Encapsulation Matrix/Method | Benchmark Suspended Cell Utilization Rate (μmol/day/mg) | Encapsulated Cell Utilization Rate (μmol/day/mg) | Percent Difference |
|---|---|---|---|
| Alginate Macro-bead | 15.8 | 14.2 | −10.1% |
| Gellan Gum Macro-bead | 13.3 | 13.3 | −0.6% |
| Gellan Gum Micro-bead | 11.1 | 11.0 | −0.7% |

With reference to Table 2, encapsulated cell viability assessment, percent difference is calculated as the percent change from suspended cell utilization rates to encapsulated cell utilization rates. Alginate macrobeads were spherical and ~2 mm in diameter. Gellan gum macrobeads were cylindrical and ~2 mm in diameter by ~2 mm tall. Gellan gum micro-beads were spherical ~10-100 m in diameter.

VII. Packed Columns

As indicated above, encapsulated microorganisms and suitable SRCs can be used directly to transform CoCs to levels of substantially lesser environmental concern than prior to transformation. Such encapsulated compositions can also be used in devices designed to assist transformation. For example, one disclosed embodiment concerns using packed columns of co-encapsulated beads. A particular example concerns *Rhodococcus rhodochrous* 21198 and TBOS and $T_2BOS$ packed in a continuous flow through columns for treatment. Very high degrees of transformation, e.g. over 99%, of mixtures of 1,1,1-TCA, cis-DCE, and 1,4-D have been achieved with hydraulic residence times of 6 to 12 hours. Such columns can operate substantially continuously, with working embodiments operating for over several months of continuous operation. These types of products can be used to prepare a subsurface reactive barrier with the co-encapsulated beads for treating drinking water, domestic wastewater treatment and industrial waste treatment for contaminants of emerging concern.

VIII. Methods of Using Encapsulated SRCs and Microbial Cell to Transform CoCs

A. Introduction

Certain embodiments of the present invention concern transforming contaminants into more environmentally benign components using compositions according to the disclosure that comprise microbial cells, including mixtures of different species of microbial cells, at least one co-metabolism substrate to induce selected enzyme production by the microbial cells, such as at least one slow release compound that induces production of oxygenases, and a bead or gel encapsulating the microbial cells and the at least one co-metabolism substrate. In general, these embodiments comprise contacting a contaminant with such compositions, or contacting a material comprising at least one contaminant with such compositions, with an amount of the composition effective to transform the contaminant. This process can result in formation of a second composition comprising the contaminant.

A person of ordinary skill in the art will appreciate that any material comprising a contaminant can be processed according to this methodology. The material comprising the contaminant can be a solid material or a fluid. Examples of solid materials include soils, sediments, aquifer materials, such as rock, gravel, sand or silt, ice, glaciers and snowfields. Examples of fluids include both gases and liquids. Exemplary gases include: air and oxygen; industrial gases, such as helium, hydrogen, nitrogen; volatile organic compounds that can exist both as gases and liquids at moderate temperatures, such as benzene, ethylene glycol, formaldehyde, methylene chloride, tetrachloroethylene, toluene, xylene, and 1,3-butadiene; and any and all combinations thereof. Exemplary liquids include drinking water and water intended for household uses; wastewater treatment, both for potable and non-potable reuse; wells; groundwater; ponds, rivers, lakes, oceans; and organic liquids.

B. Supporting Data

Disclosed embodiments establish that an SRC, when combined with a selected microorganism culture, such as culture of bacteria, can co-metabolize a broad range of CoCs.

A series of batch tests have been performed where *Rhodococcus rhodochrous* 21198 was grown in the presence of TBOS, T$_2$BOS, or T2POS. Continuous transformation of 1,1,1-TCA was observed at first-order rates of 0.47, 0.037, and 0.14 day$^{-1}$, respectively. 1,4-D transformation by *Rhodococcus rhodochrous* 21198 grown on TBOS, T2BOS, or T2POS was observed at first order rates 0.76, 0.04, and 0.24 day$^{-1}$, respectively. Rates of alcohol release, CO$_2$ production, O$_2$ consumption, and 1,1,1- and 1,4-D transformation, when *Rhodococcus rhodochrous* 21198 was grown in the presence of orthosilicates, follow the trend: TBOS>T2POS>T2BOS. Without being limited to a theory of operation, this trend may indicate that linear alcohols are hydrolyzed more quickly from orthosilicates than short-branched alcohols, which are produced by hydrolysis quicker than long-branched alcohols.

For *Rhodococcus rhodochrous* 21198, a short chain alkane monooxygenase (SCAM) was identified that was associated with co-metabolism of 1,4-D. The detection of SCAM expression was evaluated using an activity-based labeling (ABL) approach. ABL testing was used to identify alcohol growth substrates that induce SCAM expression and activity and result in co-metabolic transformation of contaminants, such as 1,4-D and CAHs. *Rhodococcus rhodochrous* 21198 was able to grow on a broad range of primary and secondary alcohols, organic acids, and lactate. Results of ABL measurements established that SCAM activity was also observed after growth on 2-butanol. SCAM activity, however was not induced by growth on 1-propanol, 1-butanol, ethanol or isobutanol. Protein labeling illustrated the induction of SCAM activity on 2-butanol. See FIG. 6. Lane 1 shows cells grown on isobutane that requires SCAM for it utilization provides the strongest banding pattern. However, a banding pattern is also observed by cells grown on 2-butanol that does not require SCAM to be utilized. A faint banding pattern is also observed when *Rhodococcus rhodochrous* 21198 is grown on 2-propanol. No banding pattern was observed with 1-butanol; however, when *Rhodococcus Rhodochrous* 21198 is grown on 1-butanol generated from the hydrolysis of TBOS, cometabolism is achieved.

Figure 7:
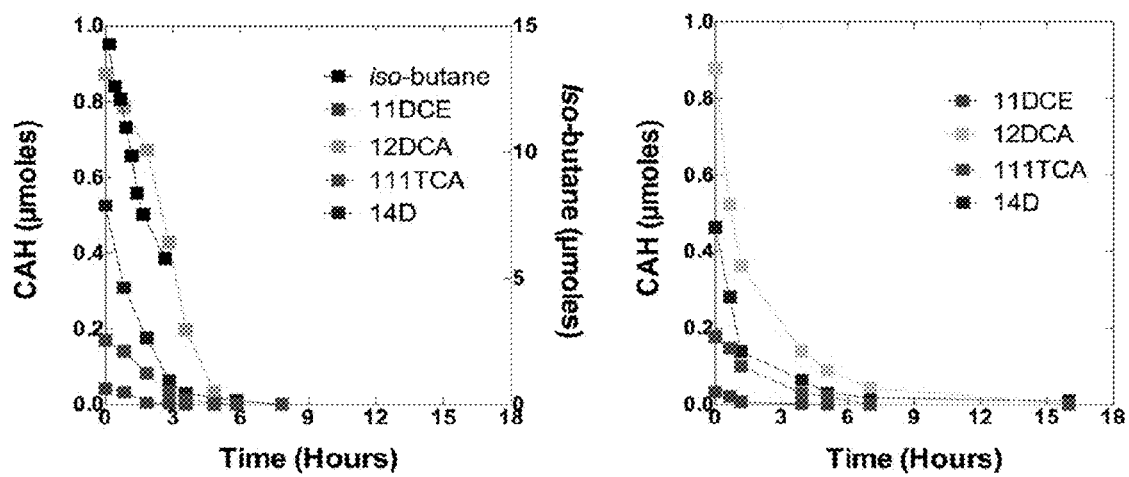
FIG. 7 shows the resting cell co-metabolic transformation of mixtures of chlorinated ethanes (1,1,1-TCA and 1,2-DCA), the chlorinated ethene (1,1-DCE) and 1,4-D by Rhodococcus rhodochrous 21198 when grown on isobutane.

FIG. 7 shows the resting cell co-metabolic transformation of mixtures of chlorinated ethanes (1,1,1-TCA and 1,2-DCA), the chlorinated ethene (1,1-DCE) and 1,4-D by *Rhodococcus rhodochrous* 21198 when grown on isobutane. Rapid transformation of the COC mixture was achieved. The data on the left of FIG. 7 shows the transformation in the presence of isobutane while transformation in the absence of isobutane is shown on the right of FIG. 7. More rapid transformation was observed in the absence of isobutane. This results for the competitive inhibition of SCAM enzyme by isobutane, which slows the co-metabolic transformation. Competitive inhibition of the growth substrate on the co-metabolism is frequently observed. See, for example, Kim et al., 2002A; 2002B. One aspect of the present invention therefore is to drive a co-metabolic process by appropriate selection of non-competitive substrates, like 2-butanol, so that competitive inhibition is avoided, resulting in an efficient co-metabolic process.

Figure 6:
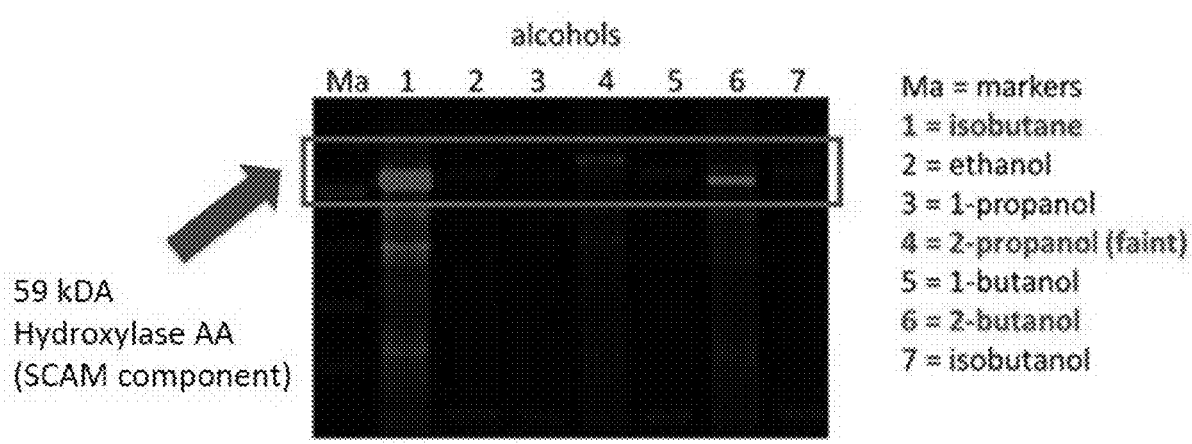
FIG. 6 illustrates labeling of the 59 kDA protein of the short chained monooxygenase enzyme responsible for the co-metabolic transformation of 1,4-D and a broad range of chlorinated solvents.
Figure 8:
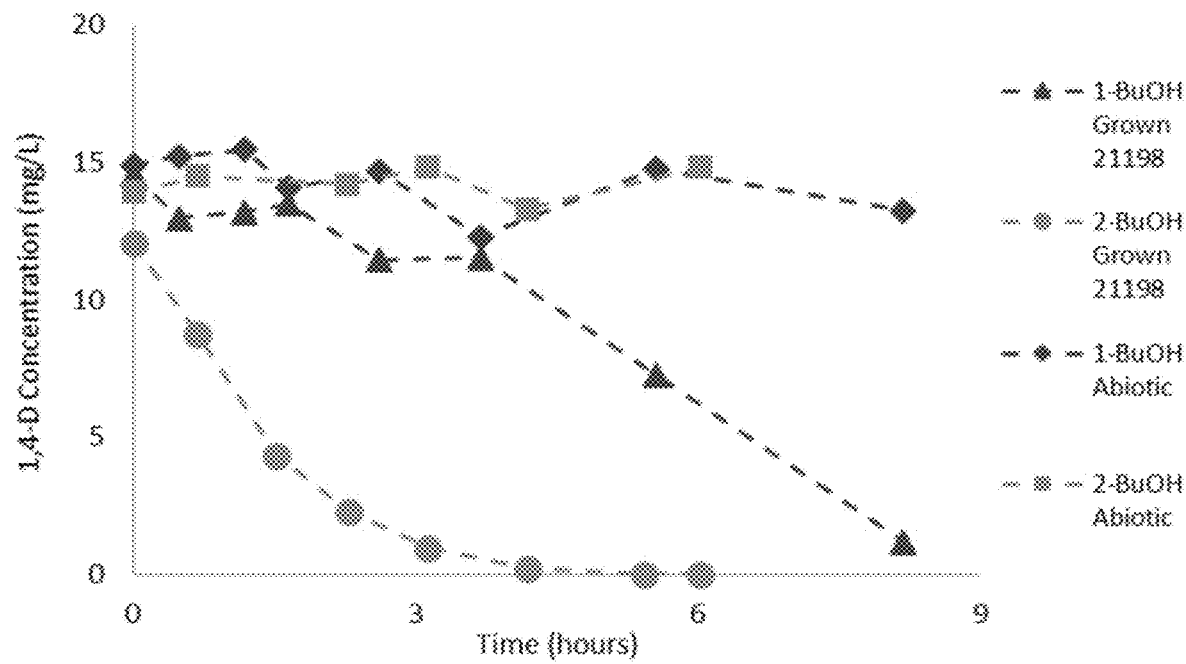
FIG. 8 shows the resting cell co-metabolic transformation of 1,4-D by Rhodococcus rhodochrous 21198 grown on 2-butanol and 1-butanol.

FIG. 8 shows the resting cell co-metabolic transformation of 1,4-D by *Rhodococcus rhodochrous* 21198 grown on 2-butanol and 1-butanol. 1,4-dioxane was immediately transformed by resting cells grown on 2-butanol, indicating the production of SCAM during growth, consistent with the labeling pattern shown in FIG. 6. However, with 1-butanol-grown cells, a lag period was observed before 1,4-D was transformed. The results suggest induction of the SCAM enzyme after growth. These results are also consistent with the labeling results shown in FIG. 6. The presence of SCAM was not observed by cells immediately harvested after being grown on 1-butanol. The process causing the production of SCAM after the lag period is not currently know. FIG. 8 shows the results of resting cell transformation tests with cells grown on 2-butanol in the presence and absence of 2-butanol. The rate of 1,4-D transformation is similar in the presence of 2-butanol indicating the lack of inhibition of 2-butanol on 1,4-D transformation.

Figure 9:
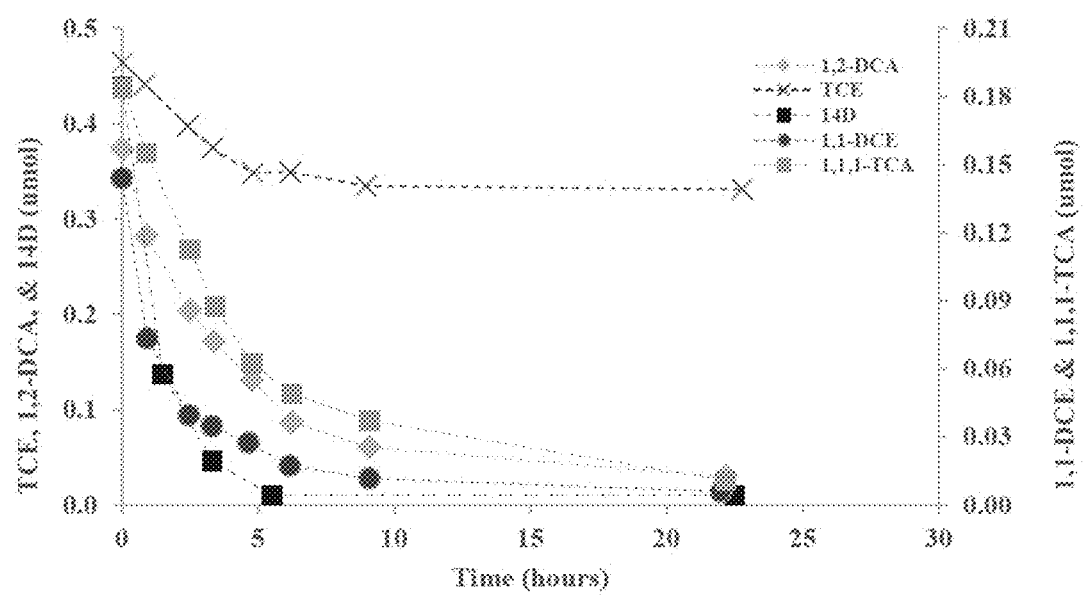
FIG. 9 provides the results of resting cell transformation tests of single COCs with Rhodococcus rhodochrous 21198 grown on 2-butanol.

FIG. 9 provides the results of resting cell tests will *Rhodococcus rhodochrous* 21198 grown on 2-butanol. Cells grown on 2-butanol were able to cometabolize the same COCs as isobutane grown cells. 1,1-dichloroethene (1,1-DCE), 1,2-dichloroethane (1,2-DCA), 1,1,1-TCA and 1,4-D were transformed at rates that were 30% to 50% of isobutane-grown cells. TCE was the most slowly transformed of the CAHs tested with both isobutane- and 2-butanol-grown cells.

Figure 10:
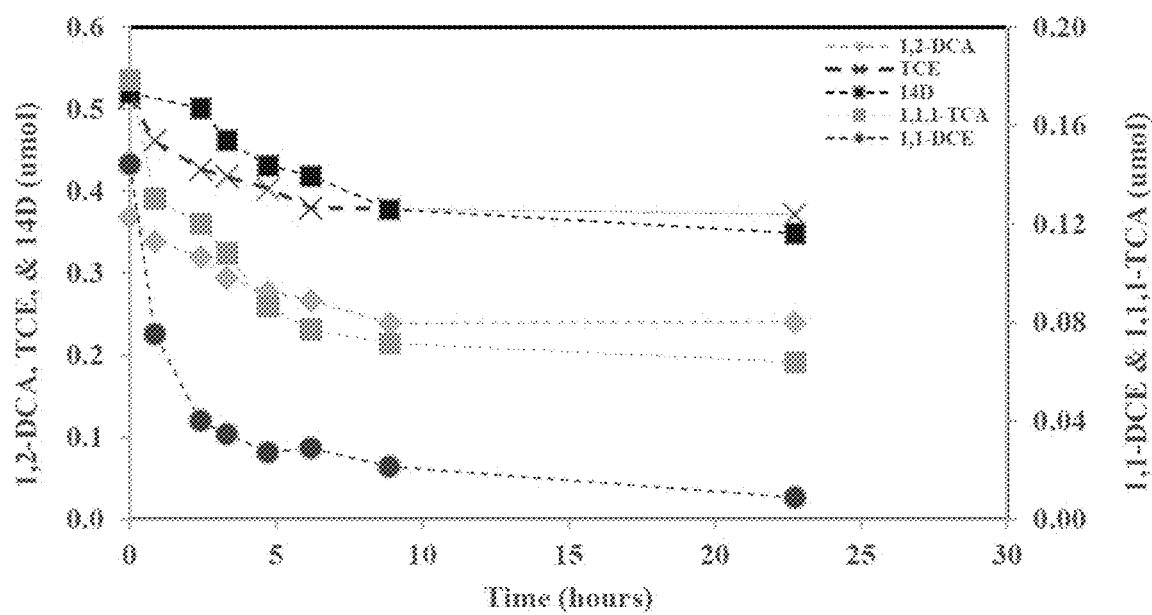
FIG. 10 shows the results of resting cell tests of a mixture of COCs by cell grown on 2-butanol.

FIG. 10 shows the results of resting cell tests of a mixture of COCs by cell grown on 2-butanol. Mixtures of 1,1-DCE, 1,2-DCA, 1,1,1-TCA, TCE and 1,4-D were also transformed, but rates and extents of transformation decreased compared to the single compound tests (FIG. 9), due to transformation capacity limitations.

Figure 11:
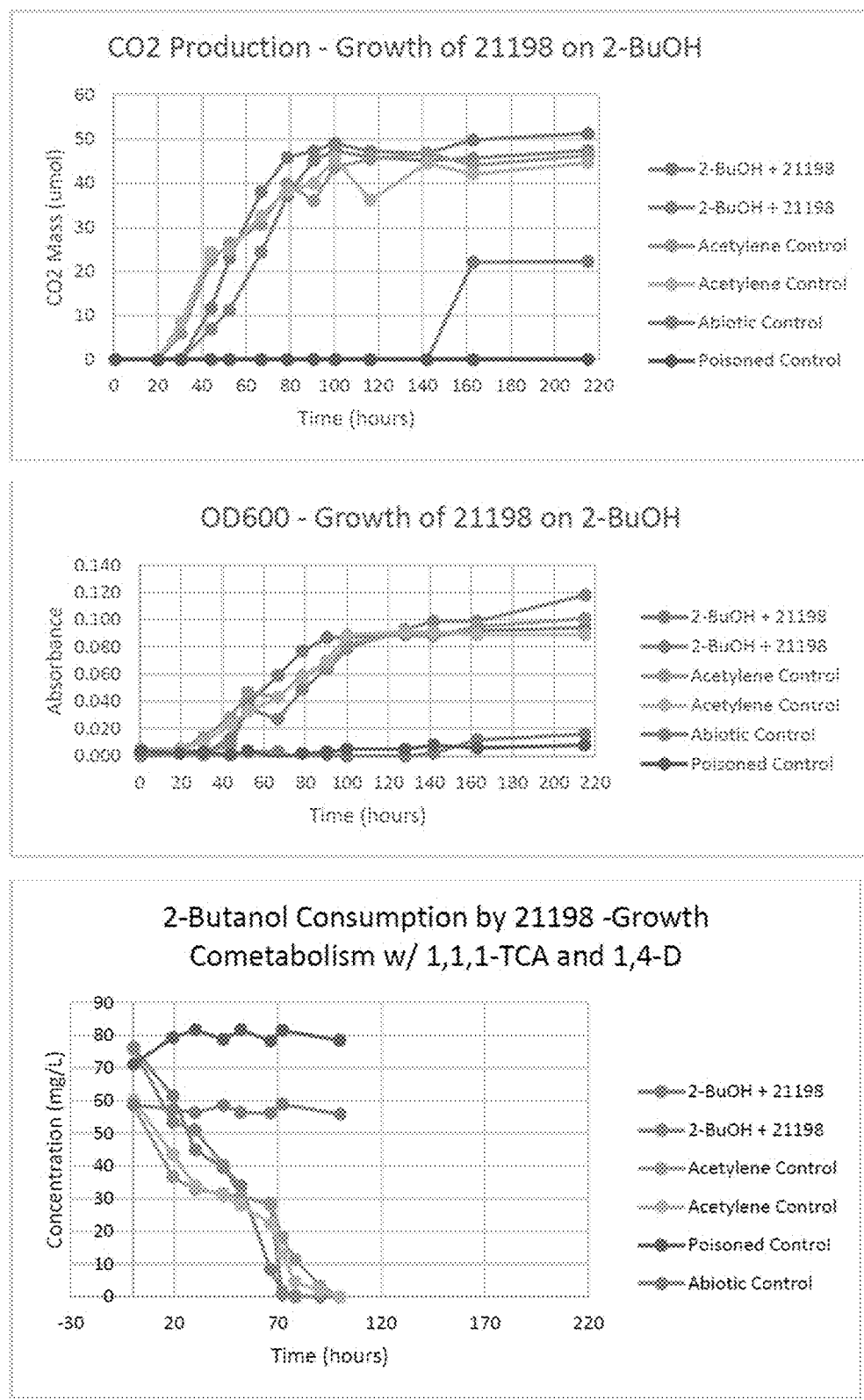
FIG. 11 illustrates production of CO (top), increase in optical density (middle) and 2-butanol consumption (bottom) in batch reactors during 21198 growth in 2-butanol to evaluate co-metabolism of 1,4-D and 1,1,1-TCA was evaluated during growth of Rhodococcus rhodochrous 21198 on 2-butanol.
Figure 12:
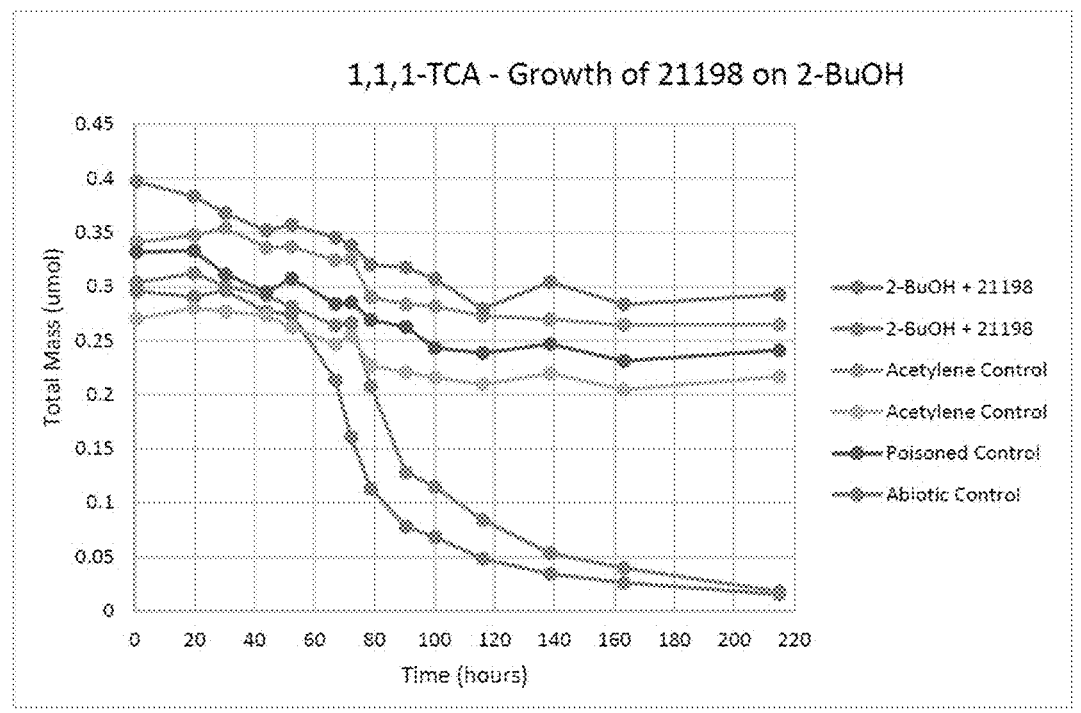
FIG. 12 illustrates transformation of 1,1,1-TCA and 1,4-D during growth on 2-butanol.
Figure 12:
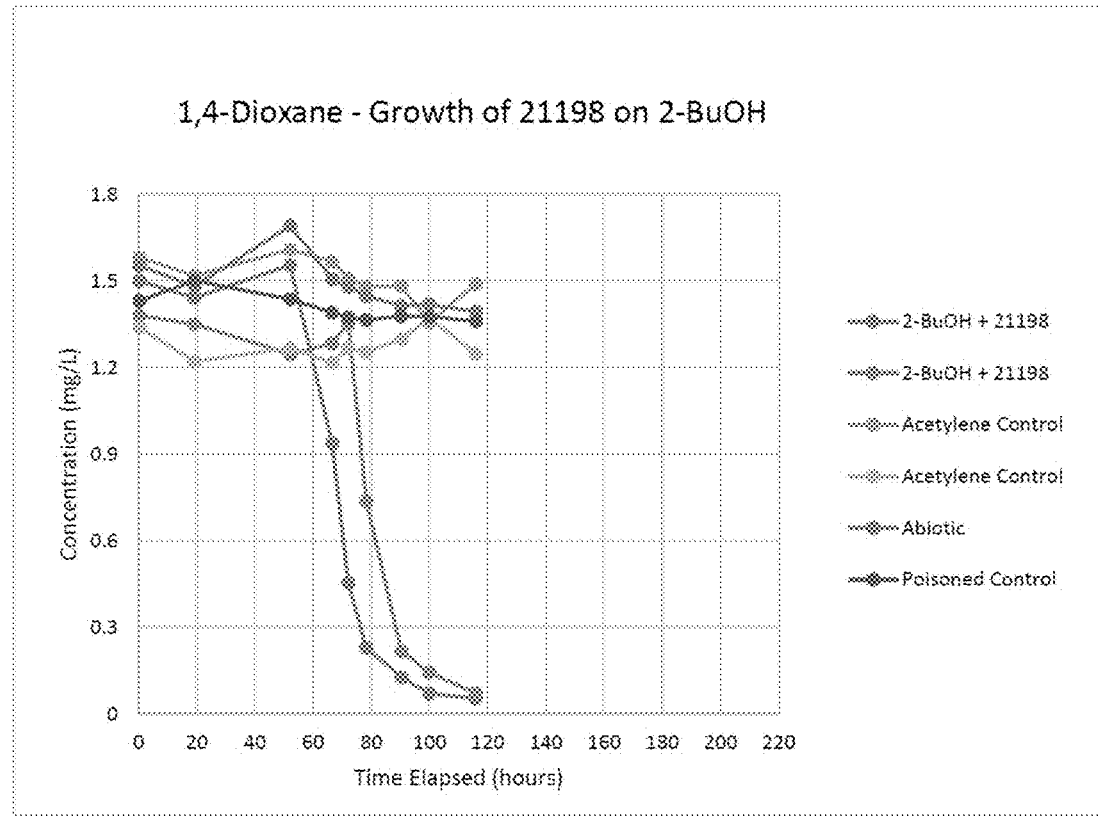

Co-metabolism of 1,4-D and 1,1,1-TCA was evaluated during growth of *Rhodococcus rhodochrous* 21198 on 2-butanol. Growth on 2-butanol was tracked by the production of CO$_2$, the increase in optical density and the consumption of 2-butanol (FIG. 11). Growth of *Rhodococcus rhodochrous* 21198 and 2-butanol consumption occurred in the presence of acetylene, an potent inhibitor of monooxygenase enzymes, indicating SCAM was not required for 2-butanol consumption. 1,4-D and 1,1,1-TCA cometabolic transformation were found to be correlated with the growth of *Rhodococcus rhodochrous* 21198 (FIG. 12). It should be noted that the presence of acetylene blocked the transformation of 1,1,1-TCA and 1,4-D, indicating the monooxygenase enzyme was required for their co-metabolic transformation.

Growth of Rhodococcus rhodochrous 21198 and 1,4-D and 1,1,1-TCA co-metabolism was also evaluated with growth of Rhodococcus rhodochrous 21198 on sec-butyl-acetate, an ester that hydrolyzes to form 2-butanol and acetate. Esters can be used as SRCs since hydrolysis is required to produce an organic acid and an alcohol. FIG. 9 shows the production of $CO_2$, increase in optical density and oxygen consumption during the growth of 21198. Consistent with previous observations, acetylene did not inhibit the growth on sec-butyl-acetate. Consistent with tests involving 2-butanol alone, 1,1,1-TCA was co-metabolized during growth of Rhodococcus rhodochrous 21198 on sec-butyl-acetate. The inhibition of 1,1,1-TCA transformation in the presence of acetylene also demonstrates the monooxygenase being responsible for the transformation. The results indicate that sec-butyl acetate that hydrolyzes to form 2-butanol and acetate has potential as an SRC, and establishes that esters might be used as slow release substrates.

Particular examples of COC transformations are provided below.

1. COC Transformation by 21198 During Growth on T2BOS

T2BOS (tetra-sec-butyl orthosilicate) releases 2-butanol, but is not nearly as soluble as sBA; T2BOS solubility is estimated at 6.8 mg/L compared to sBA at 3520 mg/L [2]. It was theorized that, due to the lower solubility, the rapid utilization of the SRC that occurred in the sBA example shown in FIG. 12, would not be observed for the T2BOS experiments. T2BOS, as a branched orthosilicate, hydrolyzes very slowly.

Previous literature and laboratory observations indicate that there is an increase in release of alcohol from orthosilicates when the orthosilicate is at a higher concentration [3]. To increase 2-butanol production from the hydrolysis pathway to an easily quantifiable level, the starting concentration of T2BOS of 1500 mg/L was used. The addition was made using neat T2BOS obtained from Gelest, Inc., which was 95% pure. The growth indicators for this experiment (FIG. 13) show a rapid increase in $CO_2$, likely from the 2-butanol impurity present in the neat T2BOS addition. After that, a constant and gradual increase in $CO_2$ was observed over 125 days. Also shown is the production of $CO_2$ in the batch reactor containing acetylene. This observation is consistent with 2-butanol utilization not requiring SCAM. No $CO_2$ production was observed in the poisoned control.

Figure 13:
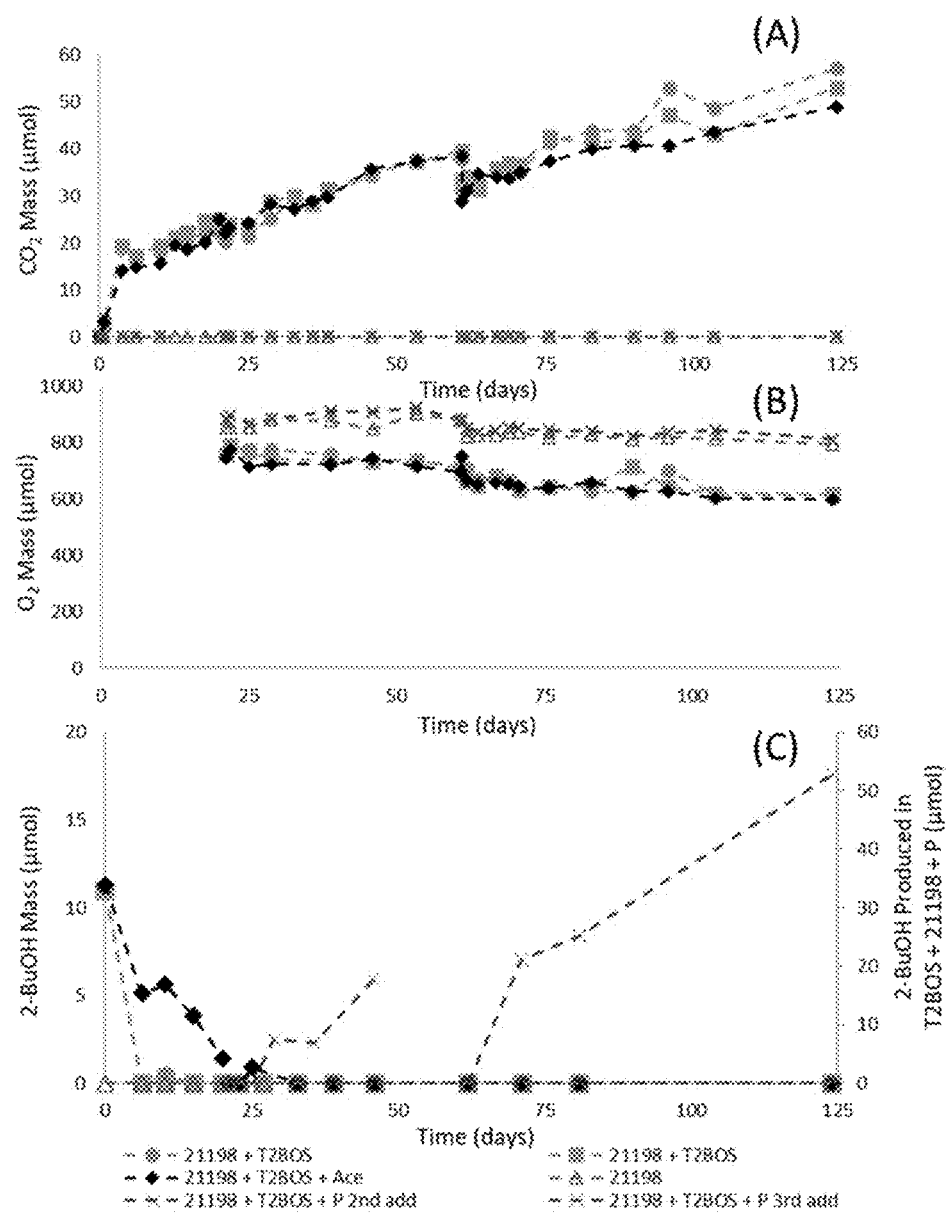
FIG. 13 illustrates production of $CO_2$ (A), consumption of $O_2$ (B) and total mass of aqueous 2-butanol (C) in batch reactors during growth on T2BOS. "Ace" is acetylene. 21198 (green triangles) is the inoculum control.
Figure 15:
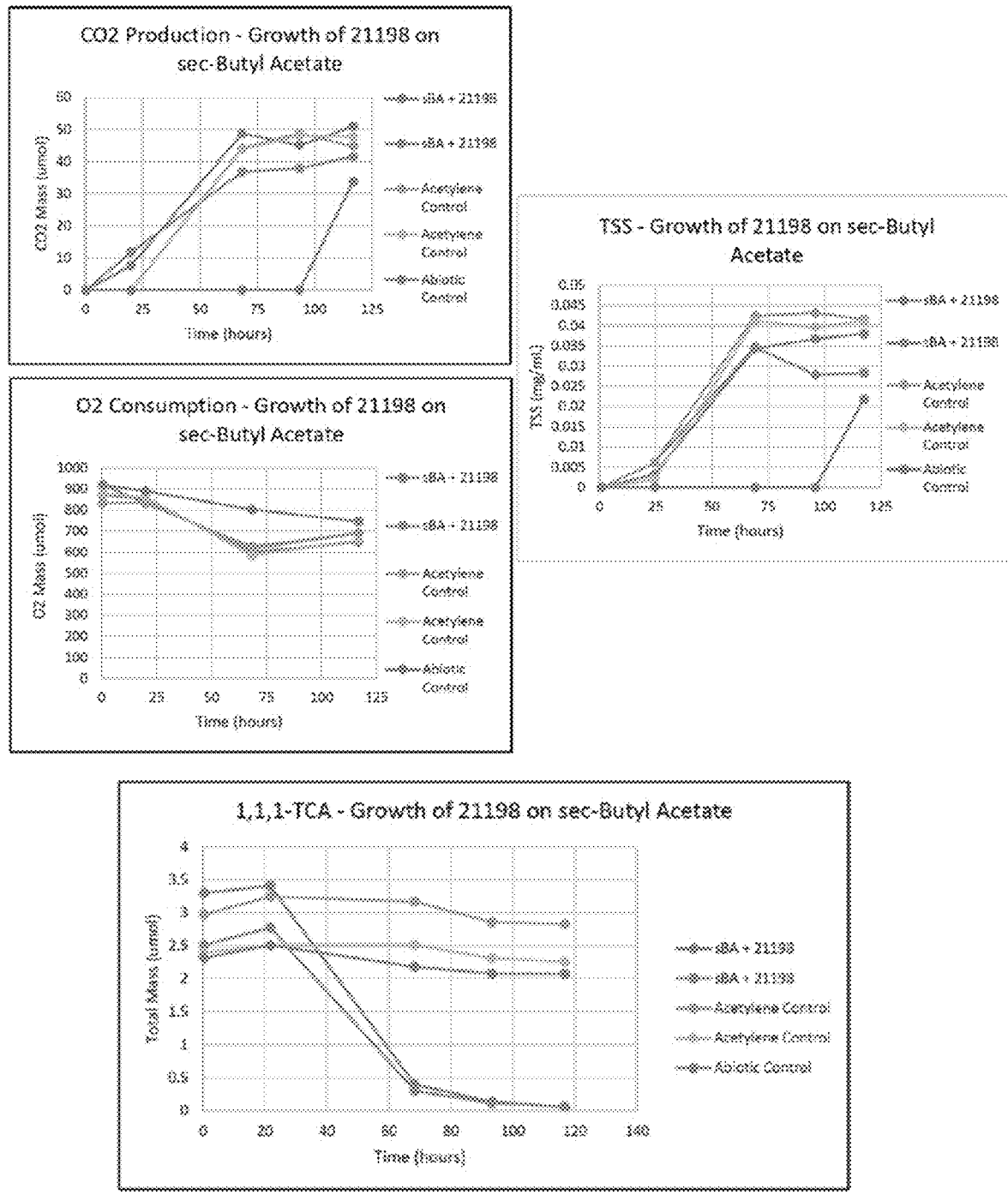
FIG. 15 illustrates growth of 21198 on the ester sec-butyl-acetate that hydrolyzes to form acetate and 2-butanol and the cometabolic transformation of 1,1,1-TCA.

A slow but gradual rate of $O_2$ consumption was observed, when headspace $O_2$ concentrations are compared to the poisoned controls (FIG. 13). $O_2$ consumption was observed in all the reactors where $CO_2$ production was observed. T2BOS is not rapidly utilized by 21198 like observed with sBA (FIG. 15), and 2-butanol is released by abiotic hydrolysis. The slow rate of hydrolysis is indicated by the measured 2-butanol concentrations in the poisoned reactor. Over the period of 60 to 125 days approximately 50 μmol of 2-butanol was formed. After the initial 2-butanol was consumed (0 to 30 day), 2-butanol was not detected in the aqueous phase indicating that it was rapidly utilized as it was continuously formed.

Figure 14:
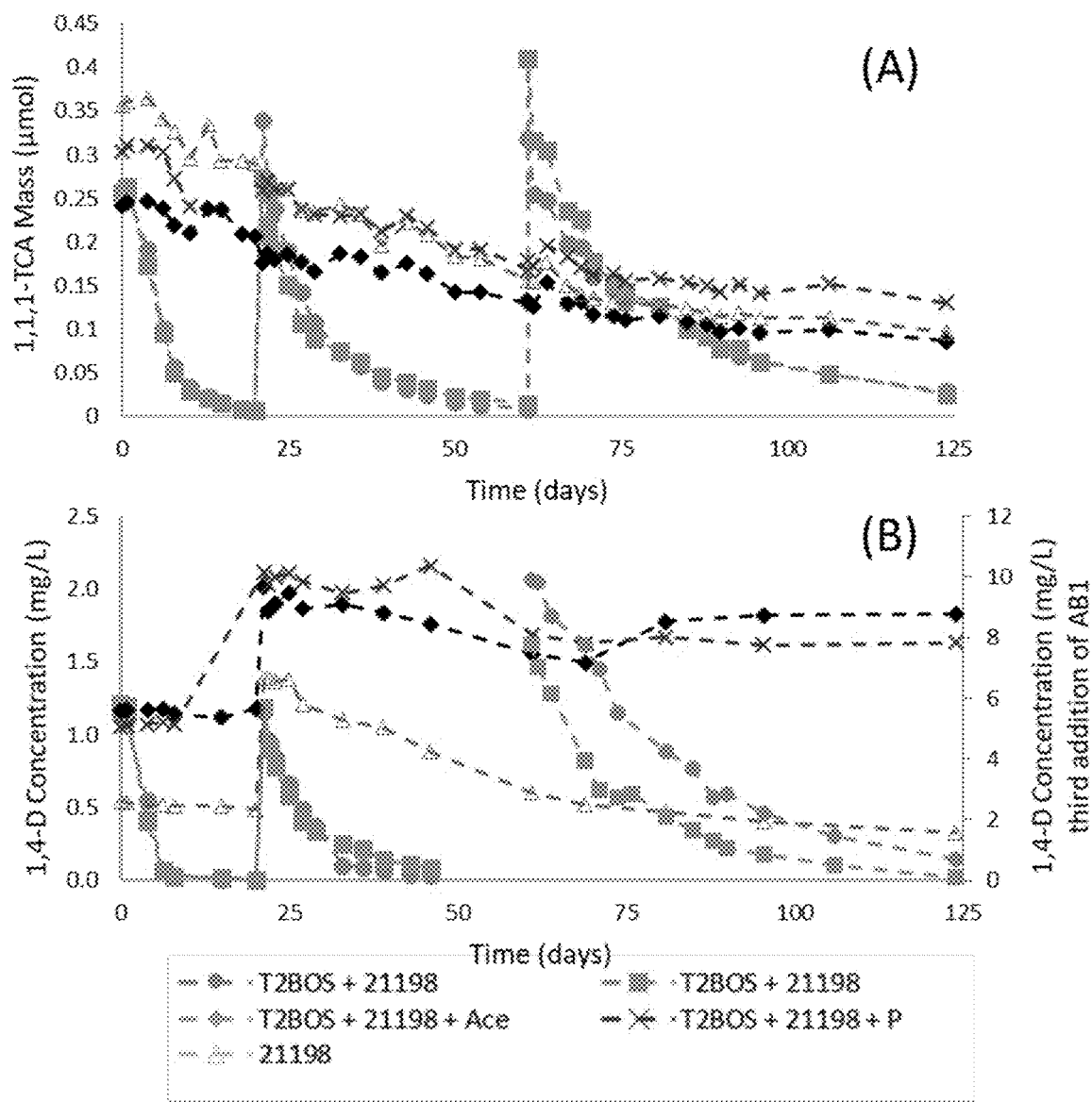
FIG. 14 illustrates 1,1-TCA (A) and 1,4-D (B) transformation during growth on 21198 on T2BOS. "Ace" is acetylene and "P" is poisoned (sodium azide). 21198 (green triangles) is the inoculum control. The third addition of 1,4-D for AB1 (blue circles) is plotted on the right vertical axis.

The concentration histories of 1,1,1-TCA and 1,4-D for the T2BOS tests are shown in FIG. 14. Three additions of 1,1,1-TCA and 1,4-D were made to the two biologically active reactors at 0, 21, and 60 days. The controls (acetylene, poisoned, and cell only) received only one addition of 1,1,1-TCA and two additions of 1,4-D. Consistent with $CO_2$ production, as an indicator of metabolic activity (FIG. 13), 1,1,1-TCA and 1,4-D were both cometabolically transformed during the first 20 days of incubation (FIG. 14). Minimal decreases in 1,1,1-TCA and 1,4-D were observed on the controls. 1,1,1-TCA and 1,4-D transformation was not observed in control that contained acetylene, indicating that SCAM was responsible for initiating their transformation. It is interesting to note the metabolic responses of $CO_2$ production and $O_2$ consumption were not inhibited by acetylene, while the cometabolic transformations were. A third addition of 1,1,1-TCA and 1,4-D was made to the active bottles around day 60. 21198 transformed the a higher concentration of 1,4-D. 21198 was able to continuous transform 1,4-D even at concentrations around 10 mg/L. The cometabolic transformation of 1,1,1-TCA and 1,4-D was maintained over a period of 125 days, with a single addition of T2BOS. Sustained metabolism over this period was indicated by the continuous production of $CO_2$ and very slow but observable rates of $O_2$ consumption (FIG. 13). 1,1,1-TCA and 1,4-D were continuously transformed, which show the continuous consumption of 2-butanol that was slowly released did not inhibit their transformation. Although the hydrolytic release of 2-butanol from T2BOS is very slow, the cometabolic transformation of 1,1,1-TCA and 1,4-D by 21198 can still be maintained over four months.

2. COC Transformation by 21198 During Growth on TBOS

The resting cell tests indicated that when 21198 was grown on 1-butanol, SCAM was not expressed. However, the resting cell kinetic tests, showed within 4 hours of resting cell exposure to 1,4-D, transformation was observed (FIG. 8) and 1,4-D was transformed at a rate in the range of 2-butanol grown cells. TBOS (tetra-butyl orthosilicate) was evaluated as an SRC that would hydrolyze to produce 1-butanol. TBOS hydrolyzes to produce 1-butanol. Based on earlier experiments with TBOS and TKEBS, which showed the branched chained TKEBS hydrolyzed more slowly, TBOS was expected to hydrolyze more rapidly than branched T2BOS, thus providing a higher rate of substrate release.

Figure 16:
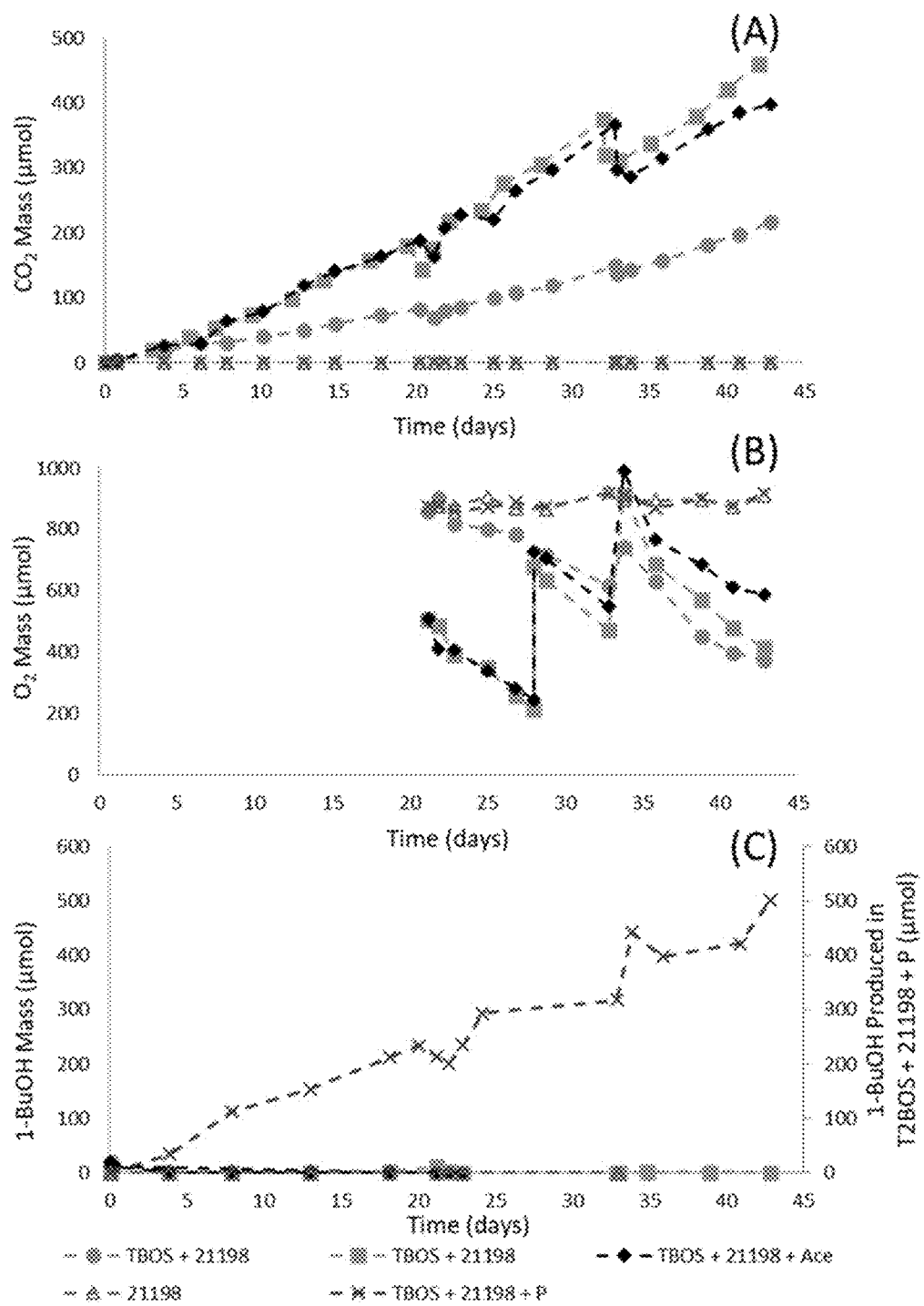
FIG. 16 illustrates production of $CO_2$ (A), consumption of $O_2$ (B) and total mass of aqueous 1-butanol (C) in batch reactors during growth on TBOS. "Ace" is acetylene. 21198 (green triangles) is the inoculum control illustrating a growth cometabolism test performed with T2BOS as an SRC.
Figure 17:
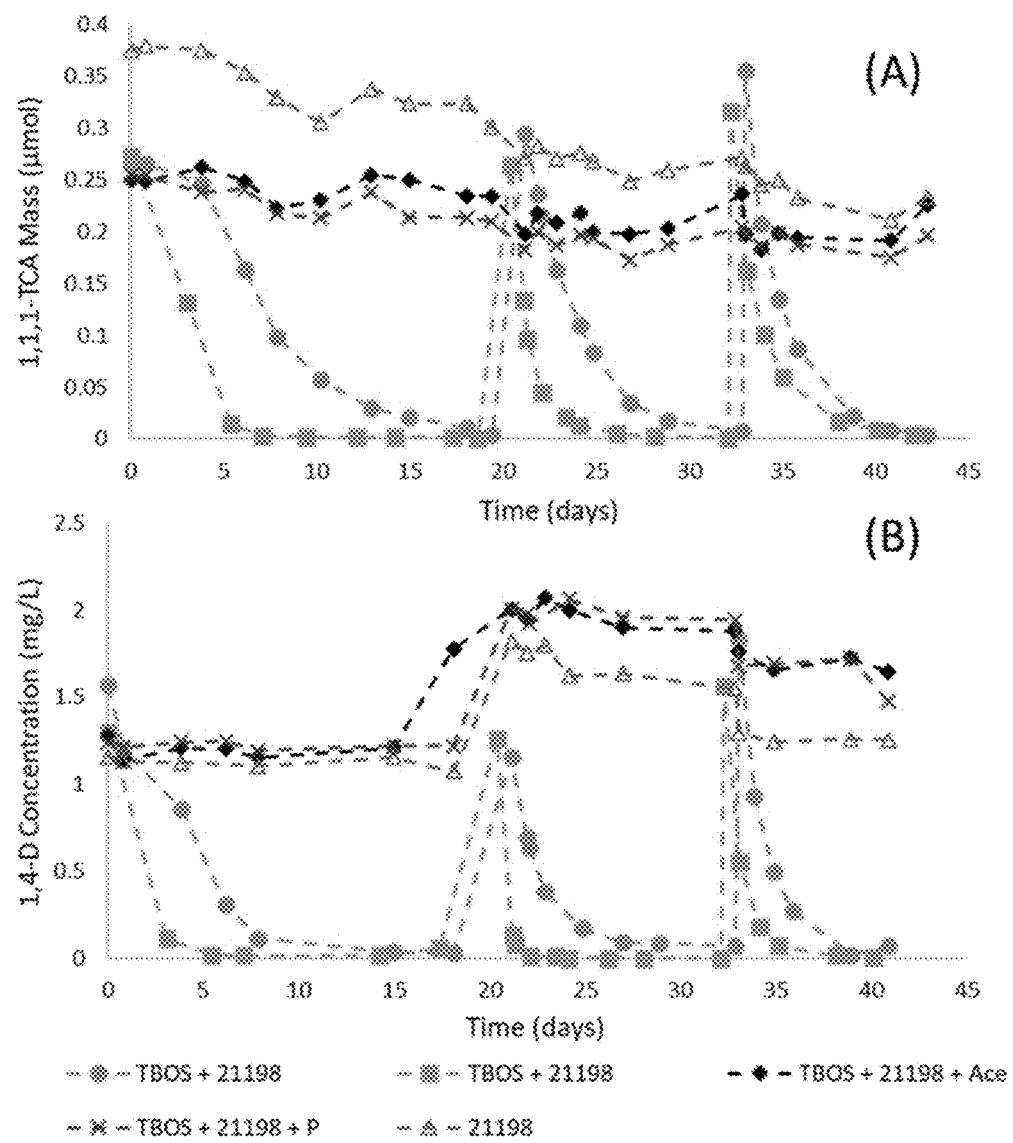
FIG. 17 illustrates 1,1,1-TCA (A) and 1,4-D (B) transformation during growth on 21198 on TBOS, where "Ace" is acetylene, "P" is poisoned (sodium azide), and 21198 (green triangles) is the inoculum control for a growth cometabolism test performed with T2BOS as an SRC.

The same growth cometabolism test performed with T2BOS as an SRC was performed for TBOS (FIGS. 16 and 17). The growth indicators for 21198 on TBOS, in the presence of 1,1,1-TCA and 1,4-D, show a much faster increase in headspace $CO_2$ (FIG. 16). Comparing 1-butanol production of the poisoned controls, the release of 1-butanol from hydrolysis was much more rapid than 2-butanol from T2BOS. A much higher utilization of $O_2$ in the TBOS reactors was observed compared to the T2BOS reactors. A buildup of 1-butanol was only observed in the poisoned control, indicating 1-butanol was rapidly consumed upon release from TBOS hydrolysis in the biologically active reactors. The acetylene control also showed similar rates of $CO_2$ production and $O_2$ consumption as the active bottles that lacked acetylene, consistent with the T2BOS results in FIG. 13.

For the active bottles, 1,1,1-TCA and 1,4-D transformation began immediately (FIG. 17). As seen in the T2BOS experiment, the batch reactors with acetylene were still able to consume the 1-butanol, but were unable to transform 1,1,1-TCA and 1,4-D, due to the inactivation of the monooxygenase. 1,1,1-TCA and 1,4-D were transformed at increasing rates with their repeated additions, indicating an increasing biomass in the reactor beads. With the slow-release hydrolysis of 1-butanol from TBOS, continuous transformation of 1,1,1-TCA and 1,4-D was observed over the 45 day period.

3. COC Transformation by 21198 During Growth on T2POS

Figure 18:
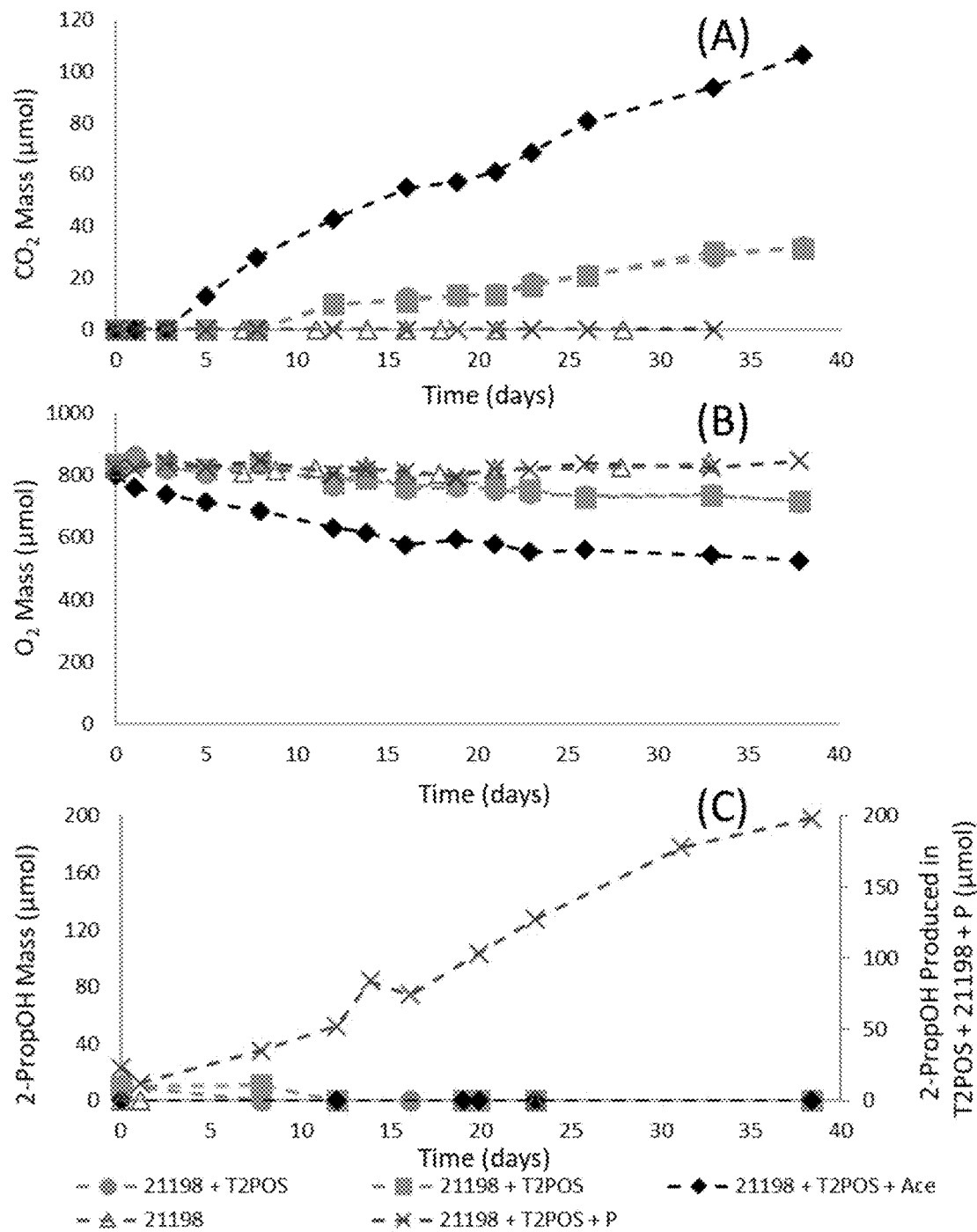
FIG. 18 illustrates production of $CO_2$ (A), Consumption of $O_2$ (B) and total mass of aqueous 2-propanol (C) in batch reactors during growth on T2POS. "Ace" is acetylene. 21198 (green triangles) is the inoculum control.

Tetraisopropoxysilane (T2POS) is a 2-propanol releasing orthosilicate, similar to TBOS and T2BOS. Linear 1-butanol was released from TBOS at roughly an order of magnitude rate more rapidly than the branched 2-butanol released from T2BOS. The smaller 2-propanol therefore would be released from T2POS more rapidly than 2-butanol from T2BOS [6], but slower than TBOS. An identical test was performed to those presented for TBOS and T2BOS. The same growth indicators, $CO_2$, $O_2$, and 2-propanol, were tracked throughout the experiment (FIG. 18). Duplicate active bottles showed very reproducible rates of $CO_2$ production and $O_2$ consumption. In the poisoned control, the 2-propanol aqueous concentration was observed to increase at a rate of 5.1 μmol/day. This rate was in between the faster rate of 1-butanol produced from TBOS (11 μmol/day) and the slower rate of 2-butanol production from T2BOS (0.76 mol/day).

Figure 19:
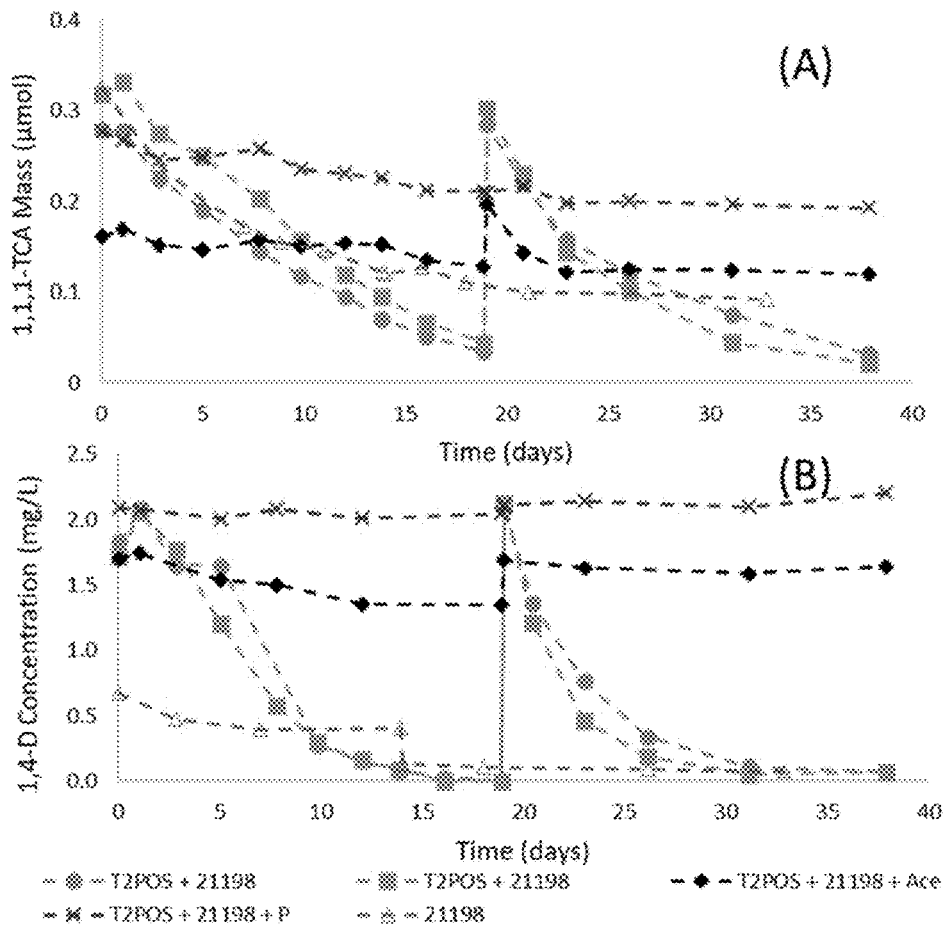
FIG. 19 illustrates 1,1,1-TCA (A) and 1,4-D (B) transformation during growth on 21198 on T2POS. "Ace" is acetylene and "P" is poisoned (sodium azide). 21198 (green triangles) is the inoculum control.

FIG. 19 shows the transformation of 1,1,1-TCA and 1,4-D through both additions of the COCs. Consistent with the TBOS and the T2BOS tests, transformation was not observed in the reactors with acetylene.

Figure 20:
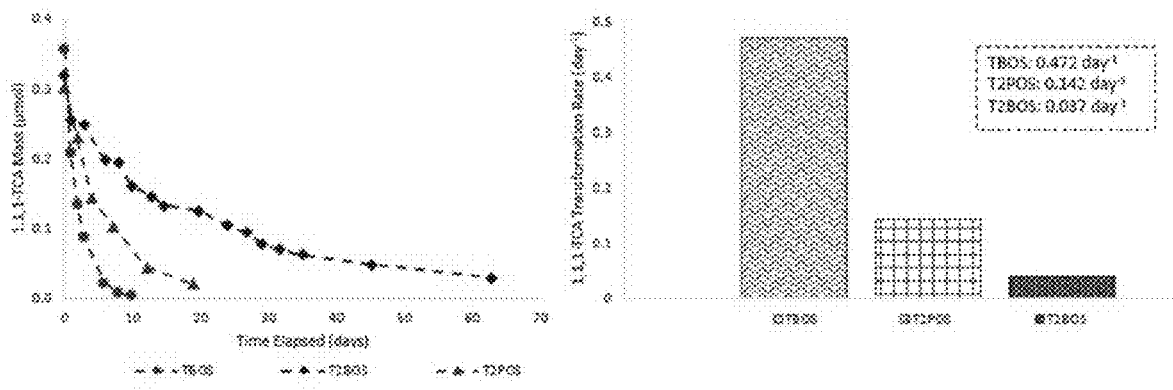
FIG. 20 illustrates transformation of 1,1,1-TCA by 21198 grown on TBOS, T2BOS, or T2POS. These rates are for 1 active bottle on the third addition for TBOS and T2BOS and on the second addition of T2POS. TBOS provides the fastest transformation rates, followed by T2POS grown 21198.
Figure 21:
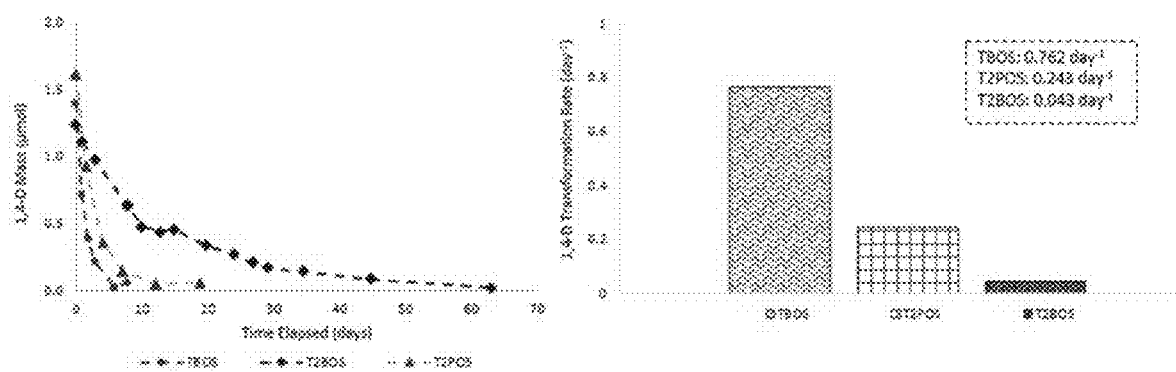
FIG. 21 illustrates transformation of 1,4-D by 21198 grown on TBOS, T2BOS, or T2POS. These rates are for 1 active bottle on the third addition for TBOS and T2BOS and on the second addition of T2POS. TBOS provides the fastest transformation rates, followed by T2POS grown 21198.

The transformation of 1,1,1-TCA and 1,4-D using each orthosilicate as an SRC is found in FIGS. 20 and 21. For both 1,1,1-TCA and 1,4-D there is a correlation in the rate of transformation to the rate of alcohol and $CO_2$ production and $O_2$ consumption. This correlation indicates that the release of alcohol from the orthosilicates and their metabolism is driving the cometabolism of these compounds. The rates of cometabolism are shown to be correlated with the rates of metabolism. The cell concentration that is being maintained is likely highest when TBOS is present and lowest when T2BOS is present as the SRC, with cometabolism rates correlated with cell concentration. The results illustrate that the molecular configuration of the group attached to the silica atom is an important design consideration for the co-encapsulation technology.

Disclosed embodiments can be used for multiple types of treatment technologies based on the technology developed. For example, the compositions and methods described herein can be used for source zone treatment. Sequencing anaerobic/aerobic treatment might be applied were the SRCs could support both anaerobic and aerobic treatment. Disclosed encapsulated compositions could be injected at the base of the low permeability zone to treat a COC mixture as it diffuses out of the low permeability zone. Oxygen could be supplied through sparging or a slow release oxygen source. Another option would be to use cometabolic sparging to add oxygen at the base of the low permeability zone.

Another embodiment concerns adding encapsulated compositions according to the present invention to recirculation wells to treat the groundwater and the base of the low permeability zone.

Certain disclosed embodiments concern treating aquifers with compositions of the present invention that include encapsulated microbes. Encapsulation prior to bioaugmentation of contaminated aquifers can improve current bioremediation techniques by providing benefits to augmented cultures including protection from toxic substances, ambient stressors like temperature and pH, and predation by protozoa. Also, encapsulation provides a method to obtain and maintain localized high cell densities, mitigate biofilm production and aquifer clogging, and increase transport distance of cells through subsurface porous media.

IX. Materials and Methods

The following examples are provided to exemplify certain features of the present invention. A person of ordinary skill in the art will appreciate that the scope of the invention is not limited to these features.

1. Chemicals

Chemicals used for studies described herein are listed below in Table 1. All chemicals used but not listed in Table 3 were reagent grade.

TABLE 3

| Compound | Abbreviations | Source | Purity |
|---|---|---|---|
| Sodium Alginate | Alginate | Spectrum Chemical | — |
| Gellan Gum | GG | C.P. Kelco | — |
| Canola oil | Canola Oil | Kroger | — |
| Iso-butane | IB | Gas Innovations | 99.99% |
| 1-Butanol | 1-butanol | Sigma Aldrich | 99.8% |
| 2-Butanol | 2-butanol | Sigma Aldrich | 99.00% |
| Tetra-butylorthosilicate | TBOS | Gelest Inc. | 97.00% |
| Tetra-s-butylorthosilicate | $T_2BOS$ | Gelest Inc. | 95.00% |
| 1,1,1-trichloroethane | 1,1,1-TCA | Tokyo Chemical Industry | 98.00% |
| Cis-dichloroethane | cDCE | Tokyo Chemical Industry | 99.00% |
| 1,4 Dioxane | 1,4-D | J.T. Baker | 99.00% |

2. Analytical Methods

1. Direct Gas Injection Gas Chromatography

All gaseous and volatile compounds (oxygen, carbon dioxide, isobutane, and chlorinated CoCs) were measured in reactors by sampling of gas headspace through septa with a 100 uL gas tight Hamilton syrtine followed by injection on a Hewlett Packard 5890 or 6890 series gas chromatograph. This information is summarized in Table 4.

Isobutane was separated within an Agilent GS-Q capillary column (30 m×0.53 mm) and a response was detected using a flame ionization detector (F(D). The developed methods used helium as the carrier gas flowing at 15 mL/minute and ran isothermally with an oven temperature of 150° C. The retention time (RT) of isobutane in the column was 0.8 minutes. Chlorinated CoCs were separated with an Agilent DB-624 US capillary column (30 m×0.53 mm) and the signal was detected using a micro-electron capture detector (ECD). The ECD operating method ran helium as the carrier gas flowing at 15 mL/minute with an isothermal oven temperature of 50° C. Using this method contaminants such as CDCE and 1,1,1-TCA were resolved and eluted at 2.0 and 2.4 minutes, respectively. Oxygen ($O_2$) and carbon dioxide ($CO_2$) signals were separated using a Sapelo 60/80 Carboxen-1000 packed stainless steel column (15 ft×⅛ inch) and detected using thermal conductivity detectors (TCD). The operating method developed for detecting $O_2$ used helium as the carrier gas flowing at 30 mL/minute and an oven temperature of 40° C., whereas, $CO_2$ detection required argon as the carrier gas and an oven temperature of 220° C.

TABLE 4

| Compound | GC Column | Detector | Carrier Gas/Flow Rate (mL/min.) | Oven Temperature ° C. |
|---|---|---|---|---|
| Oxygen | Supelco 60/80 Carboxen 1000 Stainless Steel Packed Column | TCD | Helium/30 | 40 |

TABLE 4-continued

| Compound | GC Column | Detector | Carrier Gas/Flow Rate (mL/min.) | Oven Temperature (° C.) |
|---|---|---|---|---|
| Carbon dioxide | Supelco 60/80 Carboxen 1000 Stainless Steel Packed Column | TCD | Argon/30 | 220 |
| Isobutane | Agilent GS-Q Capillary Column (30 m × 0.53 mm) | FID | Helium/15 | 150 |
| cDCE | Agilent DB-624 US Capillary Column (30 m × 0.53 mm) | ECD | Helium/15 | 50 |
| 1,1,1-TCA | Agilent DB-624 US Capillary Column (30 m × 0.53 mm) | ECD | Helium/15 | 50 |

Measured gas concentrations were used to calculate total mass in reactors via Henry's Law. The total mass was calculated by the following equation where $C_g$ is the gas phase concentration, $V_l$ is the liquid volume, and $V_g$ is the headspace volume:

$$Mass_{total} = C_g \left( \frac{V_l}{H_{cc}} + V_g \right)$$

The Henry's constant can be expended into the following equation:

$$H_{cc} = \frac{C_g}{C_l}$$

Table 5 provides Henry's constants for certain compounds that have been used in embodiments of the present invention.

TABLE 5

Henry's law constants and solubilities for isobutane, 1,4-D, and 1,1,1-TCA used in the following experiments. The Henry's Constant is dimensionless.
List of Constants

| Chemical | Henry's Constant, $H_{cc}$ | Solubility, $S_w$ (mg/L) |
|---|---|---|
| Isobutane | 49.2 | 48.9 |
| 1,4-Dioxane | 0.000198 | miscible |
| 1,1,1-Trichloroethane | 0.548 | 1,290 |

Oxygen measurements below a total mass of ~180 μmol are considered to be near zero due to a vacuum created in reactors from successive GC sampling and cellular respiration.

3. Direct Liquid Injection Gas Chromatography

Alcohols produced by LNAPL slow release compounds (SRCs), 1- and 2-butanol, were measured by sampling 1-5 uL of liquid media through reactor septa followed by direct liquid injections onto a Supelco 80/100 Carbopack-C packed column (6 ft×⅛ in.). The developed method used nitrogen as the carrier gas at a constant column pressure of 40 psi and an oven temperature of 105° C. The injection and detector port temperatures were set at 150° C. and 175° C. respectively.

LNAPL slow release compounds (SRCs) (TPOS, TBOS, and T2BOS) were quantified by liquid-liquid (dichloromethane-aqueous) extractions. In summary, reactors were vigorously shaken for 30-60 seconds to ensure adequate homogenization of LNAPL and surrounding media. Mixed liquid samples were taken through reactor septa using 1 mL liquid syringes. The sampled liquid was directly added to 1 mL dichloromethane (DCM) containing ~3000 mg/L tetra-n-propoxysilane (TPOS) as an internal standard. These samples were then vortexed for 15 minutes in 4 mL gas tight glass vials.

Immediately after vortexing, liquid DCM was separated from the aqueous sample and transferred into 2 mL gas tight glass auto-sampler vials with rubber septa. Vials were loaded onto a 100-sample Hewlett Packard HP 6890 Series auto-sampler that automatically injected 5 uL DCM liquid samples onto a HP 6890 series GC. The GC was equipped with a Restek RTX-20 capillary column (I 5 m×0.53 um) and an FID detector. The developed method used helium as the carrier gas flowing at 12 mL/minute with an initial oven temperature of 100° C. The initial temperature washed for one minute followed by a 35° C./minute temperature ramp to 220° C. which was held to a final run time of five minutes. DCM, TPOS, T2BOS, and TBOS peaks were all resolved using this method at RTs of 0.8, 3.2, 3.9, and 4.3 minutes, respectively. Aqueous concentration measurements were converted to total mass in reactors and reported as total mass herein.

4. Heated Purge and Trap Gas Chromatography Mass Spectrophotometry

Due to the relatively low vapor pressure of 1,4-D a Tekmar Dohrmann 3100 heated purge and trap was used to volatilize and concentrate liquid samples. Purging of aqueous phase 1,4-D from 5 mL liquid samples was done by heating samples to 80° C. for 20 minutes while bubbling nitrogen through samples at 20 mL/min. The vapor phase 1,4-D that is purged from the liquid is swept through a three-sorbent-bed trap where it is trapped. The trap is then headed and flushed with helium to desorb the 1,4-D. The concentrated gas was then injected into a HP 6890 series GC and 1,4-D was separated using a Restek Rtx-VMS column (30 m×0.2 mm) and a signal was detected using a 5973 Mass Selective Detector. Deuterated 1,4-D was used as an internal standard at a concentration of 5 ppb and peaks were detected and resolved by the MS analyzing for mass to charge ratios, both peaks eluted at 7.1 minutes.

5. Culture Growth, Storage, and Quantification

ATCC 21198 was maintained on minimal salts media (MSM) agar plates. ATCC 21198 culture plates were stored at 30° C. in 3.5 L gas tight jars, autoclaved prior to use. The headspace of the jars was kept at a slight positive pressure by adding 45 mL pure isobutane (IB), as the carbon source IB was refreshed each time the containers were opened to the atmosphere maintaining headspace IB levels of 1.25% (v/v). For experimentation, biomass was grown by inoculating sterile 300 mL pH-7 phosphate buffered MSM in 710 mL glass Wheaton bottles with a group of colonies from the agar storage plates. Ingredients of phosphate and carbonate MSM are provided in Table 6. The Wheaton bottles were scaled with a reusable screw on cap fitted with gray butyl rubber septa. New storage plates were created after about 70 percent of the colonies were used.

TABLE 6

ATCC 21 I 98 mineral salts media growth-solution ingredient list

| Compound | Phosphate MSM Concentrations | Carbonate MSM Concentrations | Unit |
|---|---|---|---|
| NH4Cl | 2.000 | 2.000 | g/L |
| MgCl2*6H20 | 0.075 | 0.075 | g/L |

TABLE 6-continued

ATCC 21 I 98 mineral salts media growth-solution ingredient list

| Compound | Phosphate MSM Concentrations | Carbonate MSM Concentrations | Unit |
|---|---|---|---|
| (NH4)2S04 | 0.100 | 0.100 | g/L |
| EDTA | 0.010 | 0.010 | g/L |
| ZnS04*7H20 | 4.40E-03 | 4.40E-03 | g/L |
| CaCl2 | 0.001 | 6.01E-01 | g/L |
| MnCl2*4H20 | 1.00IE-03 | 1.0IE-03 | g/L |
| FeS04*7H20 | 1.00E-03 | 1.00E-03 | g/L |
| (NH4)6Mo7O 24*4H20 | 2.20E-04 | 2.20E-04 | g/L |
| CuS04*5H20 | 3.0IE-04 | 3.0IE-04 | g/L |
| CoCl2*6H20 | 3.42E-04 | 3.42E-04 | g/L |
| NaHC03 |  | 1.3427616 | g/L |
| K2HP04 | L55 |  | g/L |
| NaH2P04 | 0.85 |  | g/L |
| pH |  | 7 |  |
| Estimated Ionic Strength | 0.040 | 0.043 | mol/L |

Additions of isobutane as a primary growth substrate were made to growth bottles through the septa Electron-donor equivalent masses of IB were added such that the oxygen in the 410 mL air headspace could oxidize two thirds of the added substrate; this was done to ensure a constant substrate rich growth environment. An initial addition of IB was made at growth reactor setup followed by 4 days of shaking at 200 rpm on a rotary shaker table in a 30° C. temperature controlled room. After initial growth, the reactors received a headspace air, oxygen, refresh by removing the cap and allowing to set in a laminar flow hood for 10 minutes. Caps were replaced and a second spike of IB was added. After another 24 hours on the shaker table, the cultures were at peak exponential growth phase and ready to be harvested and used for experimentation. Cells were harvested by centrifugation at 15,000 G for 10 minutes followed by washing and re-suspension in 50 mM pH-7 phosphate buffer. All cells were streaked on a non-specific tryptic-soy growth agar to ensure purity prior to experimental use Cells were typically used in experiments the day of harvesting; however, occasionally cells were used 4 days after harvesting. In these cases, cells were stored in phosphate buffer at 4° C. All cell mass values reported are based on total suspended solids (TSS) analysis of harvested cultures. The TSS of concentrated cells was quantified via vacuum filtration of a known volume of cells through an Advantec 0.45 um mixed cellulose-ester membrane filter and drying at 105° C. for 30 minutes.

Example 1

This example concerns an embodiment of microbial encapsulation using alginate encapsulation. External cross-linking methods for the successful encapsulation of *Rhodococcus rhodochrous* ATCC 21198 in stable alginate macro spheres, 2 mm in diameter, were adapted from the literature. A 2% stock of alginate pre-gel solution was created by hydrating alginate powder in heated 200 mL Nanopure water. Nanopure water was heated to 85° C. on a hot plate while being constantly mixed with a magnetic stir bar. When the liquid reached 85° C., an addition of sodium alginate powder was made to achieve a final concentration of 2% (w/w) alginate. The pre-gel solution was mixed for 30 minutes to ensure complete hydration, followed by autoclaving at 121° C. for 15 minutes to degas and ensure the final pre-gel solution was sterile. The pre-gel solution was allowed to cool to room temperature prior to use for encapsulation. Typically, alginate pre-gel solution was used for experimentation the day of creation, but on occasion was used up to four days later. Pre-gel solution was stored at room temperature in a gas tight jar.

For microbial encapsulation, a known volume of room temperature pre-gel solution was transferred to a 50 mL Falcon tube and the pH was adjusted to seven. Adjustment of pH was done by making additions of dilute hydrochloric acid (HCl) or by a single addition of concentrated pH-7 phosphate buffer to achieve a final concentration of 4 mM total phosphate. In either case, the volume of liquid added to correct for pH changed the final volume less than 1%. After the pH was adjusted, a known volume of concentrated cell slurry suspended in 50 mM phosphate buffer was added to the alginate pre-gel solution and vortexed for 30 seconds. Cell masses were added to obtain a desired final cell concentration in beads, reported throughout herein as mg cells as TSS per gram of bead ($mg_{TSS}/g_{bead}$).

Following the addition of cells, the pre-gel solution was transferred to 5-20 mL Luer lock liquid syringes fitted with a 25 gauge×1 inch needle. The pre-gel solution was then extruded into 900 mL of 0.25-1% calcium chloride (CaCl) solution from a distance of 2-5 cm above liquid surface. CaCl solution was continuously mixed with a magnetic stir plate at 150-250 rpm. The beads were allowed to crosslink for a total of 60 minutes, measured from the time that the last bead was formed.

Microbially active macro-beads were separated from the crosslinking solution via filtration using a vacuum pump fitted with a 70 mm plastic filter funnel. The filtered beads were washed three times with pH-7 carbonate buffered MSM and dried a final time using a vacuum pump. The final mass of beads was measured with minimal exogenous liquid and an assumption was made that all cells added to pre-gel solution were encapsulated. Using the known mass of cells added and the measured final mass of beads created a cell mass loading calculated as $mg_{TSS}/g_{bead}$. Typically, microbially active beads were used for experimentation the day they were made; however, on occasion beads were stored overnight in pH-7 carbonate buffered MSM at 4° C.

Example 2

This example concerns an embodiment of microbial encapsulation using gellan gum encapsulation. Gellan gum pre-gel stock solution was made in a 200 mL volume of autoclaved 2 mM pH-7 phosphate buffered Nanopure water in a 250 mL Pyrex glass bottle. Gellan gum powder was added immediately after removing the solution from the autoclave to achieve a concentration of 0.75% (w/v). The pre-gel solution was shaken vigorously for 30 seconds and placed on a heated magnetic stir plate keeping the solution at ~85° C. while mixing at 200 rpm for 30 minutes. After complete hydration of gellan gum powder, a known volume of pre-gel solution was transferred to a 50 mL Falcon tube. To initiate gelation an appropriate volume of 10% CaCl stock solution was added to make a final concentration of 0.06% (w/v). The Falcon tube lid was replaced and the solution was vortexed for 30 seconds. The pre-gel solution was then left at room temperature to cool to 60° C. at which time the pH was adjusted to seven with dilute NaOH, if necessary. The pre-gel solution was again left at room temperature to cool to ~45'C before adding a known volume of concentrated cell slurry that was suspended in S0 mM phosphate buffer. At this point, the pre-gel solution was finalized and ready for complete gelation.

To form gellan gum microspheres the pre-gel solution was added directly to an appropriate amount of heated canola oil, at ~45° C. to achieve a disperse phase volume fraction of 0.15. To increase emulsion stability Span-80 was added at 0.1% (v/v) and the entire solution was transferred to a 125 mL wide-mouth glass beaker. The canola oil and pre-gel solution were then mixed with an IKA RW-20 digital overhead impeller mixer at 2500 rpm for 10 minutes. The impeller blade was ~5 cm in diameter and was positioned ⅓ the way up from the bottom of the vial to the top of the liquid mixture.

Figure 22:
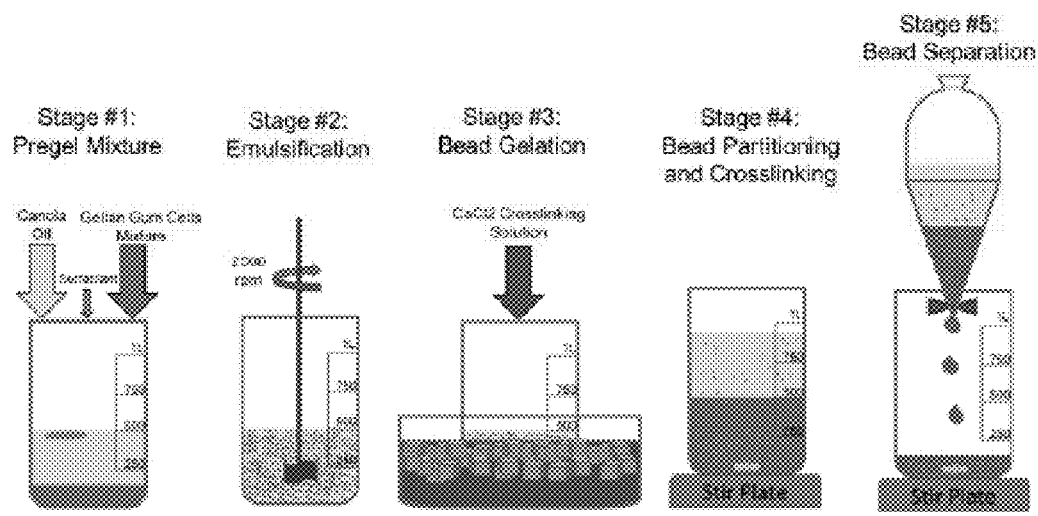
FIG. 22 is a graphical representation of the method developed for the generation of gellan gum microspheres though a gellan gum emulsification internal gelation method.

To force gelation of emulsified gellan gum droplets, the emulsified solution was transferred to an ice bath and cooled until the solution reached a temperature of 15° C. The canola oil and micro-bead mixture was stirred slowly at room temperature for 90 minutes to begin separation of micro-beads from canola oil. The mixture was then transferred to a 1 L beaker containing 500 mL of 0.25% (w/v) CaCl solution to allow beads to partition into the aqueous phase and increase bead stability (FIG. 22, Stage 4). A large portion of canola oil was removed by aspiration. However, a separatory funnel was necessary to achieve complete separation (FIG. 22, Stage 5). Micro-beads were removed from the CaCl solution using a vacuum pump fitted with a 1.2 urn glass fiber filter and washed repeatedly with pH-7 carbonate buffered MSM. To calculate the final mass loading of cells in beads as mgT/gbead, assumptions were made that 1 mL of pre-gel solution would form 1 g of beads and that all cells added were encapsulated. Typically, microbially active beads were used for experimentation the day they were made, however, on occasion beads were stored overnight in a pH-7 carbonate buffered MSM at 4° C.

Micro-beads made using the above method ranged in size from ~10-100 μm in diameter, as determined through repeated bright field images taken with a Leica DM 2500 benchtop microscope.

Example 3

This example concerns an embodiment of method to encapsulate ATCC 21198 in gellan gum macro-beads. The method developed creates cylindrical macro-beads. The detailed method presented below is a summary of the optimized gellan gum macro-encapsulation method.

The preparation of gellan gum pre-gel solution followed the same procedure as the above procedure to the point just before gellan gum emulsification in canola oil. In summary, a 0.75% (w/v) gellan gum pre-gel solution was prepared in autoclaved ~2 mM pH-7 phosphate buffered nanopure water at ~85° C. A CaCl solution was added to the pre-gel solution to a final concentration of 0.06% (w/v) CaCl. The solution was allowed to cool to ~60° C. and the pH was adjusted to seven. The solution was then cooled to ~45° C. and cells were added. At this point the pre-gel solution was finalized and ready for gelation.

To create macro-beads from the warm pre-gel solution a 60 mL plastic syringe was used to draw the solution into an attached 1.5 meter section of flexible rubber tubing with an inner diameter of ~2 mm. Once the tubing was filled with pre-gel solution, it was coiled and set on ice to cool to ~15° C. to finish gelation and completely solidify all gel within the tubing. After cooling to ~15° C. the gel-filled tubing was placed in a laminar flow hood for 60 minutes to provide extra time for internal crosslinking prior to extrusion of thin cylindrical sections of gel from the tubing. In the laminar flow hood, the hardened gellan gum was pushed from the tubing onto longsections of Parafilm using the attached 60 mL syringe filled with air or a buffer solution. The extruded sections of hardened gellan gum were ~2 mm in diameter by ~15-30 cm in length. A razor blade was used to cut the long sections into ~2 mm sections such that the height of each cylinder was approximately the same as the diameter.

At this point, the cylinders were allowed to cure for 10 minutes in the laminar flow hood before being transferred to a 1 L beaker containing 500 mL of 0.25% (w/v) CaCl$_2$ solution for 60 minutes. Microbially active macro-beads were separated from the external crosslinking solution using a vacuum pump fitted with a 70 mm plastic filter funnel. The filtered beads were washed three times with pH-7 carbonate buffered MSM and dried a final time using the vacuum pump. The final mass of beads was measured with minimal exogenous liquid and an assumption was made that all cells added to pre-gel solution were encapsulated. To calculate the final mass loading of cells in beads as mg$_{Tss}$/gbead, assumptions were made that 1 mL of pre-gel solution would form 1 g of beads and that all cells added were encapsulated. Typically, microbially active beads were used for experimentation the day they were made; however, on occasion beads were stored overnight in pH-7 carbonate buffered MSM at 4° C.

Example 4

This example concerns an embodiment of a method for encapsulating slow release compounds in alginate. Alginate was added to warm Nanopure water and mixed for 30 minutes to complete hydration, and was then autoclaved. After removing the alginate pre-gel solution from the autoclave a known amount, typically around 40-50 mL, was transferred to a 125 mL wide mouth glass vial and allowed to cool to ~70° C.

After the solution cooled, Span-80 emulsifier was added to achieve a concentration of 0.1% (v/v). A known volume of LNAPL SRC was added to the pre-gel solution and the mixture was emulsified using an IKA RW 20 digital overhead impeller mixer at 2500 rpm for 10 minutes. Following emulsification, the pre-gel solution was transferred to a 50 mL Falcon tube and allowed to cool to ~45° C. The pH was then adjusted to seven by addition of pH-7 phosphate buffer to achieve a final concentration of 4 mM total phosphate. If co-encapsulation of cells was desired a known volume of concentrated cell slurry suspended in 50 mM phosphate buffer was added at this point to the SRC containing alginate pre-gel solution and vortexed for 30 seconds. Following the addition of cells or just after pH adjustment, the emulsified pre-gel solution was transferred to 5-20 mL liquid syringes fitted with a 25 gauge×1 inch needle. The pre-gel solution was then extruded into 900 mL of 0.25% (w/v) CaCl$_2$ solution from a distance of 2-5 cm above liquid surface. CaCl$_2$ solution was continuously mixed with a magnetic stir plate at 150-250 rpm. The beads were allowed to crosslink for a total of 60 minutes measured from the time that the last bead was formed.

Macro-beads containing SRCs were separated from the crosslinking solution using a vacuum pump fitted with a 70 mm plastic filter funnel. The beads were washed three times with a 0.1% (v/v) Tween-80 sterile microbe safe soap wash to rinse any exogenous SRCs from their surface. This was followed by rinsing three times with pH-7 carbonate buffered MSM and dried a final time using the vacuum pump. The final mass of beads was measured with minimal exogenous liquid and an assumption was made that all cells added to pre-gel solution were encapsulated. Using the known mass of cells added, and the measured final mass of beads create a cell mass loading was calculated as mg$_{Tss}$/gbead. Typically, microbially active beads were used for experimentation the day they were made; however, on occasion beads were stored overnight in pH-7 carbonate buffered MSM at 4° C.

To determine the SRC mass loading in beads as $mg_{SRC}/g_{bead}$ and encapsulation efficiency of this process, two ~0.25 g samples of beads were taken and transferred into 27 mL vials containing 10 mL of 2 mM sodium citrate solution. These vials were placed on a shaker table shaking at 250 rpm for 90 minutes. Sodium citrate solution was used to chelate calcium and help break apart the alginate spheres such that any encapsulated SRC was released into solution. The amount of released SRC was quantified using a DCM extraction method with GC analysis of the extract. Using the measured mass of SRC released and the known initial mass of beads broken down a mass loading could be determined ($mg_{SRC}/g_{bead}$). The process encapsulation efficiency, the percent of added SRC that was successfully encapsulated, was then determined from the measured mass loading ($mg_{SRC}/g_{bead}$), the measured final mass of beads ($g_{bead}$), and the known mass of SRC added.

Example 5

This example concerns an embodiment of a method for encapsulating LNAPL SRCs in gellan gum macro-beads. Gellan gum pre-gel stock solution was made in a 200 mL volume of autoclaved 2 mM pH-7 phosphate buffered nanopure in a 250 mL Pyrex glass bottle. Gellan gum powder was added immediately after removing the solution from the autoclave to achieve a concentration of 0.75% (w/v). The pre-gel solution was shaken vigorously for 30 seconds and placed on a heated magnetic stir plate keeping the solution at ~85° C. while mixing at 200 rpm for 30 minutes. After complete hydration of gellan gum powder, a known volume of warm pre-gel solution, typically 40-50 mL, was transferred to a 125 mL wide mouth glass vial. Span-80 emulsifier was added to achieve a concentration of 0.1% (v/v). A known volume of LNAPL SRC was then added to the pre-gel solution and the mixture was emulsified using an IKA RW 20 digital overhead impeller mixer at 2500 rpm for 10 minutes. Following emulsification, the pre-gel solution was heated back to ~80° C. and transferred to a 50 mL Falcon tube. To initiate gelation an appropriate volume of 10% $CaCl_2$ stock solution was added to make a final concentration of 0.06% w/v. The Falcon tube lid was replaced and the solution was vortexed for 30 seconds. The pre-gel solution was then left at room temperature to cool to ~60'C before the pH was adjusted to seven with dilute NaOH, if necessary.

If co-encapsulation of cells was desired, the pre-gel solution was again left at room temperature to cool to ~45° C. before adding a known volume of concentrated cell slurry that was suspended in 50 mM phosphate buffer. At this point, the pre-gel solution was finalized and ready for complete gelation.

To create macro-beads from the warm pre-gel solution a 60 mL plastic syringe was used to draw the emulsified SRC containing pre-gel solution from the Falcon tube into an attached 1.5 m section of flexible rubber tubing with an inner diameter of ~2 mm. Once the tubing was filled with pre-gel solution, it was coiled and set on ice to cool to ~15° C. to finish gelation and completely solidify all gel within the tubing. After cooling to ~15° C. the gel filled tubing was placed in a laminar flow hood for 60 minutes to provide extra time for internal crosslinking prior to extrusion of thin cylindrical sections of gel from the tubing. In the laminar flow hood, the hardened gellan gum was pushed from the tubing onto long sections of Parafilm using the attached 60 mL syringe filled with air or a buffer solution. The extruded sections of hardened gellan gum were ~2 mm in diameter by ~15-30 cm in length. A razor blade was used to cut the long sections into ~2 mm sections such that the height of each cylinder was approximately the same as the diameter.

The cylinders were allowed to cure for 10 minutes in the laminar flow hood before being transferred to 1 L beaker containing 500 mL of 0.25% (w/v) $CaCl_2$ solution for 60 minutes. Microbially active macro-beads were separated from the external crosslinking solution using a vacuum pump fitted with a 70 mm plastic filter funnel. To rinse any, exogenous SRCs from the surface of beads they were washed three times with a 0.1% (v/v) Tween-80 sterile microbe safe soap wash. Followed by rinsing three times with pH-7 carbonate buffered MSM and dried a final time using the vacuum pump. The final mass of beads was measured with minimal exogenous liquid and an assumption was made that all cells added to pre-gel solution were encapsulated. To calculate the final mass loading of cells in beads as $mg_{Tss}/g_{bead}$, assumptions were made that 1 mL of pre-gel solution would form 1 g of beads and that all cells added were encapsulated. Typically, microbially active beads were us d for experimentation the day they were made, however, on occasion beads were stored overnight in pH-7 carbonate buffered MSM at 4° C.

To determine the SRC mass loading in beads as $g_{SRC}/d_{bead}$ and encapsulation efficiency of this process, two ~0.25 g samples of beads were taken and transferred into 27 mL vials containing 10 mL of 2 mM sodium citrate solution. These vials were heated to ~80° C. then placed on a shaker table shaking at 250 rpm for 120 minutes. Sodium citrate was used to chelate calcium and help break apart the gellan gum cylinders such that any encapsulated SRC was released into solution. Due to the increased stability of gellan gum cylinders over alginate macrospheres, heating and excess physical agitation of gellan gum cylinders was required to ensure all encapsulated SRC was released.

The amount of released SRC was quantified using the DCM extraction method. Using the measured mass of SRC released and the known initial mass of beads broken down a mass loading could be determined. The process encapsulation efficiency, the percent of added SRC that was successfully encapsulated, was then determined from the measured mass loading ($g_{SRC}/g_{bead}$), the measured final mass of beads ($g_{bead}$), and the known mass of SRC added.

Example 6

This example concerns short-term primary substrate utilization tests, that often lasted less than 24 hours, were used to determine the immediate effect encapsulation had on cell viability. These batch reactor tests were conducted at a constant 20° C. in glass 27 mL crimp top vials sealed with gray butyl rubber septa. Ten mL of pH-7 carbonate buffered MSM was added to each sterile vial followed by an addition of a known mass of suspended, encapsulated, or co-encapsulated ATCC 21198, ranging from 0.5-5 mg cells as TSS. The determined encapsulated cell mass loadings as $g_{TSS}/g_{bead}$ were used to calculate the necessary mass of beads to add to each reactor. For ease of comparison, attempts were made to keep the total suspended and encapsulated cell masses added to each reactor the same between each experiment.

Following addition of cells, septa were added and crimped in place to seal vials. Pure isobutane gas was provided as the primary substrate through the septa using a plastic 1 mL Luer Lock syringe. Typically, ~8 μmol of IB was added to each vial. Vials were shaken rapidly on a rotary shaker table at 200 rpm to ensure constant equilibration of added IB. The assumption was made that cellular utilization rates of IB were slower than the diffusion rate of IB into solution such that equilibrium between the liquid and gas phase of IB was constantly maintained and measured gas concentrations could be used to predict liquid concentrations and total mass of IB in reactors, through Henry's law.

IB gas concentrations were monitored using GC methods and the total mass of IB remaining in each reactor was calculated using Henry's Law. Dependent on the mass of cells added and the rate at which IB was being consumed, IB concentrations were monitored every 20-60 minutes to develop a defined cellular IB utilization curve. Substrate utilization rates were calculated through linear regression of the collected IB mass data and normalized to the cell mass added to each reactor. Substrate utilization rates were presented as, $\mu mol_{IB}/day\text{-}mg_{Tss}$. Suspended cell IB utilization rates were used as a benchmark to assess the effect encapsulation had on cellular viability.

In each test, abiotic reactors were used to ensure disappearance of IB was related to cellular utilization. Also, kinetic testing was conducted with duplicate or triplicate reactors to ensure reliable and repeatable data sets.

Example 7

This example concerns batch kinetic reactors that were used to evaluate the long-term, weeks to months, remediation performance of suspended, encapsulated, and co-encapsulated cells. These batch kinetic tests were conducted at a constant 20° C. in 155-310 mL glass Wheaton bottles sealed with reusable screw on caps fitted with gray butyl rubber septa. Reactors were filled with 100-200 mL of pH-7 carbonate buffered MSM followed by an addition of suspended, encapsulated, or co-encapsulated cells to achieve an initial cell mass concentration of 10 mg/L as TSS. Encapsulated bead cell mass loadings as $g_{TSS}/g_{bead}$ were used to calculate the necessary mass of beads to add to each reactor. For ease of comparison and attempt was made to keep all encapsulated cell mass loadings at 0.5 $g_{TSS}/g_{bead}$ and the total suspended and encapsulated cell mass added to each reactor between each experiment was kept constant at ~10 mg/L. A mixture of 1,1,1-TCA, cis-DCE, and 1,4-D was evaluated at aqueous concentrations ranging from ~250-1000 ppb. Reactors were monitored over a period of 260 days for respiration data ($O_2$ and $CO_2$), substrate data (alcohols), and contaminants (1,1,1-TCA, cis-DCE, and 1,4-D) according to methods previously described.

Abiotic controls were used to ensure transformation of CoC mixtures was biotic. Also, to monitor the potential mass of substrate being released from encapsulated SRCs, long-term reactors that mimicked active co-encapsulated cell reactors were created, then poisoned with 2% (w/v) sodium azide to ensure cells would not consume the hydrolysis byproducts, 1- or 2-butanol, of added SRCs. These bottles were not spiked with contaminants but were monitored for respiration and substrate data to determine an experimental hydrolysis rate of substrates.

Due to mixtures being frequently observed at contaminated sites one disclosed embodiment focused on the bioremediation potential of ATCC 21198 to transform a mixture of 1,1,1-TCA, cDCE, and 1,4-D. All reactors in all of the transformation experiments presented below received initial and/or successive spikes of environmentally relevant concentrations of each contaminant ~250-1000) ppb. CAHs were added via additions of saturated Nanopure liquid solutions through reactor septa and 1,4-D was added by dilution of a 1000 ppm stock solution.

Reactors were monitored over a period of ~30-260 days for respiration data ($O_2/CO_2$), substrate data (SRC/alcohols), and contaminant data (1,1,1-TCA, cDCE, and 1,4-D) according to methods presented. Abiotic controls were used to ensure transformation of CoC mixtures was biotic. Also, to monitor the potential mass of substrate being released from encapsulated SRCs, long-term reactors that mimicked active co-encapsulated cell reactors were created, then poisoned with 2% (w/v) sodium azide to ensure cells would not consume the hydrolysis byproducts, 1- or 2-butanol, of added SRCs. These bottles were not spiked with contaminants but were monitored for respiration and substrate data to determine an experimental hydrolysis rate of substrates.

Example 8

This example concerns abiotic hydrolysis experiments. Batch reactors similar to the CoC transformation reactors were used to determine the rate of hydrolysis of TBOS and T2BOS free suspended in solution and encapsulated at different mass loadings in both alginate and gellan gum. These batch kinetic tests were conducted at a constant 20° C. in 155 mL glass Wheaton bottles sealed with reusable screw on caps fitted with gray butyl rubber septa. Reactors were filled with 100 mL of pH-7 carbonate buffered MSM followed by an addition of free suspended or encapsulated SRCs. The total mass of SRC added to each reactor was dependent on various parameters but ranged from 1000-1500 mg/L. All hydrolysis rates observed here were abiotic hydrolysis rates, which was ensured by the addition of 0.2% (w/v) sodium azide as a microbial poison and typically measurements of respiration data ($O_2/CO_2$).

One aspect of the present disclosure was to establish that if a microbial agent, such as ATCC 21198, was co-encapsulated with SRCs, that the encapsulated microbial population consumes substrates as they are produced within beads, and the energy gained by cells from the consumption of SRC products will extend the duration of co-metabolic transformation and increase the total mass of CoCs an initial population of ATCC 21198 can degrade.

1- and 2-butanol were used as growth substrates for ATCC 21198. Growth occurred on both alcohols; however, results suggested that no immediate induction of co-metabolic enzymes occurred with growth on 1-butanol, but induction was observed with growth on 2-butanol. Though induction of co-metabolic monooxygenase enzymes was observed ATCC 21198 when grown on the branched alcohol, 2-butanol, the degree of induction was lesser than ATCC 21198 grown on the primary substrate isobutane (IB).

Example 9

This example concerns an embodiment of microbial encapsulation. Short-term isobutane utilization tests were used to determine the impact of encapsulation in hydrogel beads on ATCC 21198. Reactors containing a similar mass of suspended or encapsulated biomass were created and an addition of IB was made to each reactor. The disappearance of IB was monitored over time and utilization rates were calculated via linear regression of the measured decrease in IB mass over time, presented as ($\mu mol_{IB}/day\text{-}mg_{TSS}$). Suspended cell utilization rates were measured during each experiment due to possible differences in utilization rates between different growth batches of cells. Measured suspended cell rates were used as a benchmark to assess the effects of encapsulation on a particular batch of cells. Reactors were created in duplicate or triplicate to ensure repeatable data and abiotic controls were used to ensure the disappearance of isobutane was related to added biomass.

Example 10

Figure 23:
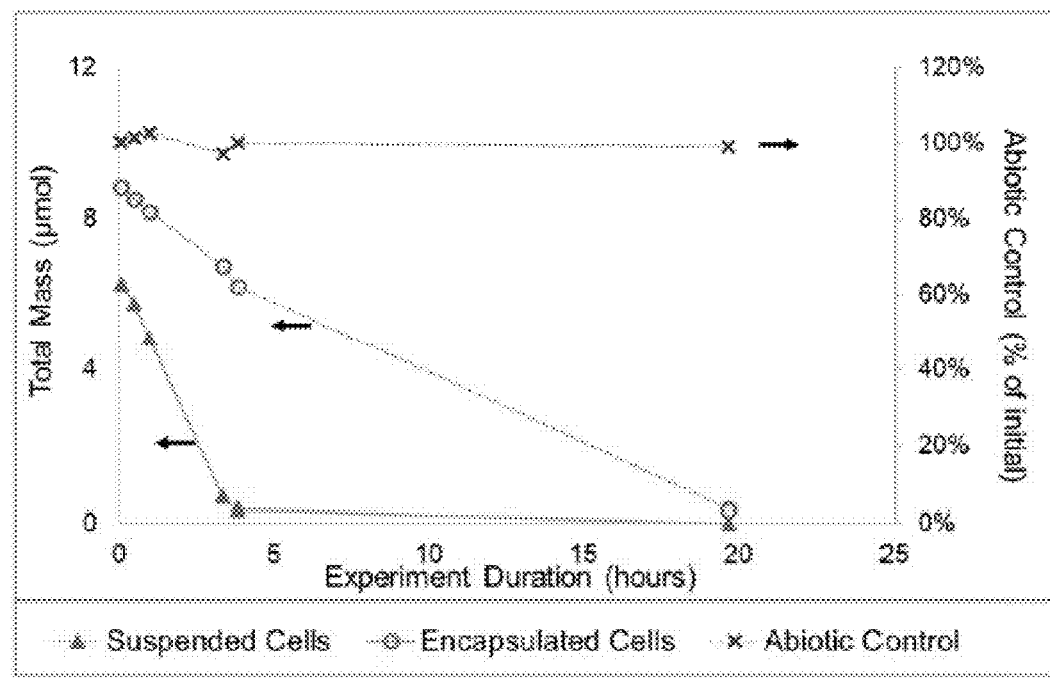
FIG. 23 is a graph of total mass (µmol) versus time illustrating an isobutane utilization curve measured for ATCC 21198 suspended in media and encapsulated in alginate.

This example concerns an embodiment of microbial encapsulation using alginate encapsulation of ATCC 21198. A 2% (w/v) pre-gel alginate solution was made followed by an addition of a known mass of concentrated cells suspended in phosphate buffer. The pre-gel solution was then extruded into a 1% (w/v) $CaCl_2$ crosslinking solution. Encapsulation of ATCC 21198 in alginate with this initial recommended method, produced stable macro-beads, ~2.5 mm in diameter, but cellular 113B utilization rates were reduced by ~60% after encapsulation. (FIG. 23 (Table 7).

TABLE 7

| Treatment | Calculated ID Utilization Rate ($\mu$mol/day/$mg_{TSS}$) | Percent Difference from Suspended |
|---|---|---|
| Suspended Cells | 17 | |
| Alginate Encapsulated Cells | 6.4 | −62.6% |

Despite the fact that encapsulated cells consumed IB at reduced rates, these results provided positive evidence that ATCC 21198 could be encapsulated and maintain substrate utilization activity. It was expected that encapsulation would reduce utilization rates due to possible reduction of cell access to substrates from diffusion limitations, though this significant of a decrease was not expected. To investigate the observed activity loss further several encapsulation method parameters, such as the ionic strength and concentration of alginate pre-gel solution, $CaCl_2$ crosslinking concentrations, and $CaCl_2$ crosslinking durations; were altered incrementally in subsequent experiments.

Figure 24:
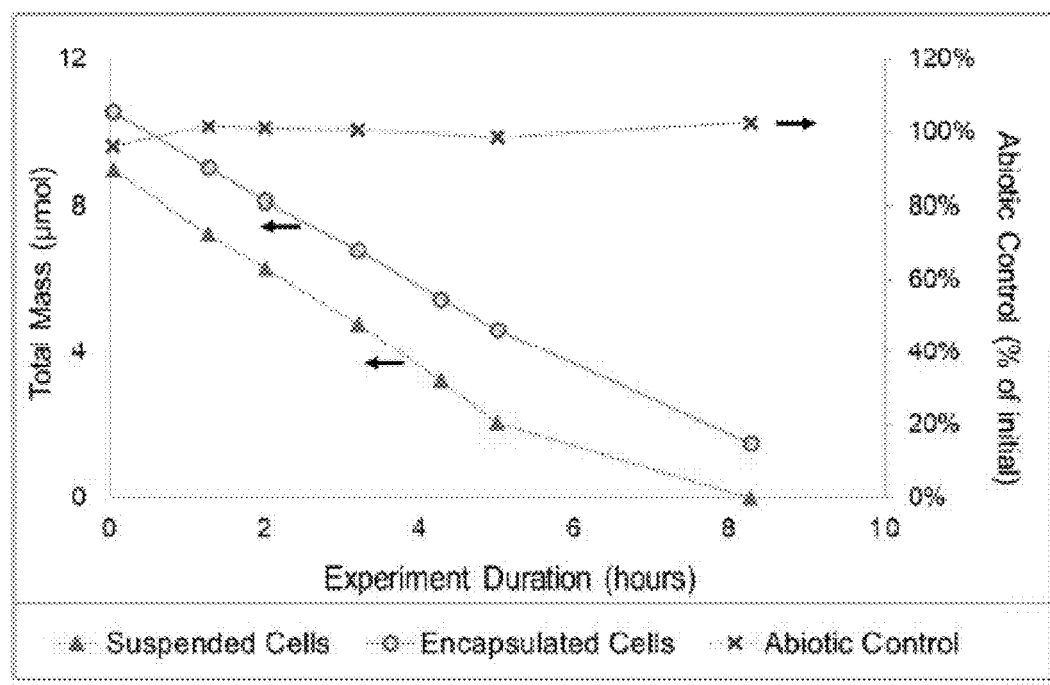
FIG. 24 is a is a graph of total mass (µmol) versus time illustrating an isobutane utilization curve measured for ATCC 21198 suspended in media and encapsulated in alginate.

An addition of concentrated pH-7 phosphate buffer to the alginate pre-gel solution to a final concentration of ≈4 mM prior to addition of cells ensured a favorable environment for the added cells, likely due to assurance of correct pH and ionic strength. Also, it was found that the higher crosslinking concentration of 1% $CaCl_2$ may have caused cell lysis due to high osmotic stress. The concentration of the crosslinking solution was lowered to 0.25% (w/v) $CaCl_2$. Adjusting these two parameters led to a big improvement in alginate encapsulated cell viability (FIG. 24) (Table 8).

TABLE 8

| Treatment | Calculated ID Utilization Rate ($\mu$mol/day/$mg_{TSS}$) | Percent Difference from Suspended |
|---|---|---|
| Suspended Cells | 15.8 | |
| Alginate Encapsulated Cells | 14.2 | −10.1% |

In one embodiment of the method concerning encapsulation of ATCC 21198 in alginate macro-beads, cells retained around 90% of their original activity and beads were highly stable in carbonate buffered MSM for at least 24 hours. Subsequent long-term experiments provided evidence that alginate macrospheres are stable for several months, even while shaking quickly, ~100 rpm, on a rotary shaker table.

Example 11

This example concerns an embodiment of gellan gum Encapsulation of ATCC 21198. ATCC 21198 encapsulated in gellan gum macro-beads produced stable and uniform cylindrical macro-beads containing ATCC 21198 that experienced minimal to no effect on substrate utilization (FIG. 5B). ATCC 21198 was successfully encapsulated in microbeads ranging in size from ~10-100 µm, determined manually from repeated bright field microscopic images. ATCC 21198 encapsulated in gellan gum micro-spheres also experienced minimal to no loss of substrate utilization rates when compared with suspended cells (FIG. 5C).

Figure 25:
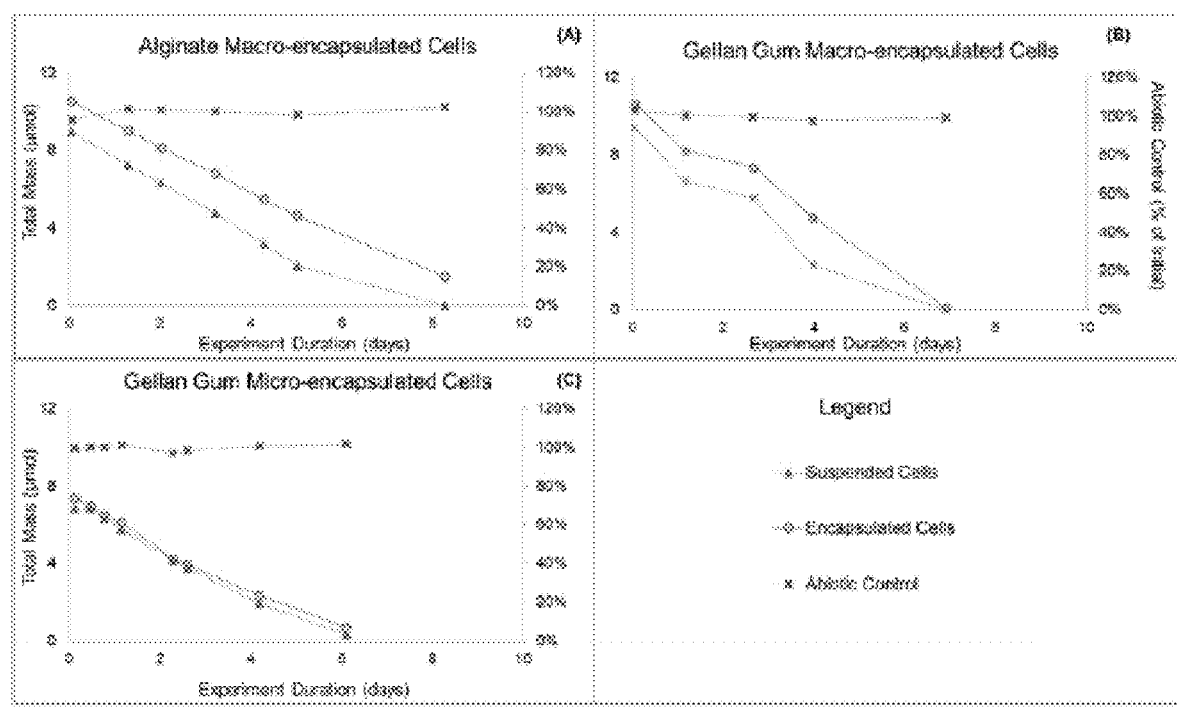
FIG. 25 provides graphs of total mass (µmol) versus time illustrating an isobutane utilization curve measured for ATCC 21198 suspended in media and encapsulated in (A) spherical alginate macro beads about 2 mm in diameter, (B) cylindrical gellan gum macro beads about 2 mm×2 mm, and (c) spherical gellan gum micro beads of about 10 to about 100 µm in diameter.

These examples established that ATCC 21198 could be encapsulated in both alginate and gellan gum matrices with minimal to no loss of cell viability, as determined via comparison to suspended cell substrate utilization rates (FIG. 25).

TABLE 9

| Encapsulation Matrix/Method | Benchmark Suspended Cell Utilization Rate ($\mu$mol/mg) | Encapsulated Cell utilization Rate ($\mu$mol/mg) | Percent Difference |
|---|---|---|---|
| Alginate Micro-bead | 15.8 | 14.2 | −10.1% |
| Gellan Gum Macro-bead | 13.3 | 13.3 | −0.6% |
| Gellan Gum Micro-bead | 11.1 | 11.0 | −0.7% |

Table 9 provides information concerning encapsulated cell viability. Percent difference is calculated as the percent change from suspended cell utilization rates to encapsulated cell utilization rates. Alginate macrobeads were spherical and ~2 mm in diameter. Gellan gum macrobeads were cylindrical and ~2 mm in diameter by ~2 mm tall. Gellan gum micro-beads were spherical ~10-100 um in diameter. FIG. 25. Isobutane utilization curves measured for ATCC 21198 suspended and encapsulated in (A) spherical alginate macro-beads ~2 mm in diameter, (B) cylindrical gellan gum macro-beads ~2 mm×2 mm and, (C) spherical gellan gum micro-beads ~10-100 µm in diameter. All data points are averages of duplicate reactors.

Example 12

This example concerns encapsulated cell co-metabolic transformation capacity and longevity. To assess the long-term effect of encapsulation on the cometabolic transformation potential of encapsulated ATCC 21198, reactors were set up with the following treatments: abiotic controls (AC), suspended cell controls (SC), alginate encapsulated cells (AEC), and gellan gum encapsulated cells (GGEC) (Table 11). ATCC 21198 was encapsulated in both alginate and gellan gum beads at a mass loading of ~0.5 $g_{TSS}/g_{bead}$ and all active reactors received an addition of cells to a concentration of ~10 mg/L. Reactors were created in triplicate to ensure reliable and repeatable data.

The two main parameters investigated were differences between suspended and encapsulated cells contaminant transformation rates and capacities. The rate at which a contaminant is transformed is important and can indicate levels of cell activity (transformation rate), though, the total mass of a contaminant that can be transformed prior to the toxic effects of contaminant transformation inhibiting cells is also important (transformation capacity).

Suspended cell transformation rates and capacities were used as a control to assess the effect of encapsulation on cells. All reactors were spiked three times over ~120 days with the chosen CoC mixture and environmentally relevant aqueous concentrations: 1,1,1-TCA (~250 ppb), cDCE (~250 ppb), and 1,4-D (~500 ppb). Respiration ($O_2$/$CO_2$) and co-metabolic activity data. CoC mixture, were monitored every 5-7 days on average. Table 10—Summary of treatments within encapsulated cell co-metabolism.

TABLE 10

| Treatment | Abbreviation | # of Reactors | REACTOR CONTENTS | | |
|---|---|---|---|---|---|
| | | | Beads | Cells | CoCs |
| Abiotic Control | SC | 3 | No | No | Yes |
| Suspended Cell Control | SC | 3 | No | Yes | Yes |
| Alginate Encapsulated Cells | AEC | 3 | Yes | Yes | Yes |
| Gellan Gum Encapsulated Cells | GGEC | 3 | Yes | Yes | Yes |

Figure 26:
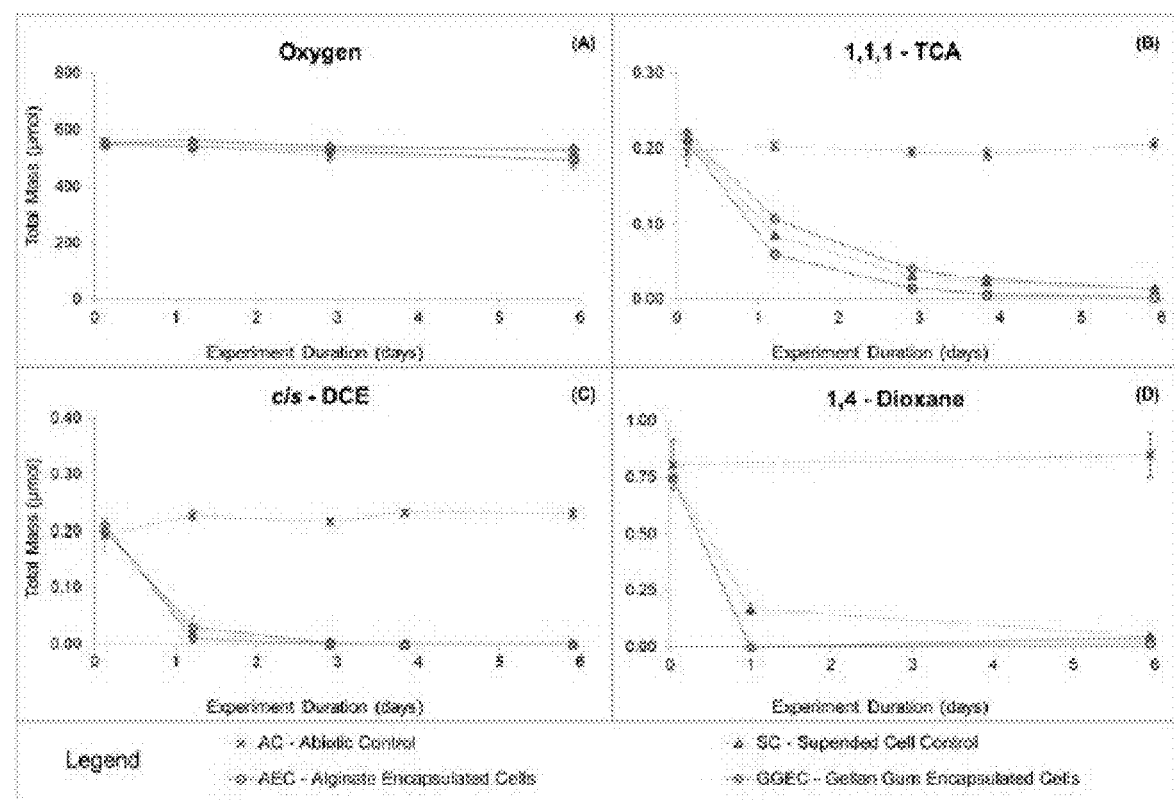
FIG. 26 provides graphs of total mass (µmol) versus time illustrating contaminant transformation data by ATCC 21198 encapsulated in alginate and gellan gum.

FIG. 26 is a clipped and magnified presentation of initial contaminant transformation and respiration data collected over the first addition of contaminants to all reactors. The initial transformation rates of all contaminants were similar between all active treatments, observed visibly (FIG. 26). FIG. 26 provides contaminant transformation data for the initial spike of contaminants. These data have been clipped from the entire time-series data presented below to illustrate initial transformation rates and provide a comparison between suspended and encapsulated cell reactor treatments initial ability to transform contaminants. Data points are averages between triplicate reactors and errors bars are 95% confidence intervals.

These data confirm that ATCC 21198 has the ability to simultaneously transform a mixture of chlorinated contaminants and 1,4-D at environmentally relevant concentrations. Respiration data has changed minimally over the first 7 days, as expected due to the absence of a primary substrate or carbon source and the low masses of contaminants transformed. <2 μmol, not requiring measurable amounts of O to oxidize. $CO_2$ data not presented here, follow the same horizontal trend, showing minimal $CO_2$ production.

Example 13

Figure 27:
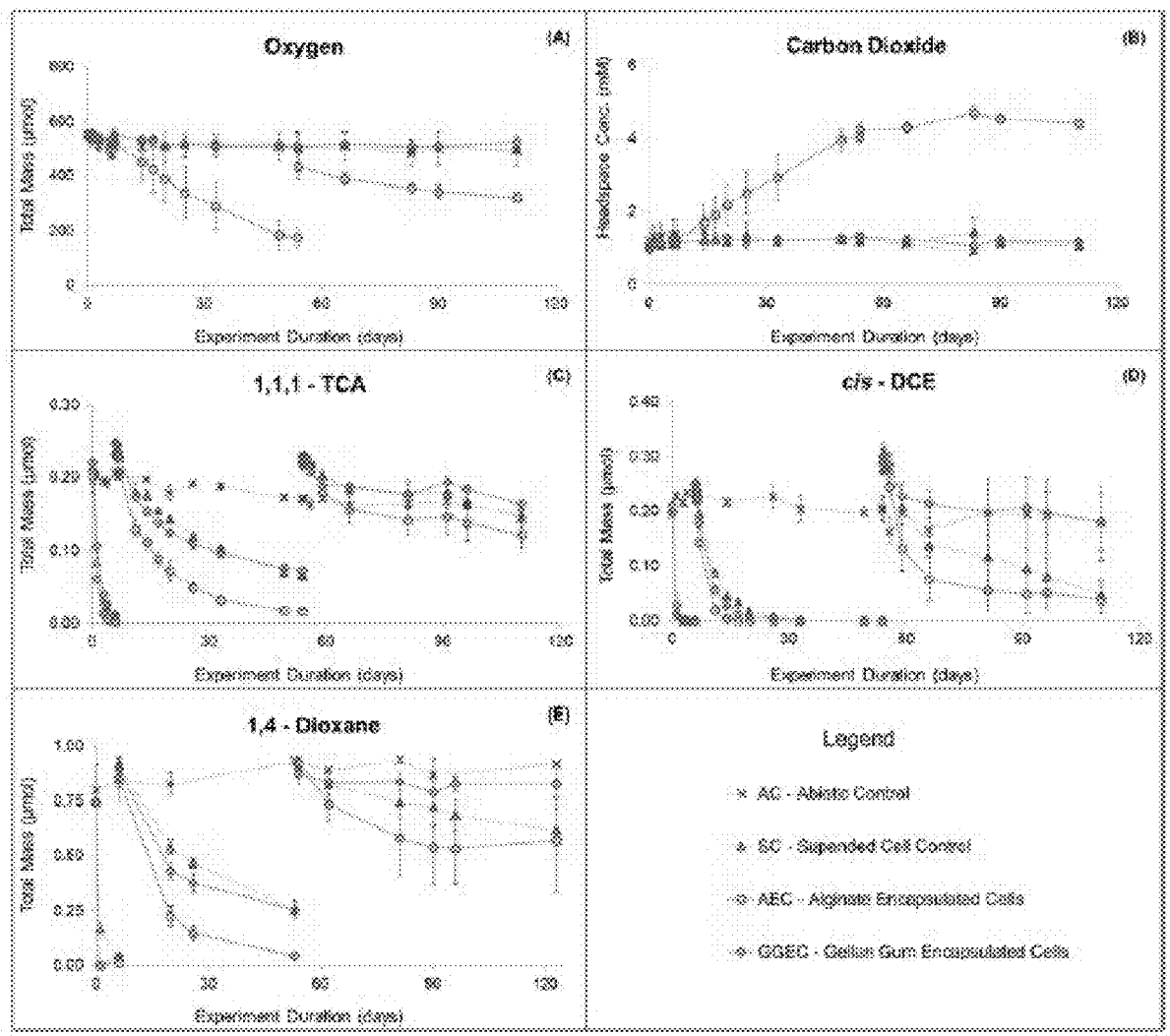
FIG. 27 provides graphs of total mass (µmol) versus time illustrating the results of a co-metabolic transformation study by ATCC2198 encapsulated in alginate and gellan gum.

This example concerns successive contaminant additions. Active reactors received successive additions of contaminants when the majority of the previous addition had been transformed. Upon injection of the second and third addition of contaminants, a decrease in cellular transformation rates was observed, visibility for all treatments (FIG. 27). FIG. 27 provides data from a long-term encapsulated cell cometabolic transformation study. (A-B) Respiration data. $O_2$ measurements reported as ~180 μmol is assumed to be near zero due to vacuum created within reactors. $CO_2$ data are presented in terms of measured headspace concentrations due to speciation of $CO_2$ in carbonate system in the aqueous phase and lack of pH measurements throughout experiment. (C-E) Contaminant transformation data Three contaminant additions were made to each reactor and breaks in time-series connection lines signify successive additions. Data points are averages between triplicate reactors in each treatment and errors bars are 95% confidence intervals.

FIG. 27(C-E) illustrates that ATCC 21198, even in suspended cell reactors, maintained some cometabolic activity for over 120 days. This finding suggests that ATCC 21198 has the capability under certain growth conditions to store energy during growth, which can be utilized over extended durations, to produce or maintain enzymes that are suitable for metabolic transformation of contaminants, such as non-specific oxygenase enzymes that are responsible for co-metabolism. The production of particular proteins that are produced to collect and store diverse compounds for later use as energy or nutrients has been observed by other *Rhodococcus* species in previous studies and may explain the observed long-term activity above.

Also surprisingly, alginate encapsulated cells were able to transform a greater percent of successive spikes at a faster rate than suspended or gellan gum encapsulated cells (FIG. 27)(Table 11). Data became variable within reactors of the same treatment in the third spike of contaminants and cometabolic activity in one gellan gum reactor ceased, as indicated by the deviation of the gellan gum time-series from the suspended in transformation of cDCE, and the large error bars in the replicate treatments. To examine any statistical difference in cometabolic transformation ability between treatments, average transformation capacities within each treatment were calculated based on the mass of each contaminant transformed per mass of cells over the duration of this experiment (Table 11). Table 11 provides Contaminant Transformation capacities calculated from the summation of all contaminants transformed over all three spikes added to each reactor. Data are average transformation capacities between triplicate reactors bounded by calculated 95% confidence intervals.

TABLE 11

| | | TRANSFORMATION CAPACITY ($mg_{CoC}$/$mg_{TSS}$) | | |
|---|---|---|---|---|
| Treatment | Abbreviation | 1,1,1-TCA | cDCE | 1,4 Dioxane |
| Suspended Cell Control | SC | 0.43 ± 0.04 | 0.66 ± 0.09 | 1.65 ± 0.20 |
| Alginate Encapsulated Cells | AEC | 0.51 ± 0.04 | 0.68 ± 0.05 | 1.90 ± 0.38 |
| Gellan Gum Encapsulated Cells | GGEC | 0.42 ± 0.01 | 0.57 ± 0.06 | 1.39 ± 0.13 |

Statistical analysis of 1,1,1-TCA transformation capacities provided evidence that alginate-encapsulated cell transformation capacities were statistically greater than both suspended and gellan gum encapsulated cells. In addition to greater transformation capacities, the rate at which alginate encapsulated cells transformed contaminants was greater (FIG. 27). Suspended and gellan encapsulated cell transformation capacities did not have a statistically significant differences. The calculated transformation capacities are higher than previously observed capacities for ATCC 21198, though previous studies were short term and did not allow slow long-term transformation to proceed.

Respiration data for suspended and gellan gum encapsulated cells show little activity, as expected, due to no primary substrate addition and the relatively small amount of contaminants added. <5 μmol total. However, measurable amounts of $O_2$ consumption and $CO_2$ production began in alginate bottles around day 10 (FIG. 27). This oxygen consumption followed a negative linear trend out to day 54 when the $O_2$ was effectively depleted. The headspace in the AEC reactors was refreshed with pure $O_2$ on day 54 to ensure transformation of CoCs proceeded.

The depletion of)$_2$ in alginate encapsulated cell reactors is suspected to be due to cellular utilization of the alginate encapsulation matrix because it is the only carbon source within the reactors other than biomass. Energy gained by the consumption of alginate is one theory for the elevated cellular activity and corresponding rate and capacity of CoC transformation observed within these reactors.

Conservative stoichiometric analysis, based on respiration equation 2, using the measured amount of $O_2$ consumed over the entire duration of this experiment, suggests that cells in AEC reactors have consumed ~25% of the added alginate. Conservatively assuming the biomass yield constant for AICC 21198 grown on alginate is at least 50% of the yield constant for isobutane, then the estimated amount of alginate consumption would correspond to an increase in biomass of ~7 times compared to the biomass initially added to AEC reactor s, over the ~120 day period.

$$C_6H_8O_6 + 5O_2 \rightarrow 4H_2O + 6CO^2 \qquad \text{Equation 2}$$

Transformation rates and capacities in alginate reactors were greater on average than suspended cells, though not in proportion to the estimated cell population growth. Also, the observed decrease in transformation rate in successive spikes is not indicative of cellular growth. Slow consumption of alginate correlated with an increase in cellular activity and cometabolic transformation potential, indicating that the encapsulation matrix may have been acting as a SRC for encapsulated cultures. However, the observed respiration of alginate in combination with physical agitation from reactors being stored on a rotary shaker table shaking at ~100 rpm led to instability and disintegration of alginate beads, visibly observed starting at ~60 days. Higher resistance to enzymatic degradation is desired in order to maintain the integrity of augmented beads. As expected, gellan gum macro-beads were observed, visibly, to have deteriorated much less over the ~120 day period.

Both suspended and encapsulated ATCC 21198 can maintain co-metabolic transformation potential for extended periods. In addition, alginate beads were less resistant to degradation than gellan gum. The observed cellular utilization of alginate was not an expected but did provide evidence that a slowly accessible carbon source can potentially improve an augmented cultures co-metabolic transformation potential. However, for certain objectives concerning prolonged cellular and SRC encapsulation in order to prevent issues including SRC release and transport, cellular release and transport and potential excess biological oxygen demand by a non-inducing growth substrate. Important to this point is the finding that an oxygen demand was not observed with gellan gum in comparison to suspended cells, even in the presence of a contaminant microbe, and gellan gum encapsulated cells were also found to have minimal to no loss of cometabolic activity when compared to suspended cells.

Gellan Gum (GG) was selected as a primary encapsulation matrix for certain investigations.

Example 14

This example concerns SRC encapsulation. SRCs were analyzed for their potential to supply substrates to encapsulated microbes. TBOS and $T_2BOS$, exist in pure phase as light non-aqueous phase liquids (LNAPLs). NAPLs, essential oils, can be trapped in alginate hydrogel matrices to load beads with oils as high as ~25% (w/w). Disclosed embodiments were found to be highly efficient, successfully entrapping ~90% of the oil added. Using the optimized methods for encapsulating ATCC 21198, in combination with known oil encapsulation methods, methods were developed for the successful encapsulation of SRCs within alginate and gellan gum matrices.

1. Alginate Encapsulation of SRCs

Figure 28:
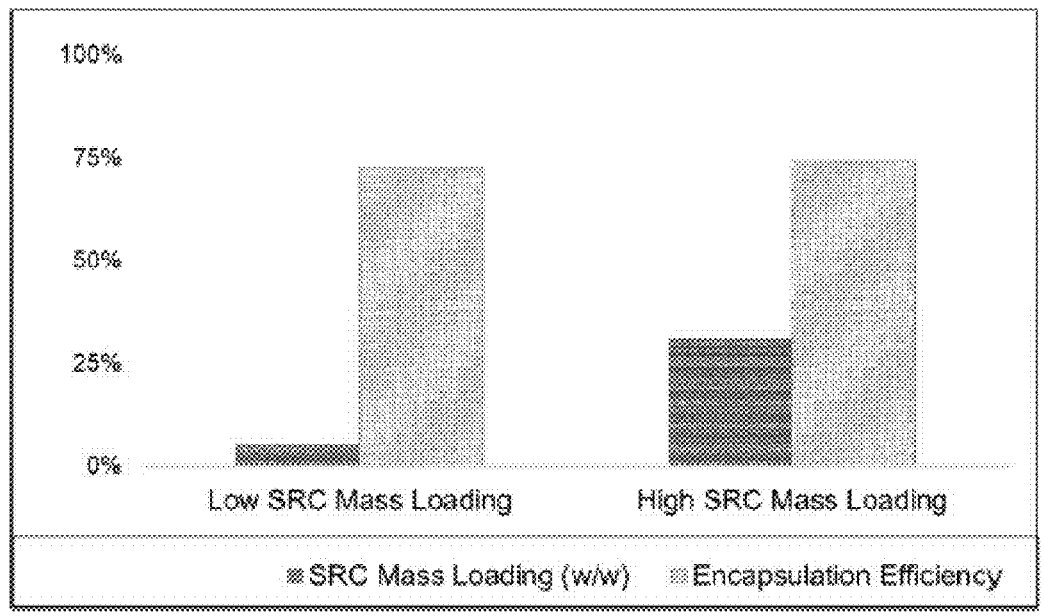
FIG. 28 is a bar graph of percent versus mass loading (w/w) illustrating data for encapsulation of TBOS in alginate.

TBOS was used as the model LNAPL SRSSRC for encapsulation method development due to its availability and low cost. Initial attempts were aimed at creating alginate macro-beads with TBOS mass loadings of 5 and 30% (w/w). To do so, TBOS was added to alginate pre-gel solution at 5% and 30% (w/v). This mixture was emulsified with the aid of Span-80 emulsifier and beads were created. Through the initial method developed TBOS could be encapsulated successfully in beads at 5 and 30% (wTBos/wbead) (FIG. 28). Approximately ~75% of the added TBOS was recovered within beads in both cases ((FIG. 28). (FIG. 28) provides information concerning TBOS encapsulation in alginate. Low SRC Mass Loading (5%, w/w). High SRC Mass Loading (30% w/w).

2. Gellan Gum Encapsulation of SRCs

Due to similarities between the hysteresis gelation mechanism of agarose and gellan gum, initial attempts to encapsulate SRCs in gellan gum macro-beads followed in which half sphere agarose macro-beads were made by extruding drops of heated pre-gel solution onto a hydrophobic surface and allowing the extruded drops to cool at room temperature to gelate.

From the successful encapsulation techniques developed for alginate, it was determined that inclusion of LNAPL SRCs within a hydrogel matrix was facilitated by creating a stable emulsified SRC-hydrogel solution; however, the emulsifier reduced the surface tension of the gellan gum pre-gel solution. After extrusion of the heated pre-gel drops onto the hydrophobic surface, the lowered surface tension caused the droplets to flatten into one another or form disc shaped beads. It was observed visibly that beads did contain SRCs within the encapsulation matrix. Other embodiments produced cylindrical gellan gum macro-beads that contained SRCs at mass loadings up to ~8% (w/w) with encapsulation efficiencies of ~80%. Micro-encapsulation of LNAPL SRCs were explored to encapsulate SRCs in micro-beads ranging in size from 10-40 µm.

From direct analysis of SRCs entrapped within alginate and gellan gum macro-beads it was determined that LNAPLs, such as TBOS and $T_2BOS$, could be successfully encapsulated in both alginate and gellan gum matrices at mass loadings as high as 30 and 8% (w/w), respectively. In addition to this success, encapsulation efficiencies were above 75% for both methods.

From these results it was conservatively estimated that ~89 $mg_{TSS}$ of biomass per gram of bead could be generated. This was based on the complete hydrolysis of 10% encapsulated TBOS to 1-butanol and the assumption that the biomass yield coefficient for ATCC 21198 grown on 1-butanol was 50% of the known yield for isobutane. These calculations establish that encapsulated SRCs produce inducing growth substrates and encapsulated cultures can utilize those substrates, thereby extending the cometabolic remediation potential of initially augmented biomass.

Example 15

This example concerns an embodiment of abiotic hydrolysis of encapsulated slow release substrates. TBOS and T2BOS encapsulated in alginate and gellan gum beads and were suspended in solution to investigate the rate of substrate release, 1- and 2-butanol respectively, after encapsulation Determining the rate at which these compounds hydrolyze and produce substrates establishes the possible duration of hydrolysis, rate of substrate production and cellular growth, oxygen demand related to product consumption, and distinguishes possible biotic hydrolysis when orthosilicate compounds are co-encapsulated with microbes.

Reactors with TBOS and T$_2$BOS in free suspension at concentrations that replicate encapsulated SRC reactors were created to determine the effect of encapsulation on SRC hydrolysis. Substrate production rates were used as a proxy for SRC hydrolysis, due to the simplicity of substrate analysis. Direct measurements of 1- and 2-butanol in solution were made in order to determine substrate production rates and measurements are presented on a total mass produced basis. Hydrolysis of orthosilicate compounds is acid and base catalyzed and therefore, observed hydrolysis rates are on the low end of what is possible, due to suspension in pH-7 media.

The concentrations of TBOS and T$_2$BOS in solution effects the rate of hydrolysis, and therefore, concentrations of SRCs in abiotic reactors were created to mimic the concentration of SRCs in biotic co-encapsulated reactors, ~1000-1500 mg/L. Biotic and abiotic reactors were created in unison and monitored alongside one another, though abiotic data have been separated and are presented below. To prevent contamination from occurring over the long duration of these experiments sodium azide, 0.2% (w/v), was added to all abiotic reactors.

Due to the ease of encapsulation of SRCs within alginate, initial abiotic hydrolysis work was conducted using alginate encapsulated TBOS. TBOS was encapsulated in abiotic alginate macro-beads at a mass loading of ~5% and 30% (w/w). These beads were then added to triplicate reactors, such that the final TBOS concentration in pH-7 carbonate buffered media was kept constant at ~1000 mg/L; i.e., 2 grams of 5% beads and ⅓ grams of 30% beads were added to 100 mL media solution. This corresponds to total TBOS masses in reactors of ~100 mg or ~312 μmol and to maximum 1-butanol production masses of ~92.5 mg or ~1250 μmol. To illustrate the effect of encapsulation on the hydrolysis rate of TBOS, reactors containing similar concentrations of suspended TBOS were created and monitored alongside encapsulated TBOS reactors.

Figure 29:
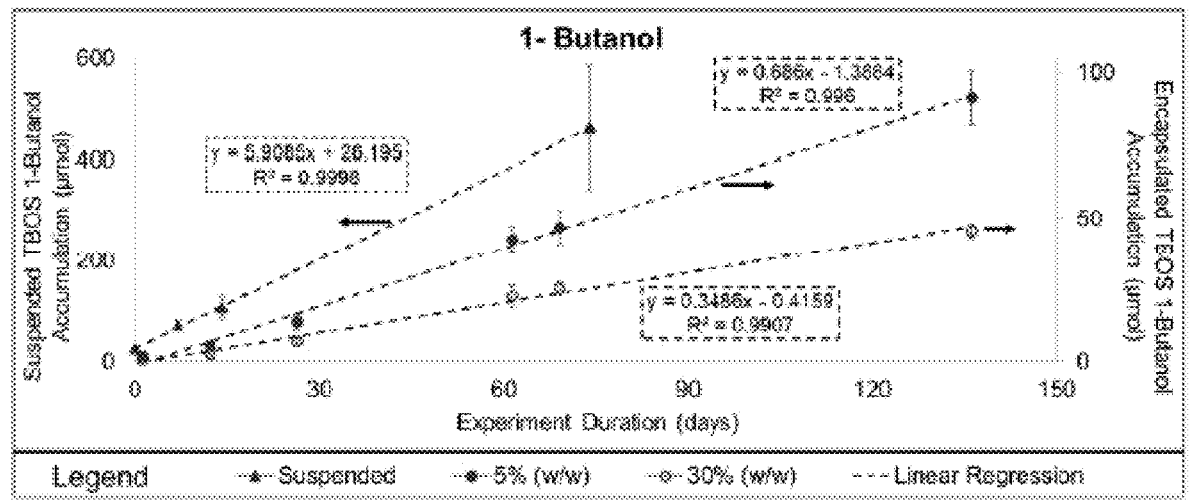
FIG. 29 provides data concerning measured 1-butanol masses in solution from the abiotic hydrolysis of suspended (left axis) and alginate encapsulated T2BOS (right axis).

All reactors were monitored for 1-butanol production over ~140-day period (FIG. 29) 1-butanol production rates were modeled via linear regression over the full time period of data collection and comparisons were made between the three treatments: suspended TBOS, low mass loaded beads (5% TBOS w/w), and high mass loaded beads (30% TBOS w/w) (Table 12). FIG. 29 provides information concerning 1-butanol masses in solution from the abiotic hydrolysis of suspended (left-axis) and alginate encapsulated TBOS (right-axis). Total TBOS solution concentrations of ~1000 mg/L and bead mass loading ~5 and 30% (w/A). Datapoints are averages between duplicate (suspended) or triplicate (encapsulated) reactors in each treatment and errors bars are 95% confidence intervals. Suspended TBOS reactors were created after encapsulated reactors and therefore, have a shorter total duration of measurements.

l-Butanol was produced at an order of magnitude greater rate when TBOS was in free suspension than when encapsulated (FIG. 29) (Table 12). One theory for this observed phenomenon is that while reactors are stored on a shaker table, at ~100 rpm, the LNAPL TBOS in suspension forms a quasi-emulsion within the aqueous phase and the small droplets of LNAPL in solution provide a large surface area for hydrolysis to occur. This does not occur in encapsulated LNAPL reactors, because LNAPL droplets are held within a physical barrier and do not spread throughout solution. Accordingly, 1-butanol diffusion away from hydrolysis sites, out of beads, and water exchange to hydrolysis sites, into beads, may limit the rate of hydrolysis.

TABLE 12

| Treatment | Measured Initial TBOS Mass (μmol) | Maximum Possible Butanol Release (μmol) | Butanol Production Rate (μmol/day) | Estimated Exhaustion of TBOS (years) |
|---|---|---|---|---|
| Suspended TBOS | 312 | 1247 | 5.9 | 0.6 |
| Encapsulated TBOS (5% w/w) | 326 | 1305 | 0.69 | 5.2 |
| Encapsulated TBOS (30% w/w) | 324 | 1295 | 0.35 | 10.1 |

The abiotic hydrolysis rate of both TBOS and T2BOS encapsulated in gellan gum was also investigated. Both SRCs were encapsulated in cylindrical gellan macro-beads at mass loadings of ~8% (w/w). For this work ATCC 21198 was also co-encapsulated within the gellan gum matrix at initial concentrations of ~0.5 mg$_{Tss}$/g, and an addition of 0.2% (w/v) sodium azide was added as a cellular poison to ensure cells were not alive within the matrix. Biomass was encapsulated because it had been determined that encapsulated SRCs may hydrolyze more quickly with cells present within the encapsulation matrix. Although, the increase in hydrolysis rate was not proven to be from biotic hydrolysis of SRCs and may have been due to the presence of biomass within the matrix allowing more diffusion of water into and butanol out of beads. Therefore, poisoned biomass was included within the matrix to ensure encapsulated SRC abiotic hydrolysis rates would be directly comparable to co-encapsulated reactors containing active biomass. Two grams of beads were added to each abiotic reactor such that a final concentration of ~1500 mg/L TBOS and T2BOS was achieved, or a total mass of ~155 mg or ~484 μmol was added. Reactors containing suspended T2BOS at ~1500 mg/L were created for comparison.

Analogous to alginate encapsulated and suspended TBOS data, encapsulated T$_2$BOS hydrolyzed an order of magnitude more slowly than suspended T$_2$BOS (FIG. 30) (Table 13).

TABLE 13

| Treatment | Measured Initial BOS Mass (μmol) | Maximum Possible Butanol Release (μmol) | Butanol Production Rate (μmol/day) | Estimated Exhaustion of T2BOS (years) |
|---|---|---|---|---|
| Suspended T$_2$BOS | 476 | 1901 | 0.40 | 12.9 |
| GG Encapsulated T$_2$BOS (8% w/w) | 441 | 1763 | 0.03 | 169 |
| GG Encapsulated TBOS (8% w/w) | 479 | 1916 | 1.3 | 4.0 |

Figure 30:
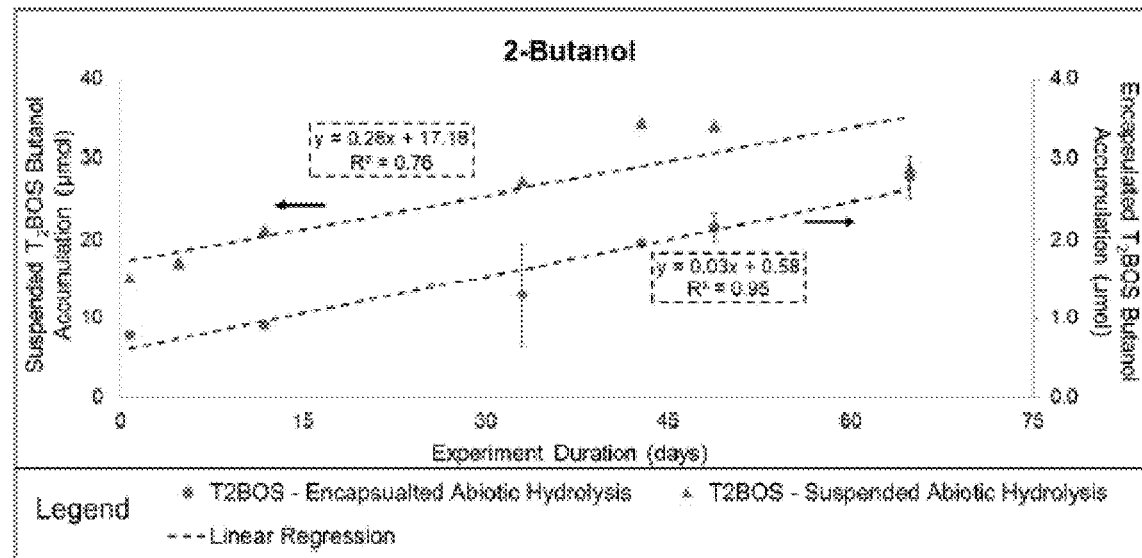
FIG. 30 provides data concerning measured 2-butanol masses in solution from the abiotic hydrolysis of suspended (left axis) and gellan gum encapsulated TBOS (right axis).

FIG. 30 provides information concerning measured 2-butanol masses in solution from the abiotic hydrolysis of suspended (left-axis) and gellan gum encapsulated T$_2$BOS (right-axis). Total T$_2$BOS solution concentrations of ~1500 mg/L and bead mass loading ~8% (w/w) are illustrated. Data points are averages between duplicate reactors in each treatment and errors bars are 95% confidence intervals.

Figure 31:
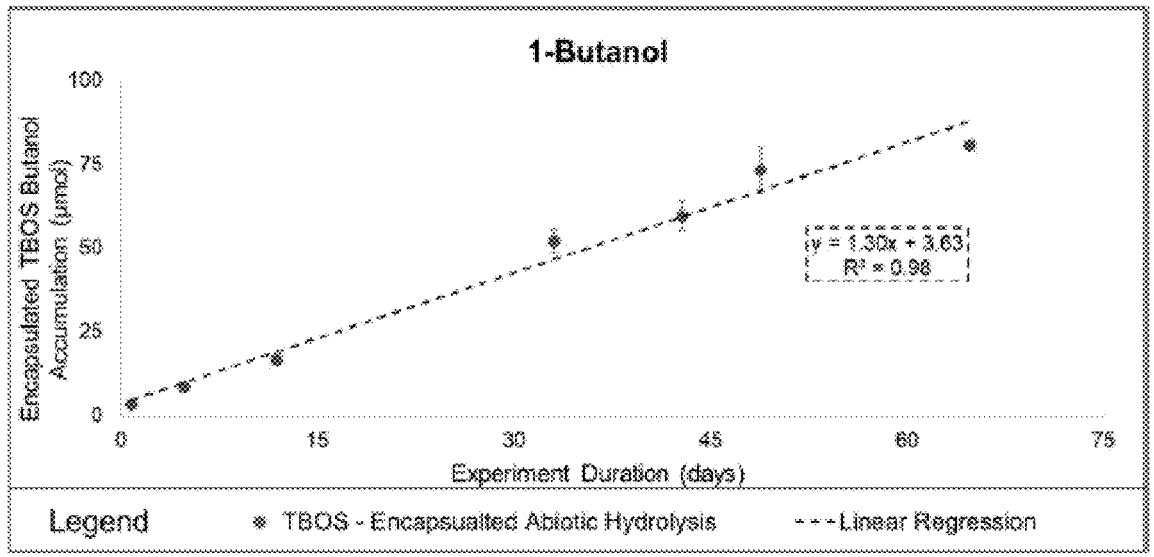
FIG. 31 provides data concerning measured 1-butanol masses in solution from the abiotic hydrolysis of gellan gum encapsulated TBOS.

The hydrolysis rate for TBOS encapsulated in gellan gum at ~8%/o (w/w) and at total solution concentrations of ~1500 mg/L, presented in FIG. 31 (1.3 µmol/day), are within the range observed for TBOS at ~1000 mg/L (0.34-5.9 µmol/day) (FIGS. 29 & 31). However, gellan gum encapsulated TBOS hydrolyzed ~2-4 times more quickly than alginate encapsulated TBOS (Table 15). This is likely be due to higher solution concentrations of TBOS in gellan gum reactors than in alginate reactors; however, differences in the encapsulation matrix and the inclusion of ATCC 21198 biomass within gellan gum beads and not in alginate beads may have also played a role in the observed difference. FIG. 31 provides information concerning measured 1-butanol masses in solution from the abiotic hydrolysis of gellan gum encapsulated TBOS. Total TBOS solution concentration of ~1500 mg/L and bead mass loading ~8% (w/w). Excel linear trendline function fit to time-series and the black-dashed box represents the linear regression equation calculated by excel linear trendline tool. Data points are averages between duplicate reactors and errors bars are 95% confidence intervals. Table 14 provides information concerning abiotic hydrolysis rates used to predict the lifetime of gellan gum encapsulated TBOS and $T_2BOS$ in reactors in total solution concentration 1500 mg/l and bead mass loading ≈8% (w/w).

It can be seen from direct comparisons between substrate production rates between gellan gum encapsulated TBOS and T2BOS, both encapsulated at mass loadings of ~8% and in solution at ~1500 mg/L, that TBOS hydrolyzes ~45 times more quickly (Table 14 and 15).

TABLE 14

| Treatment | Measured Initial BOS Mass (µmol) | Maximum Possible Butanol Release (µmol) | Butanol Production Rate (µmol/day) | Estimated Exhaustion of TBOS (years) |
|---|---|---|---|---|
| Suspended T2BOS | 475.2 | 1901 | 0.40 | 12.9 |
| GG Encapsulated T2BOS (8% w/w) | 440.6 | 1763 | 0.03 | 169 |

TABLE 14-continued

| Treatment | Measured Initial BOS Mass (µmol) | Maximum Possible Butanol Release (µmol) | Butanol Production Rate (µmol/day) | Estimated Exhaustion of TBOS (years) |
|---|---|---|---|---|
| GG Encapsulated TBOS (8% w/w) | 479.1 | 1916 | 1.3 | 4.0 |

This is an expected result due to previous research showing that the more sterically hindered the central silicate is by the leaving groups, the less access water has to hydrolysis sites. Estimates of times to exhaustion of the T2BOS that is encapsulated is over 100 years.

For comparison, Table 15 summarizes all abiotic hydrolysis rates presented in the above sections. The observed order of magnitude reduction in hydrolysis rates after encapsulation of both TBOS and TiBOS is an important finding that may allow for more informed decisions to be made for the selection of SRCs in future applications of this technology. Observed differences in hydrolysis rates when SRCs were encapsulated at different mass loadings, as seen in row 2-3 of Table 15, provide a useful method for controlling the rate of release of substrates. These controls might allow for the mitigation of excess substrate release leading to excess cellular growth and issues like well clogging or oxygen depletion. Also, as expected slight differences in leaving groups attached to orthosilicate compounds, 1- or 2-butanol, drastically altered the butanol production rate, slower for branched alcohols (Table 15).

TABLE 15

| Treatment | Initial SRS Solution Conc. (mg/L) | Poisoned Cells Present | Measured Initial SRS (µmol) | Maximum Possible Butanol (µmol) | Butanol Production Rate (µmol/day) | Estimated Exhaustion of SRS (years) |
|---|---|---|---|---|---|---|
| Suspended TBOS | 1000 | No | 311.9 | 1247.4 | 5.91 | 0.58 |
| Alginate Encapsulated TBOS (5% w/w) | 1000 | No | 326.2 | 1304.7 | 0.69 | 5.17 |
| Alginate Encapsulated TBOS (30% w/w) | 1000 | No | 323.7 | 1294.8 | 0.35 | 10.12 |
| Gellan Gum Encapsulated TBOS (8% w/w) | 1500 | Yes | 479.1 | 1916.2 | 1.3 | 4.00 |
| Suspended $T_2BOS$ | 1500 | No | 475.2 | 1901 | 0.40 | 12.9 |
| GG encapsulated $T_2BOS$ (8% w/w) | 1500 | Yes | 440.6 | 1762.5 | 0.03 | 169 |

Another important finding is the extended duration of possible substrate release ranging from several to hundreds of years (Table 15). The observed possible substrate production rate and duration provide supporting evidence that a single injection of co-encapsulated SRCs to the subsurface could produce low amounts of substrates over long periods of time, which could potentially drive contaminant remediation for a much longer period of time than current biostimulation or bioaugmentation applications. However, investigation into the kinetics of hydrolysis, cell substrate utilization, cell respiration, cell decay, and contaminant transformation will be necessary to better understand the desired rate of substrate release and duration.

Example 16

This example concerns co-encapsulated cell co-metabolic transformation longevity studies. ATCC 21198 was co-encapsulated with SRCs, TBOS or T2BOS, to determine if ATCC 21198 could be induced by or gain energy from SRC products, 1- and 2-butanol, such that transformation rates or capacities of initially encapsulated biomass was greater than similar biomasses of suspended cells without access to SRCs or substrates.

Gellan gum was used as an encapsulation matrix due to observed superiority over alginate in resistance to enzymatic degradation and long-term durability. For certain embodiments, microbial consumption of alginate led to alginate bead instability, and caused encapsulated SRSs to be released to solution. In contrast, ATCC 21198 did not have the ability to consume gellan gum, and it had been observed that gellan gum macro-beads remained stable for over 120 days while shaking at ~100 rpm on a shaker table, whereas, alginate macro-beads did not.

Cylindrical gellan gum macro-beads containing ATCC 21198 and TBOS/T2BOS were created with biomass loadings of ~0.5 $mg_{TSS}/g_{bead}$ and SRS mass loadings of ~8% (w/w) SRS. Both SRSs were examined within this experiment to observe the difference between SRSs producing a non-inducing growth substrate, 1-butanol, and an inducing growth substrate, 2-butanol, and the effect of different substrate production rates on substrate utilization and oxygen consumption.

Two grams of beads were added to reactors to achieve final cell concentrations of ~10 $mg_{TSS}/L$ and SRS concentrations of ~1500 mg/L. The initial cell concentration within reactors was designed to directly compare to previous encapsulated cell experiments, and the initial SRS concentrations to compare to encapsulated abiotic hydrolysis work conducted with TBOS and T2BOS. Certain embodiments of disclosed abiotic hydrolysis information was conducted using the same batch of beads created for this embodiment but with an addition of sodium azide to reactors to ensure added ATCC 21198 did not survive. Data from abiotic hydrolysis experiments using the same batches of beads are presented with active reactor data to provide comparisons between observed respiration in active bottles and observed substrate, 1- and 2-butanol, production in poisoned bottles.

An abiotic control with no addition of beads ensured transformation of added CoCs was biotic. Suspended cell controls illustrated the effect of co-encapsulation on initial and long-term cell viability, as measured via CoC transformation rates and capacities. Reactors were created in duplicate or triplicate. A summary of the treatments examined within the experiment are presented in Table 16.

All reactors were spiked initially with the chosen CoC mixture at environmentally relevant aqueous concentrations 1,1,1-TCA {~250 ppb}, cDCE {~250 ppb}, and 1,4-D (~800 ppb). All data are presented on a total mass basis within reactors calculated via Henry's law. Successive spikes of contaminants were made to reactors, over ~90 days, after the majority of contaminants were transformed. The concentration of subsequent spikes were doubled in an attempt to challenge cell transformation capacities. Respiration data ($O_2/CO_2$), substrate data (1-/2-butanol), and contaminant data (1,1,1-TCA/cDCE/1,4-D) were monitored as necessary.

TABLE 16

Co-Encapsulated Cell Co-metabolic Transformation Longevity Study

| | | REACTOR CONTENTS | | | |
| --- | --- | --- | --- | --- | --- |
| Treatment | Abbreviation | # of Reactors | Beads (2 g) | SRS (TBOS/T2BOS) | Cells | CoCs |
| Abiotic Control | AC | 1 | No | No | No | Yes |
| Suspended Cell Remediation Control | SC | 2 | Yes | No | Yes | Yes |
| Co-encapsulated TBOS/ATCC 21198 | CET | 2 | Yes | Yes | Yes | Yes |
| Co-encapsulated T2BOS/ATCC 21198 | CET2 | 3 | Yes | Yes | Yes | Yes |

The data collected are presented based on the model SRCs that was encapsulated. Control reactor data (AC & SC) are presented initially with analysis of cellular viability post encapsulation. Control data are followed by a comparison to reactors containing cells co-encapsulated with TBOS (CET), a comparison to reactors containing cells co-encapsulated with T2BOS (CET 2), a data summary section concluding data presentation, and finally a summary and conclusion section.

1. Initial Cellular Viability

Figure 32:
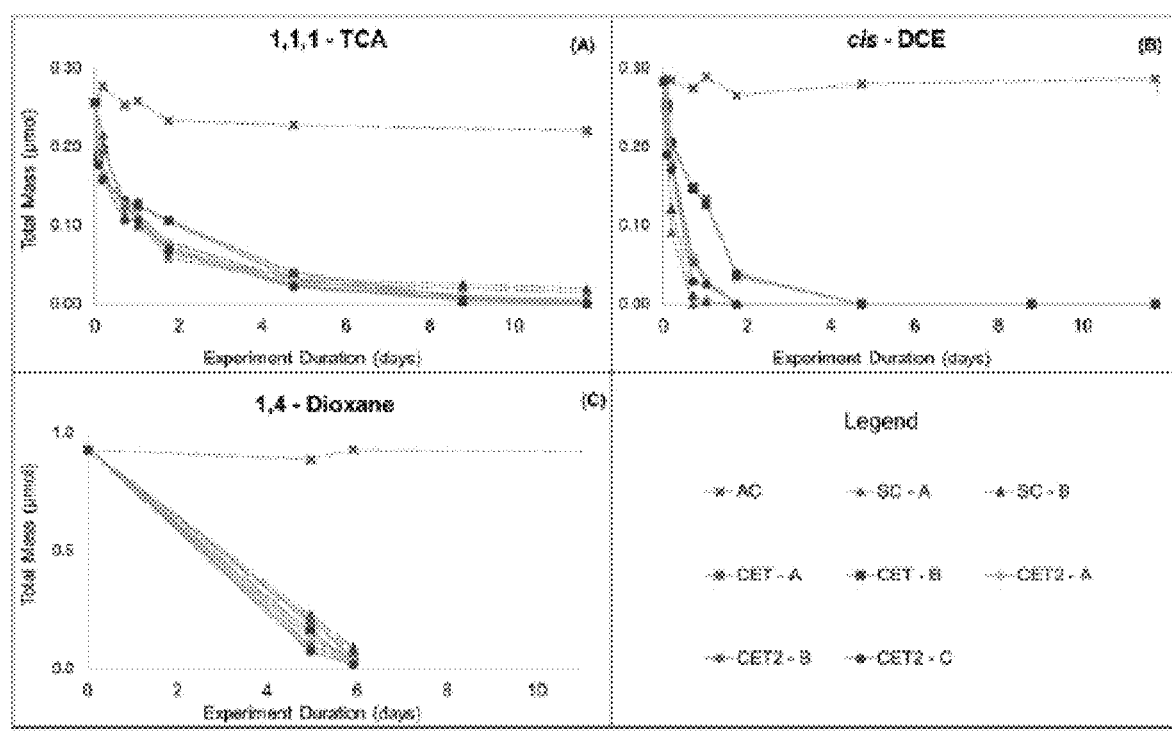
FIG. 32 provides data concerning total mass (µmol) versus time for initial contaminant transformation between suspended and co-encapsulated ATCC 21198.

To understand the effect of co-encapsulation on cell viability, initial CoC transformation rates from a first addition of contaminants were compared visibly between suspended and both co-encapsulated treatments (FIG. 32). It became necessary to present all time-series data separately, as duplicates diverge at times for reasons explained below. FIG. 32 provides initial contaminant transformation data comparison between suspended and co-encapsulated ATCC 21198. (AC)—Abiotic control. (SC)—Suspended cell control reactors. (CET) Cells co-encapsulated with 8% (w/w) TBOS. (CET2) Cells co-encapsulated with 8% (w/w) T2BOS. Alphabetical designations (A,B,C) are used to signify replicate reactors. AC has a single reactor, whereas SC and CET treatments hate duplicate reactors, and $CET_2$ has triplicate reactors.

Using the initial transformation rates of contaminants as a proxy for cell viability indicates that encapsulated cells are minimally effected by the co-encapsulation process (FIG. 32). The lagged transformation of cis-DCE and to a lesser extent 1,1,1-TCA in reactors containing ATCC 21198 co-encapsulated with TBOS (CET) in comparison to suspended cells does indicate cells may have been slightly impaired initially. Transformation rates for cells co-encapsulated with $T_2BOS$, compare well with suspended cells. These data in comparison illustrate advancements made to encapsulation processes. Initial abiotic control data show minimal decrease in contaminant masses, indicating transformation of contaminants is due to the addition of ATCC 21198 and microbial contamination is not present within the AC at the inception of this experiment.

Figure 33:
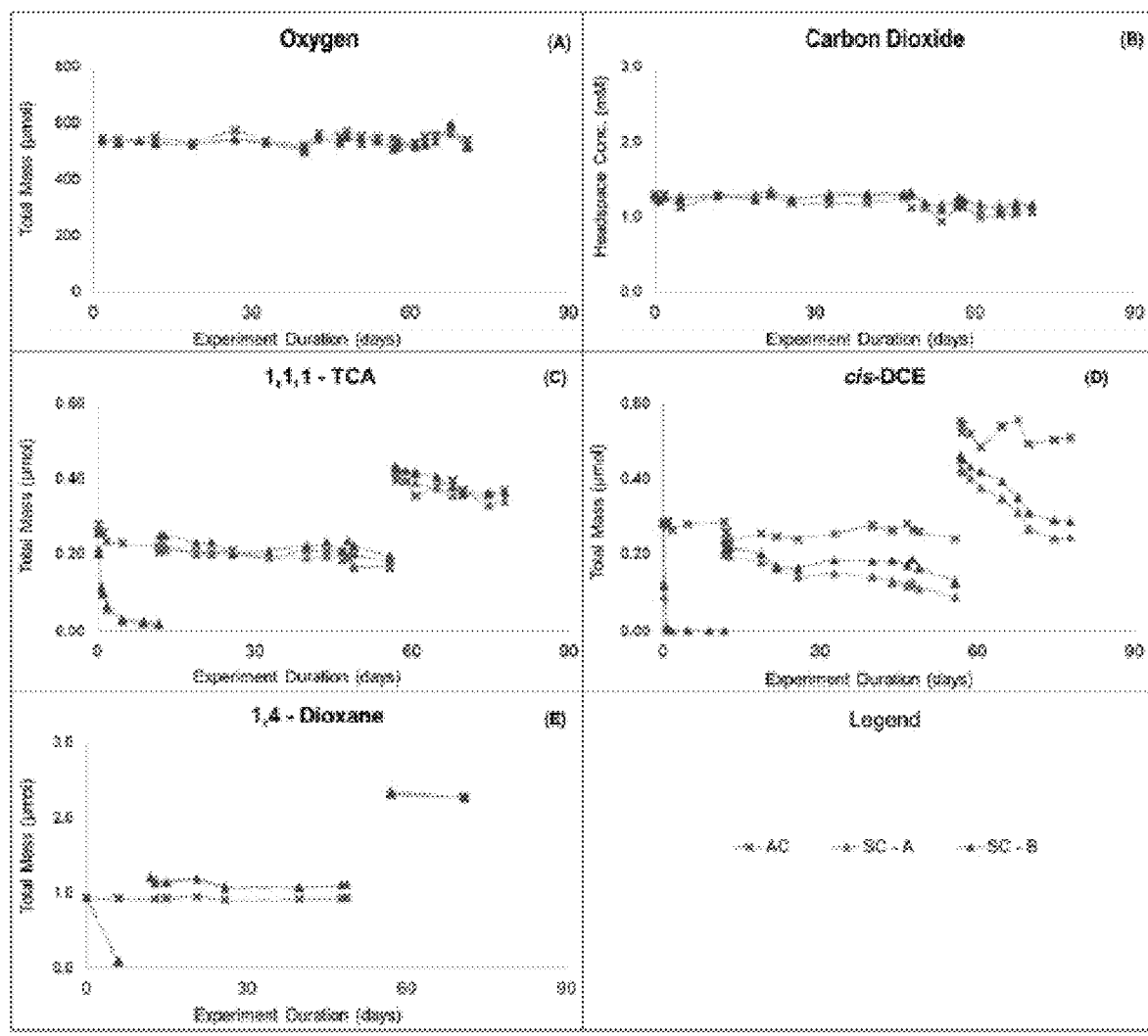
FIG. 33 provides data concerning total mass (µmol) versus time for control (suspended cells) reactor respiration (A and B) and contaminant date (C-E).

Abiotic control reactors received a single addition of contaminants that was monitored over ~0.60 days. At ~60 days, contaminant masses were doubled in CET reactors to challenge cells ability to transform higher masses of contaminants. To follow these data the contaminant masses within control reactors were also doubled at ~60 days (FIG. 33). Long-term suspended cell remediation-control reactors (SC) were used as a control to provide information about the possible rate, duration, and capacity of CoC transformation by a microbial biomass equivalent to that encapsulated within beads, though with no access to substrates. FIG. 33. As seen in FIG. 33(C-E) suspended cells rapidly transformed the entire mass of all contaminants within the initial spike, however, transformation of successive contaminant spikes was not observed for 1,1,1-TCA or 1,4-D and drastically reduced for cis-DCE Suspended cells transformed a minimal percent of contaminants in both the second and third contaminant additions. Abiotic reactors behaved as expected, showing no change in initial contaminant masses, and upon addition of more contaminants at ~60 days, masses fluctuate but remained at ~twice the original values.

These data illustrate the transformation capacity of ATCC 21198 biomass added to suspended cell reactors was likely met after the first addition of contaminants, and without a growth substrate or an inducing compound within reactors, the cells were not able to maintain co-metabolic transformation activity. These reactors directly replicate suspended cell reactors. The contrast between suspended cell transformation duration and capacity observed within the two data may be due to possible differences within biomass growth conditions, where slight differences in growth conditions can cause a batch of cells to store more or less energy per weight of biomass. This may be the reason for higher transformation capacities observed within suspended cell reactors. However, suspended cell data provides a benchmark for comparison to co-encapsulated cell reactors (CET and CET2 treatments) in the following sections.

2. AT CC 21198 Co-Encapsulated with TBOS

Figure 34:
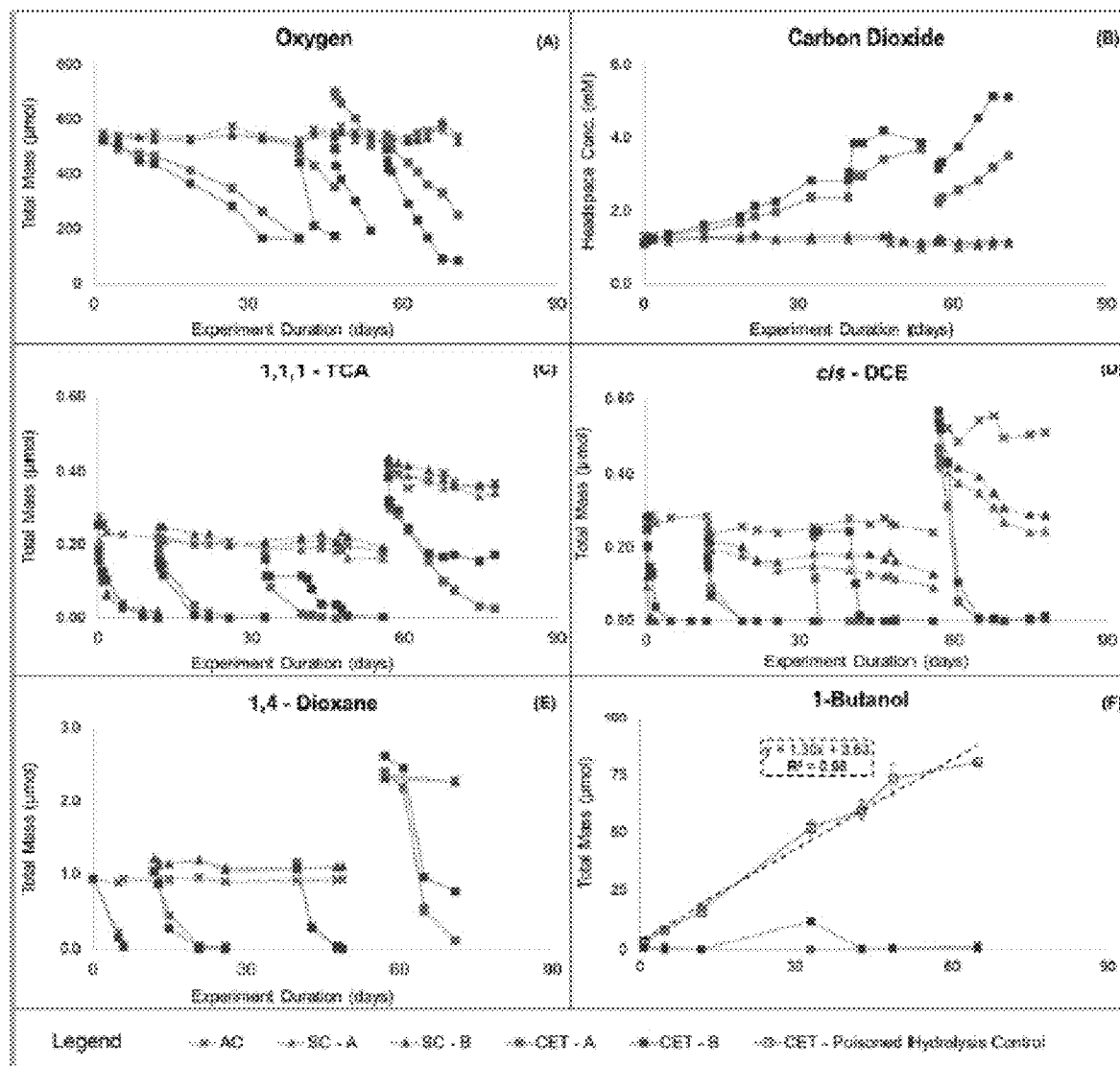
FIG. 34 provides data concerning total mass (µmol) versus time for TBOS co-encapsulated co-metabolic transformation longevity studies.

FIG. 34 presents respiration data ($O_2$ $CO_2$), cometabolic transformation data (1,1,1-TCA/cis-DCE/1,4-D), and substrate data (1-butanol) collected for CET reactors A and B along with control reactor data collected during the same period. FIG. 34(A-B) contain respiration data. As in previous experiments when Oz was depleted, due to cellular respiration, the headspace oxygen was refreshed to ensure co-metabolism proceeded. Breaks in timeseries connection lines signify times at which $O_2$ additions were made to reactors. It is apparent from the repetitive decrease in $O_2$ and constant increase in $CO_2$ within CET reactors in comparison to suspended control reactors that cellular respiration is occurring within CET reactors. Though additions of $O_2$ were consistently made to CET reactors to maintain aerobic conditions, reactor CET-B went anoxic around day 30-45 and after day 65 (FIG. 34). The lack of $O_2$ caused transformation to cease during these periods (FIG. 34). In FIG. 34. $CO_2$ data are presented in terms of measured headspace concentrations due to speciation of $CO_2$ in the aqueous phase as carbonates and the lack of pH measurements throughout the experiment. Four additions of the chosen CoC mixture were made to CET reactors, three at standard aqueous concentrations FIG. 34 and one with double concentrations made on days 0, 12, 33, and 57, respectively (FIG. 34). FIG. 34 presents abiotic 1-butanol production data collected for poisoned co-encapsulated TBOS beads, signified by open data points with red connecting lines, superimposed over measurements of 1-butanol within active CET.

FIG. 34 provides information concerning TBOS co-encapsulated cell cometabolic transformation longevity study: (A-B) respiration data, $O_2$ measurements reported at ~180 μmol are assumed to be near zero due to vacuum created within reactors. (C-E) Contaminant transformation data. Breaks in time-series connection lines signify successive additions. (F) TBOS 1-butanol production data. Data points with error bars are averages between duplicate reactors and errors bars are 95% confidence intervals. (AC)—Abiotic control. (SC)—Suspended cell control reactors. (CET) Cells co-encapsulated with 8% (w/w) TBOS. Alphabetical designations (A,B,C) are used to signify replicate reactors. AC has a single reactor; SC and CET treatments have duplicate reactors.

3. Respiration Data

Respiration data collected for CET reactors suggest that microbes are highly active in comparison to suspended cell reactors, as shown by gradual $O_2$ depletion over the first ~40 days followed by continued utilization of successive additions of $O_2$ made on days 40, 47, and 57 (FIG. 34A-B). The first and second additions of $O_2$, on days 40 and 47, were made via injection of pure $O_2$ to CET reactor headspaces through septa. For the last headspace refresh at ~57 days all reactors including controls were opened to alleviate any vacuum created by repeated gas sampling, and to reduce headspace $CO_2$ concentrations within CET reactors a reduction of $CO_2$ headspace concentration in CET reactors can be seen at 57 days (34B).

The rate at which $O_2$ was utilized within CET reactors increased by 3-7 times from the initial observed rate to the rate observed after the first addition of $O_2$, however, in subsequent additions, the rate remained fairly constant (Table 17). The observed increase in $O_2$ consumption rate indicates that microbial growth likely occurred within CET reactors and the following plateauing of rates in subsequent additions suggests a pseudo steady-state biomass level may have been reached within reactors. With unlimited $O_2$ supply the linear substrate production rate of encapsulated TBOS will control the microbial population and oxygen consumption rate by providing a slow but steady source of substrate.

Table 17 provides $O_2$ utilization rates within CET reactors calculated via linear regression of time-series data presented in FIG. 34A. Method of $O_2$ addition to CET reactors presented

TABLE 17

| $O_2$ Addition | Method | Time of Addition (days) | Estimated $O_2$ Utilization Rate (µmol/day) | |
| --- | --- | --- | --- | --- |
| | | | CET-A | CET-B |
| 0 | Initial $O_2$ | 0 | 6.0 | 9.2 |
| 1 | Pure $O_2$ Addition 1 | 40 | 18.6 | 38.1 |
| 2 | Pure $O_2$ Addition 2 | 47 | 23.1 | 40.5 |
| 3 | Atmosphere Headspace Equilibration | 57 | 18.3 | 34.5 |

The observed $O_2$ utilization in CET reactors is due to cellular utilization of 1-butanol released from the hydrolysis of encapsulated TBOS. The elevated $O_2$ consumption rate observed for CET reactor B in comparison to CET-A is assumed to be due to a greater 1-butanol release rate within reactor B. One line of evidence confirming that the production of 1-butanol from encapsulated TBOS is driving $O_2$ utilization within CET reactors is the comparison between oxygen and substrate data in FIG. 34 (A and F), where just after ~30 days, reactor CET-B went anoxic. The anoxic period in reactor CET-B can be seen by the stagnant $O_2$ data at ~30 days, which was also observed to hinder transformation of contaminants in this reactor at this time. Just after the reactor went anoxic 1-butanol was measured and detected at an elevated mass in solution. After $O_2$ was refreshed 1-butanol decreased back below the detection limit, providing evidence that $O_2$ utilization within these reactors is due to cellular oxidation of 1-butanol released from encapsulated TBOS (FIGS. 34A and F).

Stoichiometric analyses were used to provide another line of evidence confirming that $O_2$ consumption and $CO_2$ production was due to cellular utilization of 1-butanol released from TBOS. Using the measured mass of $O_2$ consumed within CET reactors at ~70 days, an estimate was made of the amount of 1-butanol that could have been oxidized to $CO_2$ and water. The estimated mass of 1-butanol oxidized was compared to the mass of 1-butanol that would be predicted to accumulate in reactors based on measured abiotic hydrolysis rates for gellan gum encapsulated TBOS and presented over active reactor data in FIG. 34F (Table 18). Table 18 provides estimated mass of 1-butanol consumed based on stoichiometric relationship of 1-butanol oxidation to $CO_2$ and water using measured amount of $O_2$ utilized versus the amount of 1-butanol that would be predicted to be released by measured abiotic production rates.

TABLE 18

| Predicted Butanol Consumption (µmol) | | Predicted Butanol Production (µmol) |
| --- | --- | --- |
| CET-A | CET-B | |
| 156.6 | 220.5 | 92 |

The predicted amount of 1-butanol consumed within reactors CET A and B, as estimated by the amount of $O_2$ utilized at 70 days, are on average ~2 times greater than the amount of 1-butanol that would be predicted to have hydrolyzed at 70 days based on the modeled abiotic linear rate (Table 18).

The elevated oxygen utilization within these reactors may be due to increased release of 1-butanol from microbial enzymatic hydrolysis of encapsulated TBOS. Certain microbes are capable of biotically hydrolyzing orthosilicate compounds in order to access the attached alcohols more quickly than abiotic processes allow. Even if TBOS is hydrolyzing at double the rate estimated in abiotic reactors, calculations indicate that the mass of encapsulated TBOS could still provide substrates for over 2 years.

A competing theory for the elevated $O_2$ utilization and $CO_2$ production in CET reactors, in relation to amount of 1-butanol that is predicted to have been produced by abiotic hydrolysis rates, is that encapsulated cultures respire more oxygen per mass of substrate than suspended cultures. However, in either case, oxygen is being consumed rapidly due to 1-butanol release, which for this technology to be successful should translate to growth of induced microbial cells capable of transforming large quantities of contaminants.

From respiration data in CET reactors it is apparent that the biomass is active and TBOS hydrolysis is supporting elevated microbial populations. CoC mixture data illustrate that observed microbial activity translated into high levels of cometabolic transformation activity (FIG. 34C-E). To date CET reactors have received and transformed 4 additions of CoCs. 3 at standard masses and one double mass addition— in contrast, suspended cell control reactors that contained a similar initial biomass have transformed only a single addition of CoCs.

As seen in FIG. 34(C-E), transformation rates within CET reactors of 1,1,1-TCA, cDCE and 1,4-D have not slowed appreciably in comparison to the initial transformation rates observed. In comparison to suspended cells, ATCC 21198 utilizing 1-butanol released from co-encapsulated TBOS has maintained much greater cometabolic activity over the 3 month period. The lag in contaminants transformation observed in reactor CET-B just after the third contaminant addition, ~30 days was when this reactor was anoxic. The absence of $O_2$ is consistent with the observed lack of transformation of CoCs. After the addition of $O_2$~45 days, CoC transformation proceeds at rates similar to reactor CET-A.

The observations of retained transformation rates and continued cellular activity suggest that co-encapsulated cultures utilizing 1-butanol released from encapsulated TBOS are able to maintain cellular populations similar to or greater than what was added to reactors, and that cells growing on low concentrations of 1-butanol are able to produce and maintain cometabolic enzymes. Previous data have suggested that growth of ATCC 21198 on 1-butanol does not induce cometabolic enzymes s. However, similar studies have provided evidence that cometabolic enzymes may be induced by the presence of contaminants themselves and potentially by a starvation mechanism within cells[515,2] Induction through starvation may be due to cellular upregulation of non-specific monooxygenase enzymes in an attempt to scavenge any available carbon. The data collected in CET reactors indicate that 1-butanol aqueous concentrations are kept low by immediate cellular utilization and the relatively slow hydrolysis of TBOS. The cometabolic activity of ATCC 21198 is maintained while the aqueous concentrations of 1-butanol are low. This may suggest that cells are induced by a pseudo-starvation mechanism.

Cellular utilization of co-encapsulated SRC products increased cell survivability overall activity, and contaminant transformation capacity of initially augmented biomass over a period of ~70 days. In conclusion, these results provide initial evidence that coencapsulation of cometabolizing cultures and LNAPL SRCs that produce alcohols provide long-term cometabolic activity.

4. ATCC 21198 Co-Encapsulated with T2BOS

Figure 35:
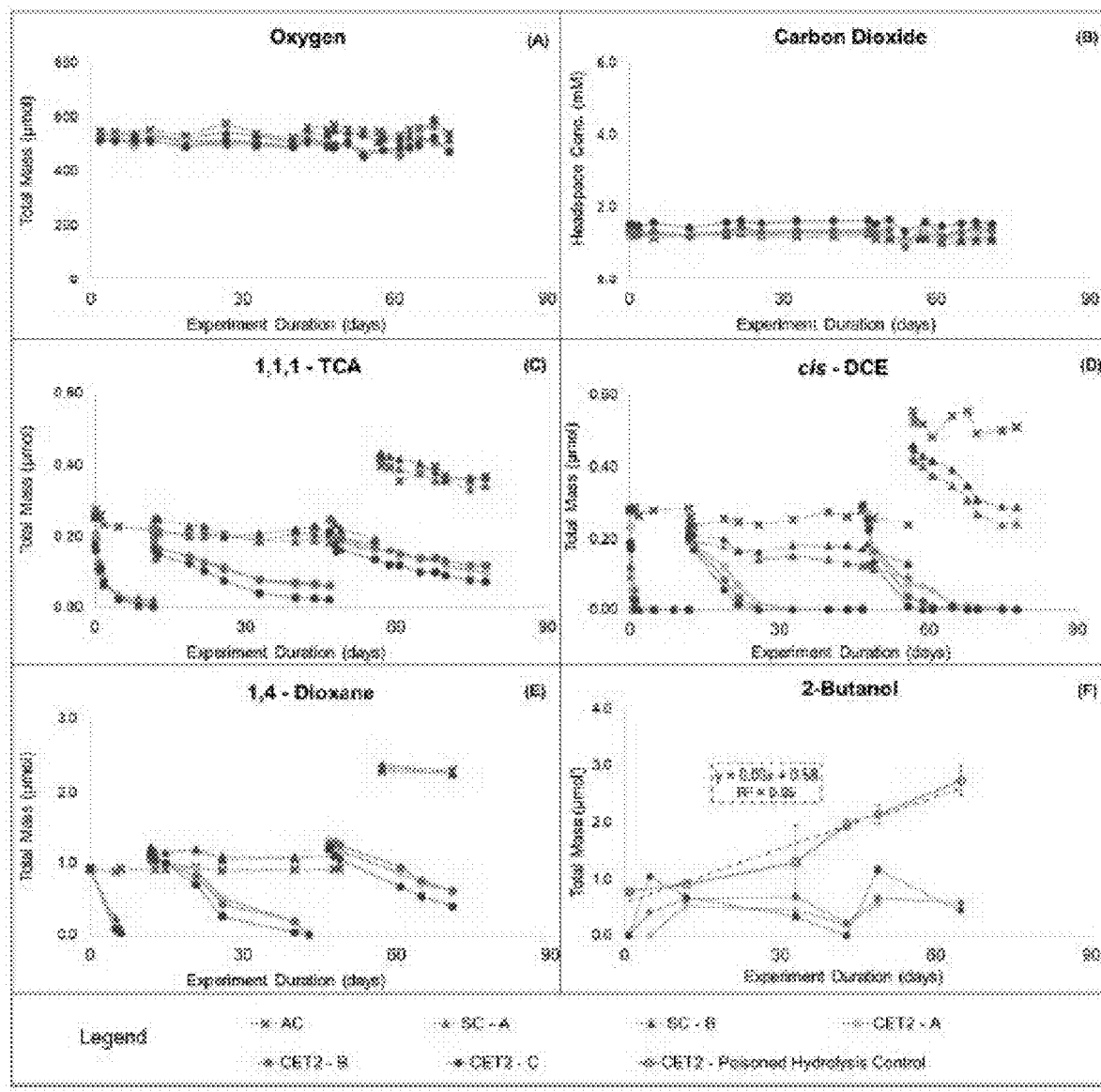
FIG. 35 provides data concerning total mass (µmol) versus time for T2BOS co-encapsulated with ATCC 21198 co-metabolic transformation longevity studies.

FIG. 35 provides respiration data ($O_2/CO_2$), cometabolic transformation data (1,1,1-TCA/cis-DCE/1,4-D), and substrate data (1-butanol) collected for $CET_2$, reactors A, B, and C along with control reactor data collected during the same period. FIG. 35(A-B) contain respiration data. Unlike CET reactors, CET2 reactors do not appear to be more active than suspended cell controls, and therefore, no additions of $O_2$ were made to the headspaces of CET2 reactors. In FIG. 35(B). $CO_2$ data are presented in terms of measured headspace concentrations due to speciation of $CO_2$ in carbonate system in the aqueous phase and lack of pH measurements throughout experiment. CET2 reactors received three additions of the chosen CoC mixture at standard concentrations similar to CET reactors, on days 0, 12, and 47 (FIG. 35C-E). FIG. 35(F) presents abiotic 2-butanol production data collected for poisoned co-encapsulated TBOS beads, signified by open data points with red connecting lines, superimposed over measurements of 2-butanol in solution within active CET2 reactors.

FIG. 35 concerns a $T_2BOS$ Co-Encapsulated Cell Cometabolic Transformation Longevity Study. (A-B) Respiration data. $O_2$ measurements reported at ~180 μmol are assumed to be near zero due to vacuum created within reactors. (C-E) Contaminant transformation data. Breaks in time-series connection lines signify successive additions. (F) Encapsulated $T_2BOS$ 2-butanol production data. Data points with error bars are averages between duplicate reactors and errors bars are 95%, confidence intervals. (AC)—Abiotic control. (SC)—Suspended cell control reactors. ($CET_2$) Cells co-encapsulated with 8% (w/w) $T_2BOS$.

5. Respiration Data

Visual observation of the respiration data collected for $CET_2$ reactors show little to no evidence of increased cellular activity in relation to suspended or abiotic reactors over the entire ~70 day period (FIG. 35A-B). However, by calculating slopes from the linear regression of all data points in each time-series and averaging the calculated slopes within treatments, it was determined that, relative to suspended and abiotic controls. $O_2$ with $CET_2$ reactors has decreased and $CO_2$ has accumulated (Table 19). Table 19 provides averages of linear regression slopes for time-series 0-70 days in each treatment bounded by 95% confidence intervals. Positive $O_2$ utilization rate corresponds to a measured decrease in $O_2$ whereas, positive $CO_2$ production rates correspond to a measured increase in $CO_2$.

TABLE 19

| Treatment | Abbreviation | O2 Utilization Rate (Umol/day) | CO2 Production Rate (umol/day) |
| --- | --- | --- | --- |
| Abiotic Control | AC | −0.04 ± N/A | −3.25 ± N/A |
| Suspended Cell Remediation Control | SC | 0.09 ± 0.02 | −1.42 ± 0.27 |
| C-encapsulated $T_2BOS$/ATCC 21198 | $CET_2$ | 0.48 ± 0.003 | 1.37 ± 0.54 |

Though it did not appear, visibly, that $CET_2$ reactors were more active than either control treatments, the data presented in Table 19 provides evidence that respiration was occurring within CET; reactors. The contrast between CET and CET2 respiration data could have been predicted by the drastic difference in abiotic hydrolysis rates observed between TBOS and $T_2BOS$ (Table 15).

To support these findings, FIG. 35(F) shows that by ~70 days poisoned co-encapsulated $T_BBOS$ is predicted to have produced ~2.2 μmol of 2-butanol, which would require ~13 μmol of $O_2$ to oxidize it to $O_2$ and $H_2O$. From the predicted $O_2$ utilization rate estimated above, ~18 μmol of oxygen has been consumed in CET2 reactors at 70 days. The similarity between the measured $O_2$ consumption and 2-butanol production estimates suggests that the observed utilization of $O_2$ could be due to microbial consumption of 2-butanol being slowly hydrolyzed from encapsulated T2BOS. While this analysis indicates that some cellular activity is likely occurring within $CET_2$ reactors in comparison to suspended cell controls, the amount is minimal in comparison to cells in CET reactors, consuming 1-butanol released from co-encapsulated TBOS. Therefore, these data indicate that cell biomass has likely not increased in CET2 reactors but may have diminished due to endogenous decay exceeding cell growth with prolonged incubation.

6. Contaminant Transformation

Respiration data within the $CET_2$-treated reactors indicate that there is minimal cellular activity. However, three consecutive additions of the chosen CoC mixture have been added to and transformed by $CET_2$ reactors, all at levels similar to CET reactors. $CET_2$ reactors have degraded the majority of all contaminants added, with the exception of 1,1,1-TCA, which is known to have the lowest transformation rate of the mixture (FIG. 35C-E).

In contrast to suspended cells, upon addition of the second spike of contaminants. CET2 reactors continued to transform all CoCs at appreciable rates, whereas, suspended cells did not transform measurable amounts of 1,1,1-TCA or 1,4-D when compared to the abiotic control, though slow transformation of cDCE may be occurring in suspended cell reactors.

These data indicate that in $CET_2$, reactors, the presence of $T_2BOS$, and likely the slow release and consumption of 2 butanol, has increased encapsulated cell survivability and transformation capacity in comparison to suspended cells. This is likely due to the slow rate of release of the inducing primary growth substrate providing some energy for cellular growth or potentially cell and enzyme maintenance. In either case, the encapsulated cultures cometabolic transformation potential has been maintained for over 70 days with minimal increase in oxygen demand when compared with free suspended cells that lost the majority of cometabolic transformation potential prior to day 12. The low oxygen demand observed in $CET_2$ reactors, in comparison to the mass of contaminants transformed, is a very positive outcome, since $O_2$ will likely be the limiting factor in contaminated aquifers.

7. Co-Encapsulated TBOS and T2BOS Data Comparison

Figure 36:
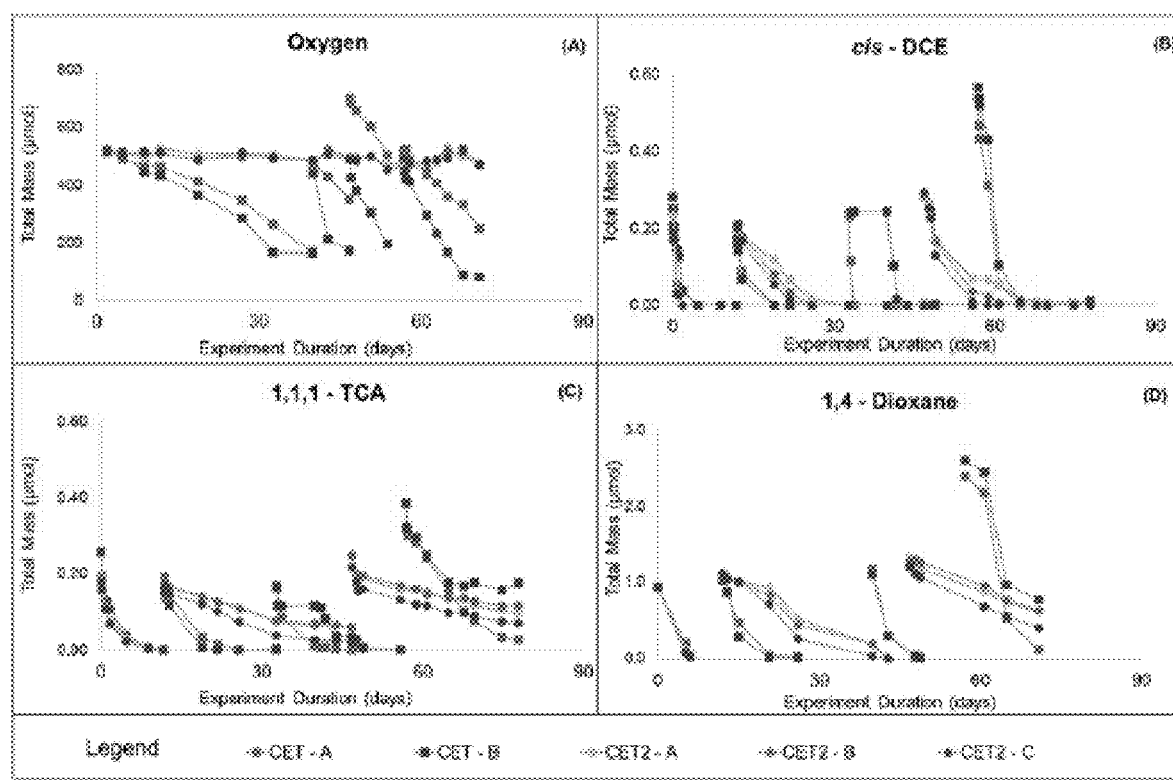
FIG. 36 data concerning total mass (µmol) versus time for TBOS and T2BOS co-encapsulated with ATCC 21198 co-metabolic transformation longevity studies.

ATCC 21198 co-encapsulated with TBOS showed highly elevated levels of cellular respiration, which corresponded directly to a large increase in cometabolic transformation capacity of the initially augmented biomass. Transformation capacities of cells in CET reactors were at least 4 times greater than cells suspended directly in media (Table 20). In addition, it was observed that CET reactors did not experience any appreciable decrease in transformation rates in successive contaminant spikes, as was seen in suspended and encapsulated cell reactors without SRCs (FIG. 36).

A period of anoxic conditions in reactor CET-B provided evidence that cellular respiration was due to microbial consumption 1-butanol, produced through the hydrolysis of encapsulated TBOS. Also, the increase in rate at which oxygen was consumed in consecutive additions indicated microbial biomass growth. $O_2$ utilization rates did visibly plateau after the second $O_2$ addition, which was likely controlled by the hydrolysis rate of encapsulated TBOS. Also, it was shown that TBOS was likely hydrolyzing more quickly within active reactors than in abiotic reactors, and as such the conclusion was drawn that ATCC 21198 may have the ability to biotically hydrolyze TBOS.

ATCC 21198 co-encapsulated with $T_2BOS$ showed only very slight increases in cellular respiration in comparison to suspended cells, and, not nearly to the same degree as TBOS co-encapsulated cells (Table 20).

TABLE 20

| Treatment | Estimated Butanol Produced (μmol) | Estimated Oxygen Consumed (μmol) | Total Mass of Contaminant Transformed (μmol) | | |
|---|---|---|---|---|---|
| | | | 1,1,1-TCA | cDCE | 1,4-Dioxane |
| AC - Abiotic Control | N/A | N/A | 0.13 | 0.09 | 0.02 |
| SC - Suspended Cell Controls | N/A | 6.3 | 0.36 | 0.49 | 1.03 |
| CET - Cells Co-encapsulated with TBOS | 91 | 1131.2 | 0.87 | 1.23 | 5.08 |
| $CET_2$ - Cells Co-encapsulated with $T_2BOS$ | 2.1 | 33.6 | 0.53 | 0.77 | 2.67 |

This results from the hydrolysis rate of encapsulated $T_2BOS$ being ~40 times less in comparison to encapsulated TBOS. In spite of the low amount of estimated substrate produced and minimal O2 utilized within $CET_2$ reactors, much higher transformation rates and capacities in $CET_2$ reactors were observed when compared to suspended cultures over the duration of this experiment (Table 20). Calculated transformation capacities of cells in $CET_2$ reactors were at least 2 times greater than suspended cells (Table 20). However, transformation rates in CET2 reactors were slower than in CET reactors. The observed slower transformation rates within CET2 reactors are less desirable than the higher transformation rates in CET reactors, however, an important consideration upon application of the designed technology will be oxygen mass consumed per mass of contaminant transformed.

FIG. 36 and Table 20 illustrate the contrast between contaminant transformation rates and capacities and oxygen consumption observed within CET and $CET_2$ reactors. CET reactors were able to transform ~2 times the amount of contaminants than $CET_2$ reactors were at ~70 days, though CET reactors consumed ~35 times the amount of oxygen. However, from FIG. 36 it is apparent from zero slowing in transformation rates over the ~70 day period that CET reactors could likely have transformed more contaminants than were added. Therefore, a direct comparison between the amounts of contaminants transformed to the amount of $O_2$ utilized between CET and CET; reactors may not be representative. However, the amount of $O_2$ consumed and contaminants transformed are presented in Table 20 to illustrate the contrast between the two co-encapsulation scenarios.

FIG. 36 provides information concerning a TBOS and $T_2BOS$ Co-Encapsulated Cell cometabolic transformation longevity study. (CET) cells w ere co-encapsulated with 8% (w/w) TBOS ($CET_2$) cells were co-encapsulated with 8% (w/w) $T_2BOS$. (A) Oxygen data contrasting CET and CET2 treatments. Reactor CET-B went anoxic from days 30-45 and from day 65 on, as seen in $O_2$ data. Lack of $O_2$ also caused transformation to cease during these periods. (B-D) provide contaminant transformation data. Four additions of CoC were made to CET reactors and three to $CET_2$ reactors. CET transformation rates are visibly greater. Break in time series connection lines signify successive additions.

Table 21 presents information concerning masses of contaminant transformed over a 70-day period. The mass of butanol produced was estimated based on measured poisoned encapsulated SRS reactors. $O_2$ consumption for AC, SC and $CET_2$ reactors was based on estimated $O_2$ utilization rates and is an average of the measured $O_2$ utilized in CET reactors. Total contaminant transformation masses are average measured values between treatments.

TABLE 21

| Treatment | Estimated Butanol Produced (μmol) | Estimated Oxygen Consumed (μmol) | Total Mass of Contaminant Transformed (μmol) | | |
|---|---|---|---|---|---|
| | | | 1,1,1-TCA | cDCE | 1,4-Dioxane |
| AC - Abiotic Control | N/A | N/A | 0.13 | 0.09 | 0.02 |
| SC - Suspended Cell Controls | N/A | 6.3 | 0.36 | 0.49 | 1.03 |
| CET - Cells Co-encapsulated with TBOS | 91 | 1131.2 | 0.87 | 1.23 | 5.08 |
| $CET_2$ Cells Co-encapsulated with $T_2BOS$ | 2.1 | 33.6 | 0.53 | 0.77 | 2.67 |

ATCC 21198 co-encapsulated with both model SRCs transformed greater masses of contaminants than suspended cells over the time periods tested (Table 20). Cells in CET reactors transformed ~4 times the total mass of CoCs as suspended cells, while $CET_2$ reactors transformed ~2 time the mass of contaminants as suspended cells. The greater transformation capacities were shown to be due to energy gained from cellular utilization of the slow hydrolysis of substrates from co-encapsulated SRCs. Also both systems have ample SRCs to continue to promote longer-term contaminant transformation.

Though both co-encapsulated treatments were observed to have retained much greater cometabolic transformation potential than suspended cultures, it was observed that cells co-encapsulated with TBOS maintained higher cometabolic transformation rates and transformed ~2 times the total mass of CoCs as cells co-encapsulated with T2BOS. However, cells co-encapsulated with TBOS required ~35 times more oxygen than cells co-encapsulated with T2BOS.

By including SRCs within an encapsulation matrix with co-metabolically active cultures, co-encapsulated cells are afforded additional benefits and many issues with current bioaugmentation techniques are mitigated. Co-encapsulated SRCs produce an exclusive controlled source of inducing growth substrate that support the co-encapsulated microbial populations, extend the remediation duration, and increase the transformation capacity of initially augmented cultures. In addition to supporting a targeted microbial species, including SRCs mitigated issues with current bioaugmentation methods that result in excess cellular growth, oxygen depletion, and the need for recurring low concentration injections of gaseous substrates.

After microbial encapsulation was optimized, methods were developed to encapsulate two model LNAPL SRCs, TBOS and T2BOS, in both alginate and gellan gum hydrogel beads. Mass loadings were achieved above what had been observed previously with other LNAPL oils, ~30%

(w/w) and ~8% (w/w) for alginate and gellan gum, respectively. Long-term experiments provided evidence that encapsulated SRCs could be held within beads for extended periods, over ~80 days, and abiotic hydrolysis experiments conducted with encapsulated SRCs, showed that after encapsulation hydrolysis rates of both TBOS and T2BOS were reduced by an order of magnitude in comparison to suspended SRCs. In addition to the observed reduction in hydrolysis rates after encapsulation, it was shown that the mass loading of LNAPL SRSs within beads might affect the rate at which encapsulated SRSs hydrolyze and produce substrates. It was found that TBOS encapsulated at 5% (w/w) hydrolyzed at twice the rate of TBOS encapsulated at 30% (w/w) (Table 12) indicating that it may be possible to tune the hydrolysis rate of encapsulated SRSs by adjusting the amount of SRS entrapped within beads.

The difference in hydrolysis rates between SRC compounds provides valuable controls over substrate production rates Engineered controls over substrate release alone might benefit current bioremediation techniques through the ability to make a single high concentration injection of SRs that would provide a long-term timed production of IGS. For example, it was predicted from the measured hydrolysis rates and an assumed bead mass loading of 10% SRC (w/w) that over 90 mg of cells could be generated and SRSs could provide substrates for several to hundreds of years. This demonstrates the potential for this technology to solve issues encountered with current growth substrates, such as the need for recurring injections of currently used gaseous substrates due to low solubility, excess cellular growth from injection of elevated concentrations of gaseous substrates and oxygen depletion due to excess cellular utilization of substrates.

One aspect of the present invention is that utilization of released 1- and 2-butanol from co-encapsulated TBOS and T2BOS increased the survivability, overall activity, and contaminant transformation rate and capacity of initially augmented biomass. However, differences in hydrolysis rates of the examined orthosilicate compounds led to the observation of a major tradeoff between the substrate production and utilization rate, oxygen demand, and cellular contaminant transformation capacities and rates. It was observed that higher substrate production rates could support greater microbial populations, which were able to transform contaminants at higher rates, though increased substrate utilization led to elevated oxygen demand. Oxygen is necessary but limited resource in the subsurface and upon application of this technology may be the limiting factor, and therefore, slower substrate production rates may prove to be more efficient in the long-term transformation of contaminants. The findings below highlight the important discoveries made during long-term co-encapsulation experiments.

Cells co-encapsulated with TBOS transformed each contaminant in a mixture of 1,1,1 TCA, cis-DCE, and 1,4-D at rates similar to initially augmented biomass for as long as ~70 days. For suspended cells, co-metabolic transformation potential was drastically reduced before ~12 days. Also, cells co-encapsulated with TBOS transformed ~4 times more contaminants that suspended cells after over 70 days, and could likely have transformed a higher mass of CoCs.

Cells co-encapsulated with T2BOS transformed each contaminant in a mixture of 1,1,1-TCA, cDCE, and 1,4-D at appreciable rates for as long as ~70 days. Transformation rates observed in cells co-encapsulated with T2BOS were not maintained as well as cells co-encapsulated with TBOS, however. T2BOS cells did transform ~2 times more contaminants than suspended cells after 70 days, and would continue to transform contaminants with continued incubation.

As seen from FIG. 34(A), alginate encapsulated cells had lagged initial substrate utilization rates just after encapsulation due to the encapsulation method used. However, it was determined that encapsulated cells retained ~55% of their initial substrate utilization rates after being in storage for as long as 18 weeks, whereas suspended cells substrate utilization rates were only 23% of initial values. These data illustrate that encapsulated cultures can be stored for extended periods of time and retain a majority of their original substrate utilization activity.

The amounts of contaminants transformed by suspended, alginate encapsulated, and gellan gum encapsulated cells appear to be visibly different, yet calculated transformation capacities for the three treatments are relatively similar. To determine if the transformation capacity between treatments were statistically different, the Microsoft Data Analysis tool kit was used to perform a single factor analysis of variance ANOVA test on calculated 1,1,1-TCA transformation capacities for each reactors. It was determined through these analysis that the transformation capacity for alginate encapsulated cells was statistically greater than that of both suspended and gellan gum encapsulated cells. Also, it can be seen that transformation capacities of suspended and gellan gum encapsulated cells do not differ significantly, p-value>>0.05.

Example 17

This example concerns a method for micro-encapsulating microbial cells in gellan gum. Gellan-gum pre-gel stock solution was made in a 200 mL volume of autoclaved 2 mM pH-7 phosphate buffered Nanopure water in a 250 mL Pyrex glass bottle. Gellan gum powder was added immediately after removing the solution from the autoclave to achieve a concentration of 0.75% (w/v). The pre-gel solution was shaken vigorously for 30 seconds and placed on a heated magnetic stir plate keeping the solution at ~85° C. while mixing at 200 rpm for 30 minutes. After complete hydration of GG powder, a known volume of pre-gel solution was transferred to a 50 mL Falcon tube. To initiate gelation an appropriate volume of 10% $CaCl_2$ stock solution was added to make a final concentration of 0.06% (w/v). The Falcon tube lid was replaced and the solution was vortexed for 30 seconds. The pre-gel solution was then left at room temperature to cool to ~60° C. at which time the pH was adjusted to seven with dilute NaOH, if necessary. The pre-gel solution was again left at room temperature to cool to ~45° C. before adding a known volume of concentrated cell slurry that was suspended in 50 mM phosphate buffer. At this point, the pre-gel solution was finalized and ready for complete gelation.

To form GG microspheres the pre-gel solution was added directly to an appropriate amount of heated canola oil, at ~45° C., to achieve a disperse phase volume fraction of 0.15. To increase emulsion stability Span-80 was added at 0.1% (v/v) and the entire solution was transferred to a 125 mL wide-mouth glass beaker (FIG. 22, Stage 1). The canola oil and pre-gel solution were then mixed with an IKA RW-20 digital overhead impeller mixer at 2500 rpm for 10 minutes (FIG. 22, Stage 2). The impeller blade was ~5 cm in diameter and was positioned ⅓ the way up from the bottom of the vial to the top of the liquid mixture.

To force gelation of emulsified GG droplets, the emulsified solution was transferred to an ice bath and cooled until the solution reached a temperature of 15° C. (FIG. 22, Stage 3). The canola oil and micro-bead mixture was stirred slowly at room temperature for 90 minutes to begin separation of micro-beads from canola oil. The mixture was then transferred to a 1 L beaker containing 500 mL of 0.25% (w/v) $CaCl_2$ solution to allow beads to partition into the aqueous phase and increase bead stability (FIG. 22, Stage 4). A large portion of canola oil was removed by aspiration. However, a separatory funnel was necessary to achieve complete separation (FIG. 22, Stage 5). Micro-beads were removed from the $CaCl_2$ solution using a vacuum pump fitted with a 1.2 um glass fiber filter and washed repeatedly with pH-7 carbonate buffered MSM. To calculate the final mass loading of cells in beads as $mg_{TSS}/g_{bead}$, assumptions were made that 1 mL of pre-gel solution would form 1 g of beads and that all cells added were encapsulated. Typically, microbially active beads were used for experimentation the day they were made; however, on occasion beads were stored overnight in a pH-7 carbonate buffered MSM at 4° C. Micro-beads made using the above method ranged in size from ~10-100 m in diameter, as determined through repeated bright field images taken with a Leica DM 2500 benchtop microscope.

Example 18

This example concerns a method for macro-encapsulating microbial cells in gellan gum, a 0.75% (w/v) GG pre-gel solution was prepared in autoclaved ~2 mM pH-7 phosphate buffered nanopure water at ~85° C. A $CaCl_2$ solution was added to the pre-gel solution to a final concentration of 0.06% (w/v) $CaCl_2$. The solution was allowed to cool to ~60° C. and the pH was adjusted to seven. The solution was then cooled to ~45° C. and cells were added. At this point the pre-gel solution was finalized and ready for gelation.

To create macro-beads from the warm pre-gel solution a 60 mL plastic syringe was used to draw the solution into an attached 1.5 m section of flexible rubber tubing with an inner diameter of ~2 mm. Other tubing sizes could be used to make larger or smaller macro beads. Once the tubing was filled with pre-gel solution, it was coiled and set on ice to cool to ~15° C. to finish gelation and completely solidify all gel within the tubing. After cooling to ~15° C., the gel-filled tubing was placed in a laminar flow hood for 60 minutes to provide extra time for internal crosslinking prior to extrusion of thin cylindrical sections of gel from the tubing. In the laminar flow hood, the hardened GG was pushed from the tubing onto long sections of Parafilm using the attached 60 mL syringe filled with air or a buffer solution. The extruded sections of hardened GG were ~2 mm in diameter by ~15-30 cm in length. A razor blade was used to cut the long sections into ~2 mm sections such that the height of each cylinder was approximately the same as the diameter.

The cylinders were allowed to cure for 10 minutes in the laminar flow hood before being transferred to a 1 L beaker containing 500 mL of 0.25% (w/v) $CaCl_2$ solution for 60 minutes. Microbially active macro-beads were separated from the external crosslinking solution using a vacuum pump fitted with a 70 mm plastic filter funnel. The filtered beads were washed three times with pH-7 carbonate buffered MSM and dried a final time using the vacuum pump. The final mass of beads was measured with minimal exogenous liquid and an assumption was made that all cells added to pre-gel solution were encapsulated. To calculate the final mass loading of cells in beads as $mg_{TSS}/g_{bead}$, assumptions were made that 1 mL of pre-gel solution would form 1 g of beads and that all cells added were encapsulated. Typically, microbially active beads were used for experimentation the day they were made; however, on occasion beads were stored overnight in pH-7 carbonate buffered MSM at 4° C.

Example 19

This example concerns a method for co-encapsulation of an SRC with microbial cells, such as 21198. Gellan gum pre-gel stock solution was made in a 200 mL volume of autoclaved 2 mM pH-7 phosphate buffered nanopure in a 250 mL Pyrex glass bottle. Gellan gum powder was added immediately after removing the solution from the autoclave to achieve a concentration of 0.75% (w/v). The pre-gel solution was shaken vigorously for 30 seconds and placed on a heated magnetic stir plate keeping the solution at ~85° C. while mixing at 200 rpm for 30 minutes. After complete hydration of gellan gum powder, a known volume of warm pre-gel solution, typically 40-50 mL, was transferred to a 125 mL wide mouth glass vial. Span-80 emulsifier was added to achieve a concentration of 0.1% (v/v). A known volume of liquid SRC was then added to the pre-gel solution and the mixture was emulsified using an IKA-RW 20 digital overhead impeller mixer at 2500 rpm for 10 minutes. Following emulsification, the pre-gel solution was heated back to ~80° C. and transferred to a 50 mL Falcon tube. To initiate gelation an appropriate volume of 10% $CaCl_2$ stock solution was added to make a final concentration of 0.06% w/v. The Falcon tube lid was replaced and the solution was vortexed for 30 seconds. The pre-gel solution was then left at room temperature to cool to ~60° C. before the pH was adjusted to seven with dilute NaOH, if necessary. If co-encapsulation of cells was desired, the pre-gel solution was again left at room temperature to cool to ~45° C. before adding a known volume of concentrated cell slurry that was suspended in 50 mM phosphate buffer. At this point, the pre-gel solution was finalized and ready for complete gelation.

To create macro-beads from the warm pre-gel solution a 60 mL plastic syringe was used to draw the emulsified SRC containing pre-gel solution from the Falcon tube into an attached 1.5 m section of flexible rubber tubing with an inner diameter of ~2 mm. Once the tubing was filled with pre-gel solution, it was coiled and set on ice to cool to ~15° C. to finish gelation and completely solidify all gel within the tubing. After cooling to ~15° C. the gel filled tubing was placed in a laminar flow hood for 60 minutes to provide extra time for internal crosslinking prior to extrusion of thin cylindrical sections of gel from the tubing. In the laminar flow hood, the hardened GG was pushed from the tubing onto long sections of Parafilm using the attached 60 mL syringe filled with air or a buffer solution. The extruded sections of hardened gellan gum were ~2 mm in diameter by ~15-30 cm in length. A razor blade was used to cut the long sections into ~2 mm sections such that the height of each cylinder was approximately the same as the diameter.

The cylinders were allowed to cure for 10 minutes in the laminar flow hood before being transferred to 1 L beaker containing 500 mL of 0.25% (w/v) $CaCl_2$ solution for 60 minutes. Microbially active macro-beads were separated from the external crosslinking solution using a vacuum pump fitted with a 70 mm plastic filter funnel. To rinse any exogenous SRCs from the surface of beads they were washed three times with a 0.1% (v/v) Tween-80 sterile microbe safe soap wash. Followed by rinsing three times with pH-7 carbonate buffered MSM and dried a final time using the vacuum pump. The final mass of beads was measured with minimal exogenous liquid and an assumption was made that all cells added to pre-gel solution were encapsulated. To calculate the final mass loading of cells in beads as $mg_{TSS}/g_{bead}$, assumptions were made that 1 mL of pre-gel solution would form 1 g of beads and that all cells added were encapsulated. Typically, microbially active beads were used for experimentation the day they were made; however, on occasion beads were stored overnight in pH-7 carbonate buffered MSM at 4° C.

To determine the SRC mass loading in beads as $g_{SRC}/g_{bead}$ and encapsulation efficiency of this process, two ~0.25 g samples of beads were taken and transferred into 27 mL vials containing 10 mL of 2 mM sodium citrate solution. These vials were heated to ~80° C. then placed on a shaker table shaking at 250 rpm for 120 minutes. Sodium citrate was used to chelate calcium and help break apart the gellan gum cylinders such that any encapsulated SRC was released into solution. Due to the increased stability of GG cylinders over alginate macrospheres, heating and excess physical agitation of gellan gum cylinders was required to ensure all encapsulated SRC was released.

The amount of released SRC was quantified using the DCM extraction method using the measured mass of SRC released and the known initial mass of beads broken down a mass loading could be determined. The process encapsulation efficiency, the percent of added SRC that was successfully encapsulated, was then determined from the measured mass loading ($g_{SRC}/g_{bead}$), the measured final mass of beads ($g_{bead}$) and the known mass of SRC added.

Example 20

This example concerns batch reactor experiments that were conducted to determine if ATCC 21198 co-encapsulated with SRCs, TBOS or T2BOS, could be maintained on SRC products, 1- and 2-butanol to achieve long-term cometabolic treatment of COCs. The cometabolism of a mixture of 1,1,1-TCA, cis-DCE, and 1,4-D were used as example COCs. Gellan gum was selected as the encapsulation matrix due to observed long-term durability. In earlier tests (not shown) ATCC 21198 was not observed to have the ability to consume GG, and the macro-beads remained stable for over 120 days while shaking at ~100 rpm on a shaker table, whereas, alginate macro-beads did not.

Cylindrical GG macro-beads containing ATCC 21198 and TBOS/T2BOS were created with biomass loadings of ~0.5 $mg_{TSS}/g_{bead}$ and SRC mass loadings of ~8% (w/w) SRC. Based on the results previously presented, we expected both SRCs to promote cometabolic treatment, with TBOS yielding higher rates of both metabolism and cometabolism. Two grams of beads were added to the batch reactors, to achieve final cell concentrations of ~10 $mg_{TSS}/L$ and SRC concentrations of ~1500 mg/L (FIG. 34). An abiotic control with no addition of beads ensured transformation of added CoCs was biotic. Suspended cell controls, illustrated the effect of co-encapsulation on initial and long-term cell viability, as measured via CoC transformation rates and capacities. Reactors were created in duplicate or triplicate. All reactors were spiked initially with the chosen CoC mixture at environmentally relevant aqueous concentrations, 1,1,1-TCA (~250 ppb), cis-DCE (~250 ppb), and 1,4-D (~800 ppb). All data are presented on a total mass basis within reactors calculated via Henry's law. Successive spikes of contaminants were made to reactors, over ~90 days, after the majority of contaminants were transformed. The concentration of subsequent spikes were doubled in an attempt to challenge cell transformation capacities. Respiration data ($O_2/CO_2$), substrate data (1-/2-butanol), and contaminant data (1,1,1-TCA/cis-DCE/1,4-D) were monitored as necessary.

A. ATCC 21198 Co-Encapsulated with TBOS

Figure 37:
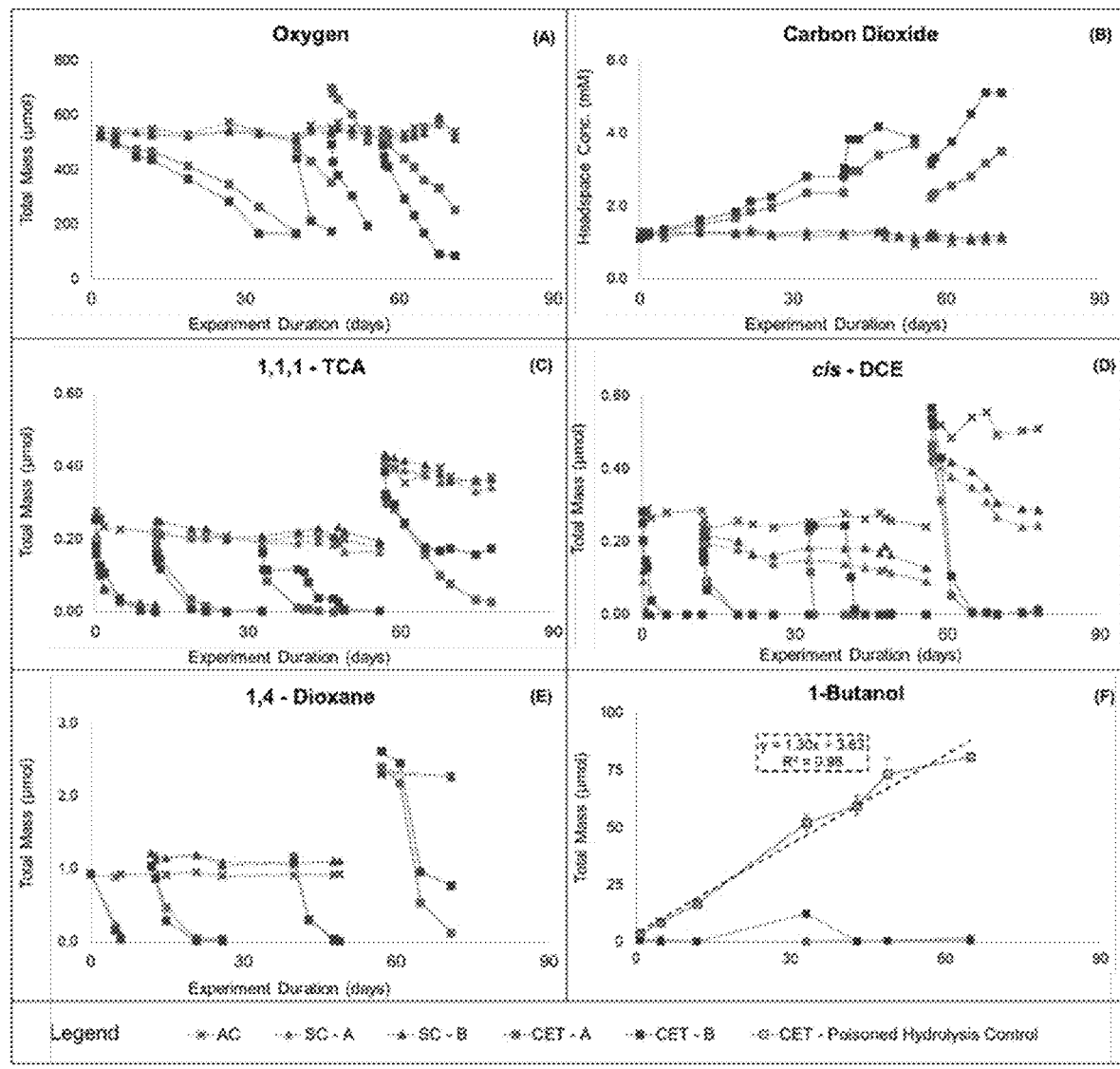
FIG. 37 presents respiration data ($O_2/CO_2$), cometabolic transformation data (1,1,1-TCA/cis-DCE/1,4-D), and substrate data (1-butanol) collected for reactors A and B (co-encapsulated with TBOS and 21198) (CET) along with control reactor data.

FIG. 37 presents respiration data ($O_2/CO_2$), cometabolic transformation data (1,1,1-TCA/cis-DCE/1,4-D), and substrate data (1-butanol) collected for reactors A and B (co-encapsulated with TBOS and 21198) (CET) along with control reactor data. FIG. 37(A-B) contains the respiration data. As in previous experiments when $O_2$ was depleted, due to cellular respiration, the headspace $O_2$ was refreshed to ensure cometabolism proceeded. Breaks in timeseries connection lines signify times when $O_2$ additions were made to reactors. It is apparent from the repetitive decrease in $O_2$ and constant increase in $CO_2$ within CET reactors, in comparison to suspended control reactors, that cellular respiration was occurring in the CET reactors. Though additions of $O_2$ were consistently made to CET reactors to maintain aerobic conditions, reactor CET-B went anoxic around day 30-45 and after day 65 (FIG. 37A). The lack of $O_2$ caused transformation to cease during these periods (FIG. 37C). In FIG. 37(B), $CO_2$ data are presented based on the measured headspace concentration. The results represent four additions of the CoC mixture to CET reactors, three at similar aqueous concentrations on days 0, 12, 33 and one at double concentration on day 57 (FIG. 37C-E). FIG. 37(F) also presents abiotic 1-butanol production data collected for poisoned co-encapsulated TBOS beads.

Respiration data from the CET reactors indicates the encapsulated microbes are highly active in comparison to suspended cell reactors, as shown by the $O_2$ depletion over the first ~40 days followed by continued utilization of successive additions of $O_2$ made on days 40, 47, and 57 (FIG. 37A-B). The first and second additions of $O_2$, on days 40 and 47, were made via injection of pure $O_2$ to CET reactor headspace through septa. For the headspace refresh at ~57 days all reactors including controls were opened to alleviate any vacuum created by repeated gas sampling, and to reduce headspace $CO_2$ concentrations within CET reactors. A reduction of $CO_2$ headspace concentration in CET reactors can be seen at ~57 days (FIG. 37B).

The rate at which $O_2$ was utilized within CET reactors increased by 3-7 times from the initial observed rate, however, in subsequent additions, the rate remained fairly stable. The observed increase in $O_2$ consumption rates indicates that microbial growth likely occurred within CET reactor beads and the following plateauing of rates in subsequent additions suggests a pseudo steady-state biomass level may have been reached. With unlimited $O_2$ supply the linear substrate production rate of encapsulated TBOS will control the microbial population and oxygen consumption rate by providing a slow but steady source of substrate.

The observed $O_2$ utilization in CET reactors is due to cellular utilization of 1-butanol released from the hydrolysis of encapsulated TBOS. Of note is the elevated $O_2$ consumption rate observed for CET reactor B in comparison to CET reactor A. This is possibly due to a greater 1-butanol release rate within reactor B. This is difficult to confirm because measurements of 1-butanol within active reactors were typically below the detection limit likely due to highly active microbial communities immediately consuming released 1-butanol (FIG. 37F).

One line of evidence confirming that the production of 1-butanol from encapsulated TBOS is driving $O_2$ utilization within CET reactors is the comparison between oxygen and substrate data in FIG. 37 (A and F), when just after ~30 days, reactor CET-B went anoxic. The anoxic period in reactor CET-B can be seen by the level $O_2$ data at ~30 days, which was also observed to hinder transformation of contaminants in this reactor at this time. Note that due to the vacuum that develops in the reactor, and the method of sampling used, a reported $O_2$ mass of 180 µmol represents anoxic conditions in the reactors. Just after the reactor went anoxic, 1-butanol was measured and detected at an elevated mass in solution. After $O_2$ was refreshed 1-butanol decreased back below the detection limit, providing evidence that $O_2$ utilization within these reactors is due to cellular oxidation of 1-butanol released from encapsulated TBOS (FIGS. 37A and F).

Stoichiometric analysis provided another line of evidence confirming that $O_2$ consumption and $CO_2$ production was due to cellular utilization of 1-butanol released from TBOS. Using the measured mass of $O_2$ consumed within CET reactors at ~70 days, an estimate was made of the amount of 1-butanol that could have been oxidized to $CO_2$ and $H_2O$. The estimated mass of 1-butanol oxidized was compared to the mass of 1-butanol that would be predicted to accumulate in reactors based on measured abiotic hydrolysis rates for gellan gum encapsulated TBOS. The predicted amount of butanol consumption was 157 and 221 µmol for the CET-A and the CET-B reactors respectively, while the amount based on the abiotic hydrolysis was 92 µmol. The rates in the biotic reactors were about twice that of the abiotic control. The elevated oxygen utilization within these reactors may be due to increased release of 1-butanol from microbial enzymatic hydrolysis of encapsulated TBOS. Previous research has shown that a mixed culture of microorganisms were capable of biotically hydrolyzing orthosilicate compounds in order to access the attached alcohols more quickly than abiotic processes allow. Even if TBOS is hydrolyzing at double the rate estimated in abiotic reactors, calculations indicate that the mass of encapsulated TBOS could still provide substrates for over 2 years.

From respiration data in CET reactors it is apparent that the biomass is active and TBOS hydrolysis is supporting elevated microbial populations. COC mixture data illustrate that observed microbial activity translated into high levels of cometabolic transformation activity (FIG. 37C-E). The CET reactors received and transformed 4 additions of COCs, 3 at standard masses and one double mass addition; in contrast, suspended cell control reactors that contained a similar initial biomass have transformed only a single addition of COCs.

As seen in FIG. 37(C-E), transformation rates within CET reactors of 1,1,1-TCA, cis-DCE, and 1,4-D have not slowed appreciably in comparison to the initial transformation rates observed. In comparison to suspended cells, ATCC 21198 utilizing 1-butanol released from co-encapsulated TBOS has maintained much greater cometabolic activity over the 2 to 3 month period. Of note, is the lag in transformation of contaminants observed in reactor CET-B just after the third contaminant addition, ~30 days. As noted above, this is when this reactor was anoxic. The absence of $O_2$ is consistent with the observed lack of transformation of COCs. After the addition of $O_2$~45 days, COC transformation proceeds at rates similar to reactor CET-A.

The observations of maintained transformation rates and continued cellular activity suggest that co-encapsulated cultures utilizing 1-butanol released from encapsulated TBOS are able to sustain a cell population of 21198 similar to or greater the amount added to reactors, and that cells growing on low concentrations of 1-butanol are able to produce and maintain metabolic enzymes. The data collected in CET reactors indicate that 1-butanol aqueous concentrations are kept low by immediate cellular utilization and the relatively slow hydrolysis of TBOS. The cometabolic activity of ATCC 21198 is maintained while the aqueous concentrations of 1-butanol are low.

This experiment shows that cellular utilization of co-encapsulated SRC products increased cell survivability, overall activity, and contaminant transformation capacity of initially augmented biomass over a period reported here of ~70 days. Continued cometabolic activity for up to 260 days will be presented in FIG. 39.

ATCC 21198 Co-Encapsulated with $T_2BOS$

Figure 38:
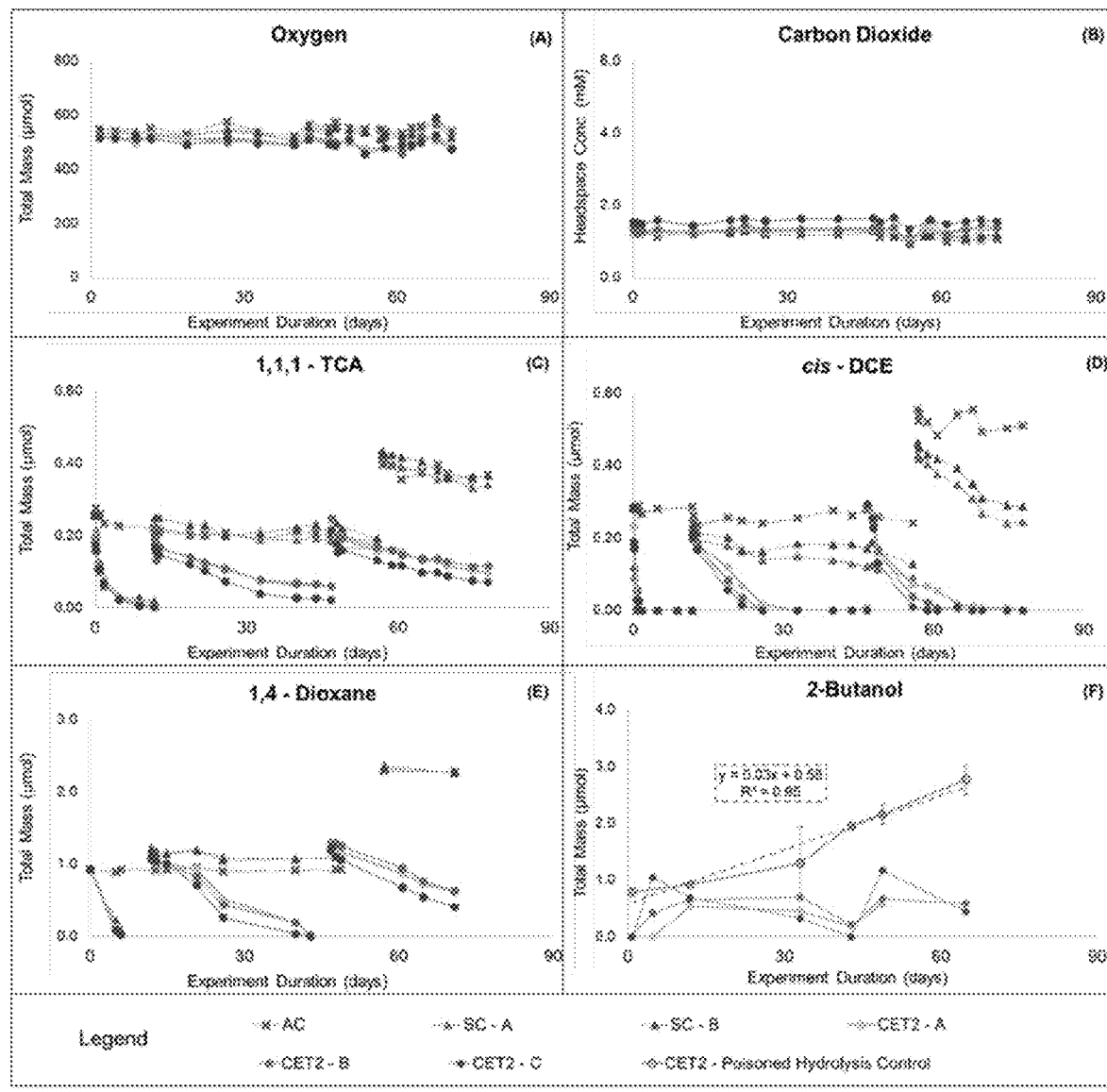
FIG. 38 presents respiration data ($O_2/CO_2$), cometabolic transformation data (1,1,1-TCA/cis-DCE/1,4-D), and substrate data (2-butanol) collected for CET2 reactors A, B, and C with GG beads encapsulated with T2BOS and 21198, along with control reactor data.

FIG. 38 presents respiration data ($O_2/CO_2$), cometabolic transformation data (1,1,1-TCA/cis-DCE/1,4-D), and substrate data (2-butanol) collected for CET2 reactors A, B, and C with GG beads encapsulated with T2BOS and 21198, along with control reactor data. Visual observation of the $O_2$ and $CO_2$ respiration data collected for CET2 reactors show little to no evidence of increased cellular activity in relation to suspended or abiotic reactors over the ~70 day period shown (FIG. 38A-B). However, the linear regression slopes of each time-series, shows differences relative to suspended and abiotic controls. $O_2$ with $CET_2$ reactors headspace has decreased (Table 22). The contrast between CET and CET2 respiration data could have been predicted by the difference in abiotic hydrolysis rates observed between TBOS and $T_2BOS$ (Table 14). The rate of $O_2$ utilization of 0.48 µmol/day in the CET2 reactors compares with 18 to mol/day for the CET reactors. The factor of 40 to 80 higher rate in the CET reactors is consistent with the 45 times higher rate of alcohol production (Table 14) compared to encapsulated T2BOS.

TABLE 22

Rates of oxygen consumption in the CET2 reactors.

| Treatment | Abbreviation | O2 Utilization Rate (umol/day) | CO2 Production Rate (umol/day) |
|---|---|---|---|
| Abiotic Control | AC | −0.04 ± N/A | −3.25 ± N/A |
| Suspended Cell Remediation Control | SC | 0.09 ± 0.02 | −1.42 ± 0.27 |
| C-encapsulated $T_2BOS$/ATCC 21198 | $CET_2$ | 0.48 ± 0.003 | 1.37 ± 0.54 |

To support these findings, FIG. 38(F) shows that by ~70 days poisoned co-encapsulated T2BOS is predicted to have produced ~2.2 µmol of 2-butanol, which would require ~13 mol of $O_2$ to oxidize it to $CO_2$ and $H_2O$. From the predicted $O_2$ utilization rate estimated above, ~18 mol of oxygen was consumed in $CET_2$ reactors at 70 days. The similarity between the measured $O_2$ consumption and 2-butanol production estimates suggests that the observed utilization of $O_2$ so due to microbial consumption of 2-butanol being slowly hydrolyzed from encapsulated T2BOS. While this analysis indicates cellular activity is occurring within CET2 reactors in comparison to suspended cell controls, the activity is much slower in comparison to the CET reactors.

Contaminant Transformation Observations

Respiration data within the CET2 treated reactors indicates that there is lower cellular activity compared to the CET reactors. However, three consecutive additions of the chosen COC mixture were added to and transformed in $CET_2$ reactors, all at levels similar to CET reactors. $CET_2$ reactors have transformed the majority of contaminants added, with cis-DCE most rapidly transformed and 1,1,1-TCA and 1,4-D more slowly transformed (FIG. 38C-E). In contrast to suspended cells, upon addition of the second spike of contaminants, CET2 reactors continued to transform all COCs at appreciable rates, whereas, suspended cells did not transform measurable amounts of 1,1,1-TCA or 1,4-D when compared to the abiotic control, though slow transformation of cis-DCE may be occurring in suspended cell reactors. These data indicate that in CET2 reactors, the presence of T2BOS, and likely the slow release and consumption of 2-butanol, has increased encapsulated cell survivability and transformation capacity in comparison to suspended cells. This is likely due to the slow rate of release of the inducing primary growth substrate providing some energy for cellular growth or potentially cell and enzyme maintenance. In either case, the encapsulated cultures cometabolic transformation potential is shown for over 70 days with minimal increase in oxygen demand when compared with free suspended cells that lost the majority of cometabolic transformation potential prior to day 12. The low oxygen demand observed in CET2 reactors, in comparison to the mass of contaminants transformed, is a very positive outcome, since $O_2$ is needed for the cometabolic transformation.

Long-Term Cometabolic Transformations in the CET and $CET_2$ Reactors

Figure 39:
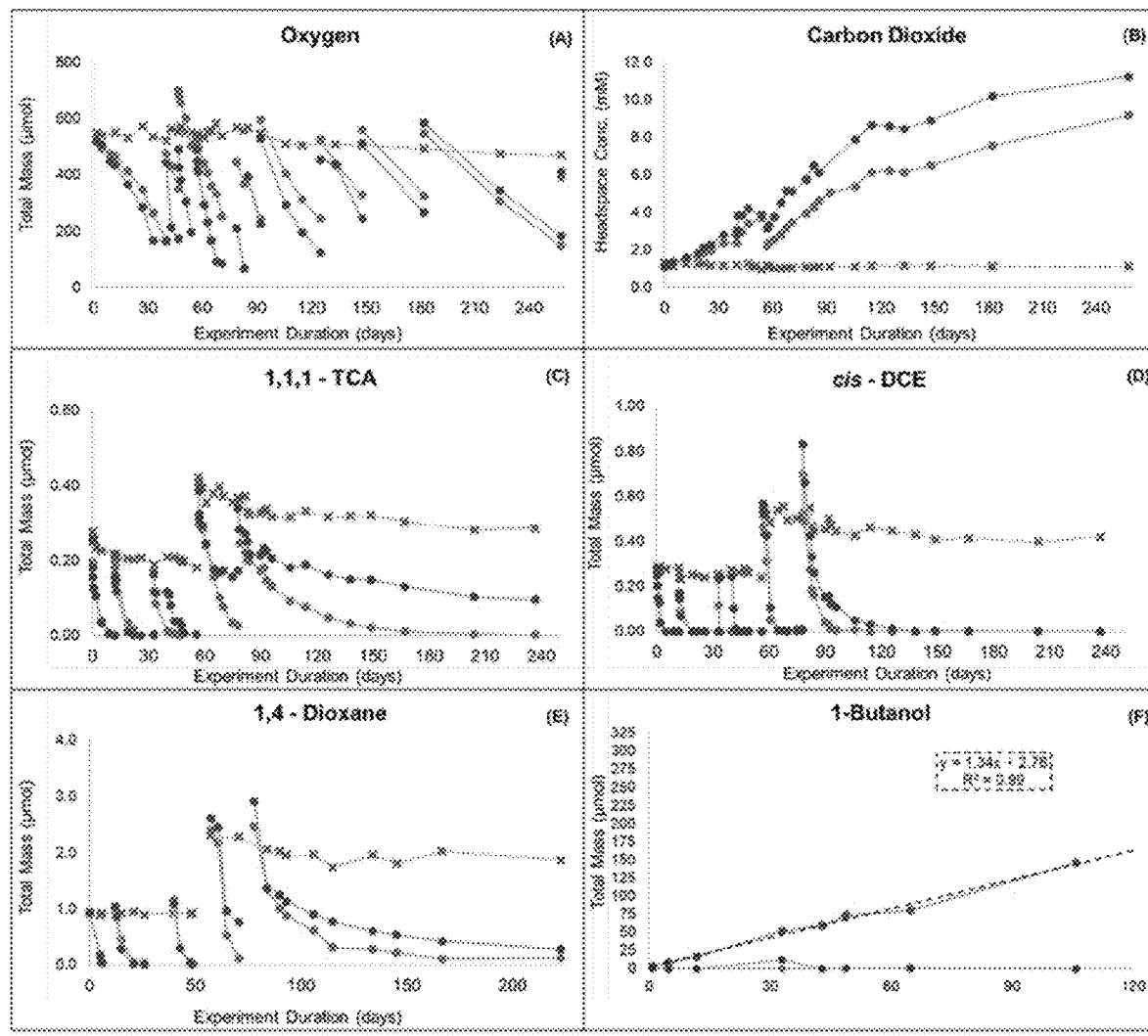
FIG. 39 presents a continuation of the monitoring of the TBOS/21198 (CET) beaded reactor of FIG. 37.

FIG. 39 presents a continuation of the monitoring of the TBOS/21198 (CET) beaded reactor shown in FIG. 37 for an incubation period of 260 days. $O_2$ continues to be depleted, due to cellular respiration, the headspace oxygen was added many times to ensure cometabolism proceeded. Breaks in timeseries connection lines signify times at which $O_2$ additions were made to reactors. It is apparent from the repetitive decrease in $O_2$ and constant increase in $CO_2$ within CET reactors. Five additions of the chosen COC mixture were made to CET reactors, three at standard aqueous concentrations and two with double concentrations made on days 0, 12, 33, 57, and 80, respectively (FIG. 39C-E). Respiration data collected for CET reactors suggest that microbes remain active over the 260 days shown, continued utilization of successive additions of $O_2$ made on days 40, 47, 57, 80, 100, 120, 150, 180 (FIG. 39A-B). The $O_2$ consumption results combined with the continued $CO_2$ production indicate microbial activity over the 260 day incubation period.

To date CET reactors have received and transformed 5 additions of COCs (6 of cis-DCE), 3 at the masses of the original addition and two at double mass addition; in contrast, suspended cell control reactors that contained a similar initial biomass have transformed only a single addition of COCs. The observations of maintained transformation abilities and continued cellular activity suggest that co-encapsulated cultures utilizing 1-butanol released from encapsulated TBOS are able to maintain cellular populations over 260 days. While there has been some slowing in rates at later time, cometabolism has continued.

Figure 40:
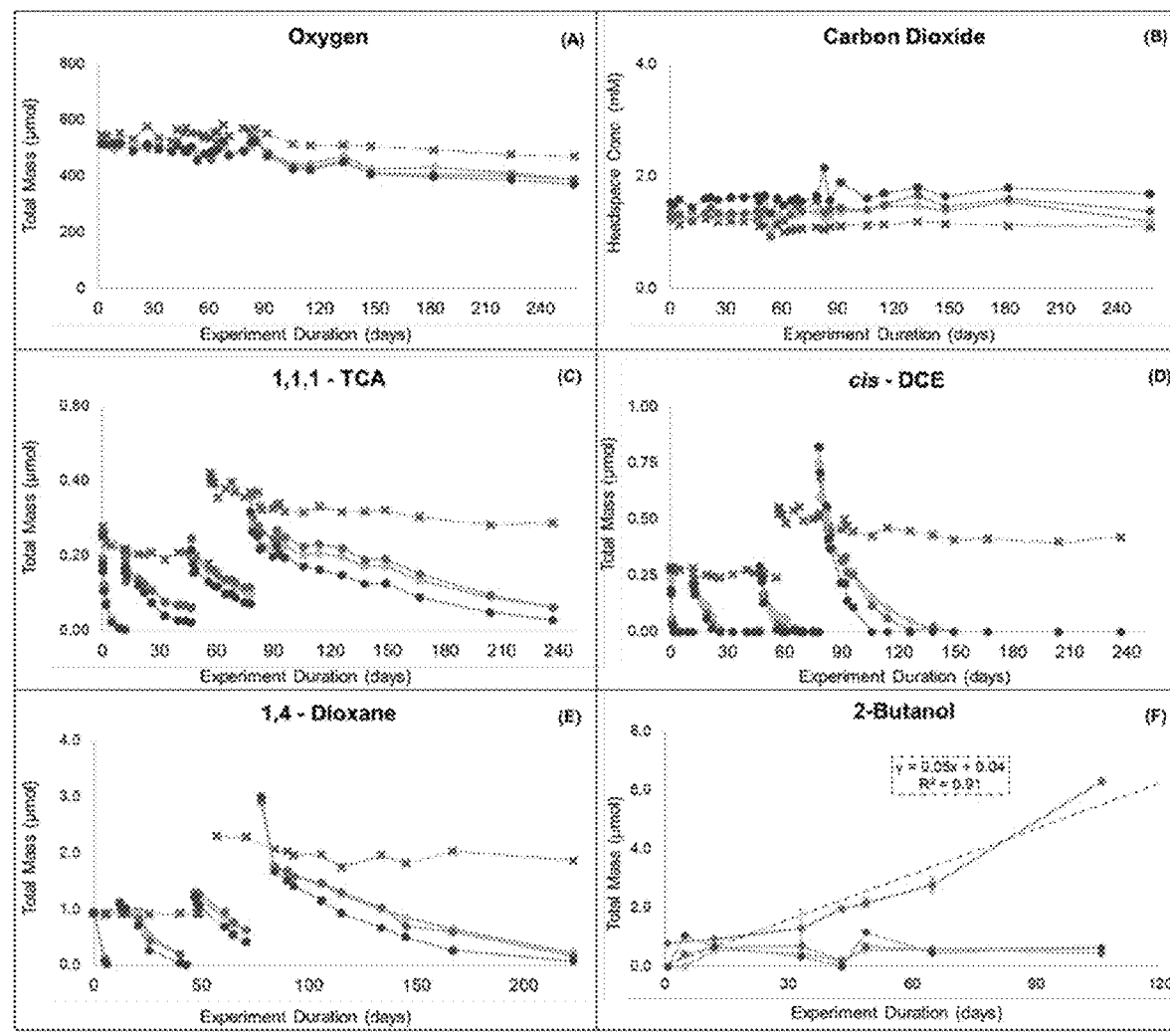
FIG. 40 presents a continuation of the respiration data ($O_2/CO_2$), cometabolic transformation data (1,1,1-TCA/cis-DCE/1,4-D), and substrate data (2-butanol) collected for $CET_2$ reactors A, B, and C along with control reactor data.

FIG. 40 presents a continuation of the respiration data ($O_2/CO_2$), cometabolic transformation data (1,1,1-TCA/cDCE/1,4-D), and substrate data (2-butanol) collected for $CET_2$ reactors A, B, and C along with control reactor data. $CET_2$ reactors continued show very slow rates of $O_2$ consumption the extend time period, and therefore, no additions of $O_2$ were made to the headspaces of $CET_2$. $CET_2$ reactors received four additions of the chosen COC mixture. Visual observation of the respiration data collected for $CET_2$ reactors shows evidence of slow cellular activity over the 260 day incubation period (FIG. 40A-B) with continued $O_2$ utilization and $CO_2$ production compared to the control.

Four consecutive additions of the COC mixture have been added to and have been transformed by $CET_2$ reactors. $CET_2$ reactors have transformed the majority of the contaminants added. Of the three contaminants, cis-DCE is the most rapidly transformed followed by 1,4-D and then 1,1,1-TCA. The encapsulated cultures cometabolic transformation potential has been maintained for over 260 days at very slow rates of $O_2$ utilization.

VC and 1,1-DCE Transformation in the CET and CET2 Reactors

Figure 41A:
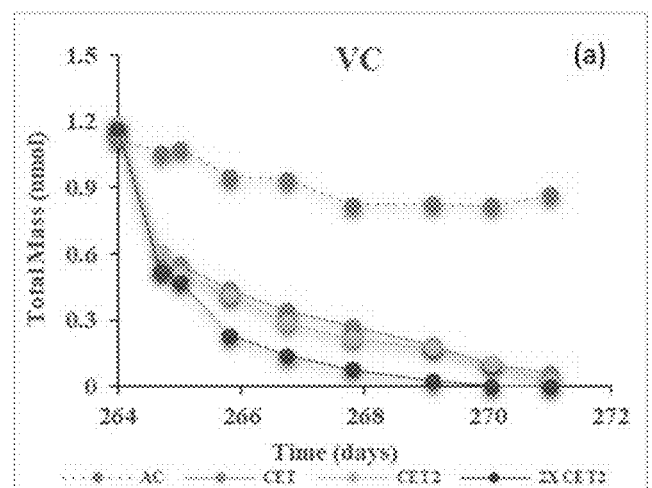
FIG. 41A, B presents information concerning VC (a) and 1,1-DCE (b) cometabolic transformation with TBOS and T2BOS co-encapsulated 21198 cells after long time (264 day) exposure to cis-DCE, 1,1,1-TCA, and 1,4D.

To examine the cometabolic activity in the reactors to other CoCs, vinyl chloride (VC) was added to the CET and $CET_2$ reactors on day 264 of the batch incubation. The results showed all the added VC was transformed within a week in the TBOS (CET) and T2BOS ($CET_2$) reactors (FIG. 41 a). The fastest rates were achieved in a reactor contained twice as many beads (2×) as the CET2 reactors previously presented. Our previous batch experiments showed that when 21198 was grown on isobutane, VC was transformed at a very high rate (about 14 µmol/mg TSS/day). This experiment demonstrated the encapsulated GG macrobeads could be an effective method to remediate dilute plumes of VC that result from the anaerobic transformation of TCE and PCE. Since cis-DCE is also effectively transformed in these batch reactors, dilute mixtures of cis-DCE and VC could be potentially treated in the field.

Figure 41B:
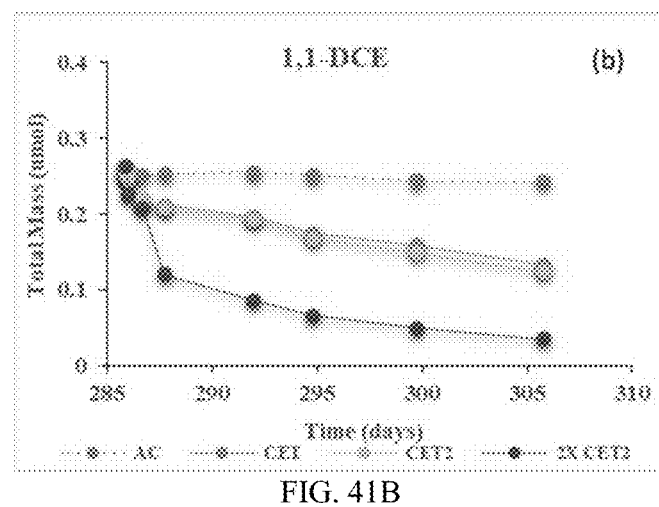

After completion of VC transformation in the reactors, 1,1-DCE was added to further examine the cometabolic activity. A low mass of 1,1-DCE (0.25 µmol) was added to each reactor on day 286. 1,1-DCE transformation was slower than VC in both TBOS and T2BOS reactors, but 2×T2BOS reactor, which has as twice mass of beads compared to TBOS and T2BOS reactors, transformed ~85% within 19 days (FIG. 41B). The results demonstrate slow rates of 1,1-DCE transformation after 285 days of bead incubation. The results show a broad range of contaminants that can be transformed by the beads co-encapsulated with 21198 and TBOS or T2BOS.

1,4-D Transformation to Low Concentrations in the CET and CET2 Reactors

Figure 42:
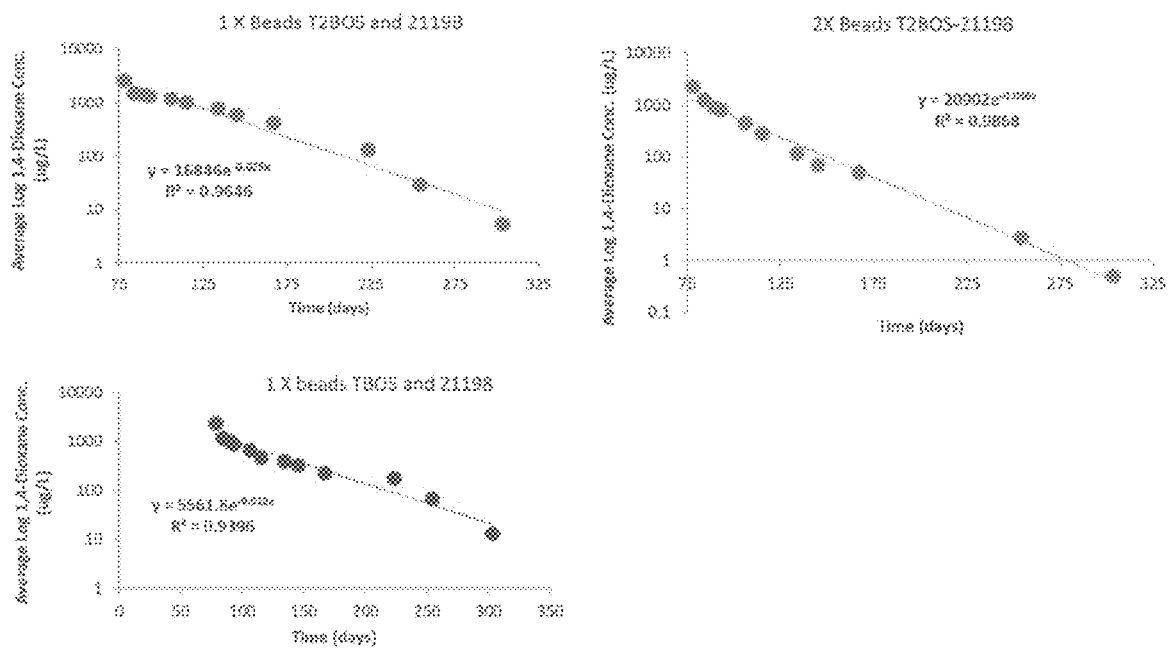
FIG. 42 presents information concerning long-term first-order transformation of the last addition of 1,4-dioxane to the TBOS/21198 and T2BOS/21198 batch reactors (IX beads). The 2× bead results are for a batch reactor that has 2 times the amount of beads as the 1× reactors.

As previously shown, four to five additions of the chosen CoC mixture (1,1,1-TCA; cis-DCE; 1,4-D), were made to CET, CET2 reactors over a period of ~264 days, and the concentrations of contaminants were monitored. We continued monitoring 1,4-D concentrations to ppb levels using a heated purge-and-trap with GC/MS detection. We achieved a low level 1,4-D concentration measurement by manually injecting 1 mL of the sample from each reactor straight into the purge-and-trap sparging vessel to decrease the instrument detection limit. This method helped decrease the 1,4-D the detection limit by not diluting the reactor sample, eliminating 1,4-D background associated with the DI water used to dilute samples. FIG. 42(A-C) show 1,4-D concentration data in the CET and $CET_2$ reactors during 70-303 days of incubation on a log-scale.

FIG. 42 (lower left) shows the log plot of 1,4-D concentrations versus time by beads co-encapsulated with TBOS and 21198 (CET) that fits a first-order rate. By day 303, 1,4-D concentrations were reduced to 13.3 µg/L (ppb) representing an over 2-order of magnitude decrease in concentration. Similar results were observed with the beads co-encapsulated with T2BOS (FIG. 42—upper left). The 1,4-D concentration was reduced to 5.5 ppb, with a slightly higher first-order rate constant compared to TBOS. When the amount of beads containing T2BOS was increased by a factor of 2, 1,4-D transformation rate increased by a factor of 1.4 and the 1,4-D concentration was reduced to 0.5 ppb (FIG. 42—upper left). Overall 1,4-D cometabolic transformation fit a first-order rate model and reduced 1,4-D concentration to 0.5 ppb. These results demonstrate how the technology can be used to treat emerging contaminants to very low concentrations. It also illustrates that how contaminants of interest can be treated at low concentrations. This is of importance for the treatment of disinfection by products and contaminants of emerging concern in drinking water, wastewater and industrial wastewater, which the technology ca be applied.

Based on these examples, gellan gum is more durable and resistant to break-down than alginate and results gathered indicate that gellan gum will be a more successful encapsulation matrix upon application of the developed technology. Also, creation of gellan gum micro-beads ~10-100 m in diameter provide positive evidence that this technology can be scaled down.

Cells co-encapsulated with TBOS were observed to transform each contaminant in a mixture of 1,1,1-TCA, cis-DCE, and 1,4-D at rates similar to initially augmented biomass for as long as ~300 days; whereas, suspended cells cometabolic transformation potential was drastically reduced by ~12 days.

Cells co-encapsulated with $T_2BOS$ were observed to transform each contaminant in a mixture of 1,1,1-TCA, cis-DCE, and 1,4-D at appreciable rates for as long as ~260 days. Transformation rates observed in cells co-encapsulated with $T_2BOS$ were lower than cells co-encapsulated with TBOS, however, rates of metabolism were also much lower.

Although contaminant transformation rates were observed to be higher in reactors containing ATCC 21198 co-encapsulated with TBOS than $T_2BOS$, the amount of $O_2$ utilized over a 260 day period within TBOS reactors was ~35 times greater than in $T_2BOS$ reactors. This illustrates the tradeoff between transformation rate and oxygen utilization efficiency. These data suggest that the co-encapsulated system containing a SRC that produces a known inducing substrate at a very slow rate may be much more efficient at treating CoCs.

The structure of the orthosilicate used as the SRC is an important design variable for remediation purposes. Structures that hydrolyze to form 1-linear alcohols hydrolyze faster that those that form branched alcohols. Shorted chained structures also hydrolyze more rapidly than longer chained structures.

Rates of cometabolism tracked rates of metabolism and hydrolysis of the SRCs. This was observed in both the incubations with direct exposure to the SRCs and the encapsulated systems.

The rates of TBOS and $T_2BOS$ hydrolysis decreased by a factor to 10 in the encapsulated beads compared to hydrolysis observed in solution when similar masses were present.

Example 21

This example concerns COC cometabolism by *Burkholderia vietnamiensis* G4 (G4). TCE cometabolism can also be achieved when G4 is grown on benzyl alcohol, the ester benzyl butyrate that hydrolyzes to form benzyl alcohol and butyrate, benzyl acetate that hydrolyzes to from benzyl alcohol and acetate. Resting kinetic tests were done to directly compare the induction of T2MO in toluene grown G4 and the ability to transform TCE.

Figure 43:
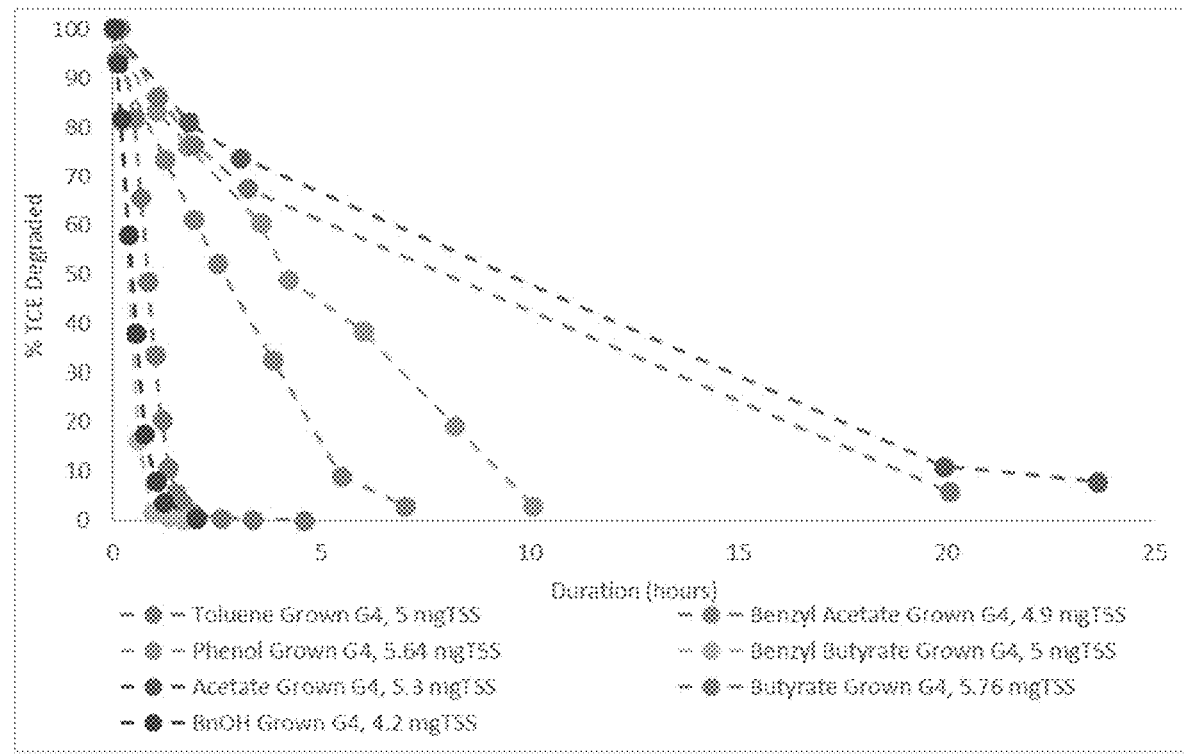
FIG. 43 provides results of resting cell transformation tests establishing that TCE is rapidly cometabolized when G4 was grown on toluene, benzyl alcohol (BnOH), and benzyl butyrate, with slower transformation rates obtained with benzyl acetate and phenol grown cells.

Results of resting cell transformation tests are shown in FIG. 43. TCE is shown to be rapidly cometabolized when G4 was grown on toluene, benzyl alcohol (BnOH), and benzyl butyrate, with slower transformation rates obtained with benzyl acetate and phenol grown cells. Slow rates of TCE transformation were obtained with cells grown on acetate and butyrate. The results show that several compounds that can be generated with SRCs, including benzyl alcohol and phenol that have potential to drive the cometabolism of TCE by G4.

Figure 44:
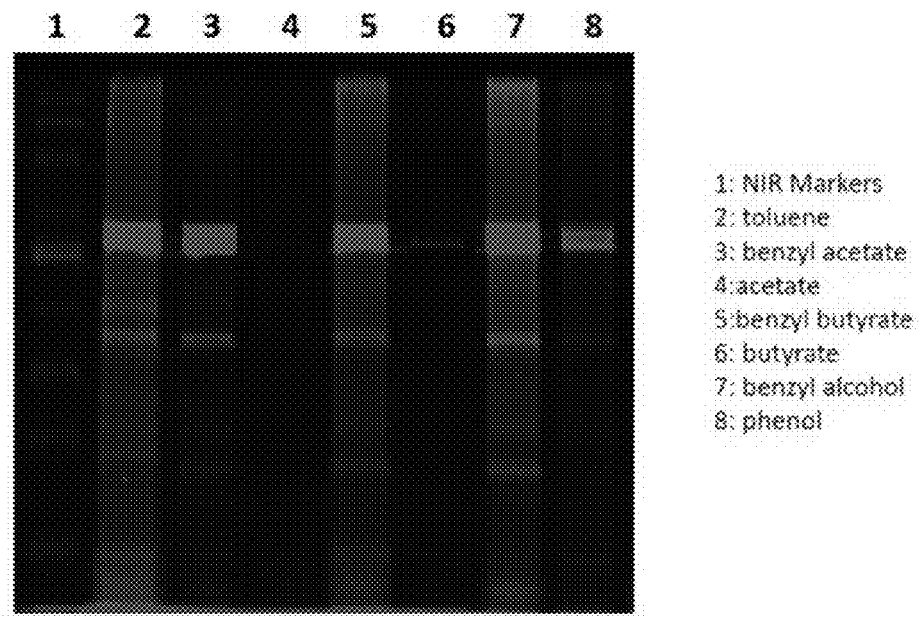
FIG. 44 are protein labeling patterns of the T4MO of G4.

Shown in FIG. 44 are the protein labeling patterns of the T2MO of G4. The results of the labeling are consistent with the TCE transformation results presented in FIG. 43. Cells grown on substrates that show bright banding also show high rates of TCE transformation. Cells grown on substrates with faint banding, including acetate and butyrate, showed much slower rates of TCE transformation.

Figure 45:
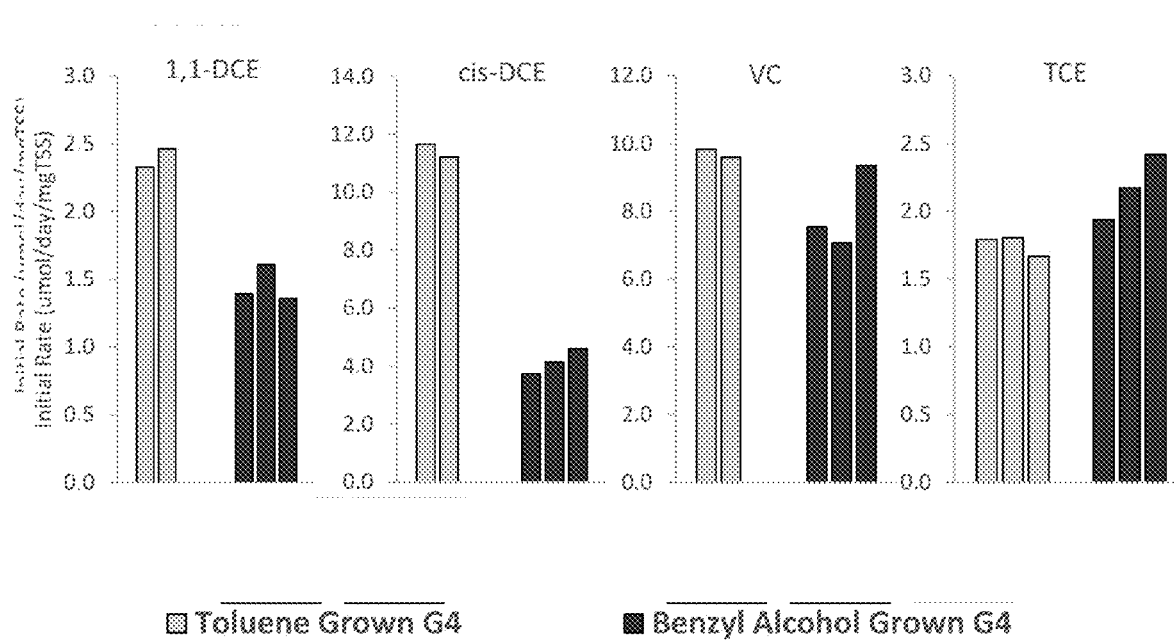
FIG. 45 provides rates of chlorinated cometabolism by G4 cells grown on toluene and benzyl alcohol.

Shown in FIG. 45 are the rates of chlorinated cometabolism by G4 cells grown on toluene and benzyl alcohol. Benzyl alcohol grown cells were able to cometabolize this broad range of chlorinated ethenes at rates similar to toluene grown cells. The results illustrate the potential of SRCs that produce benzyl alcohol, when co-encapsulated with KR1, or other toluene mono-oxygenase expressing to transformation a broad range of chlorinated ethenes and other compounds previously reported to the cometabolized by TMO producing microorganisms. Benzyl alcohol can be produced, for example, by esters, such as benzyl butyrate, or an organosilicate, like TBOS, that upon hydrolysis produces, benzyl alcohol.

The orthosilicate, tetraphenyl-orthosilicate (TPhOS), is commercially available that upon hydrolysis produces phenol. Since TCE cometabolism and T2MO was expressed when G4 was grown on phenol (FIGS. 43 and 44) the co-encapsulation of G4 with TPhOS was performed. GG beads were fabricated which contained 1.85% TPhOS by weight. The process for the encapsulation of TPhOS was like that described above, however since TPhOS is a solid at room temperature (melting point ~50° C.) at slightly different method was used to encapsulate TPhOS. TPhOS was added to the gellan-gum during the pre-gel solution heating stage when the temperature was around ~60 to 80° C. The TPhOS melted and became dispersed in the pre-gel solution. The step outline previously to make the beads remained the same.

Figure 46:
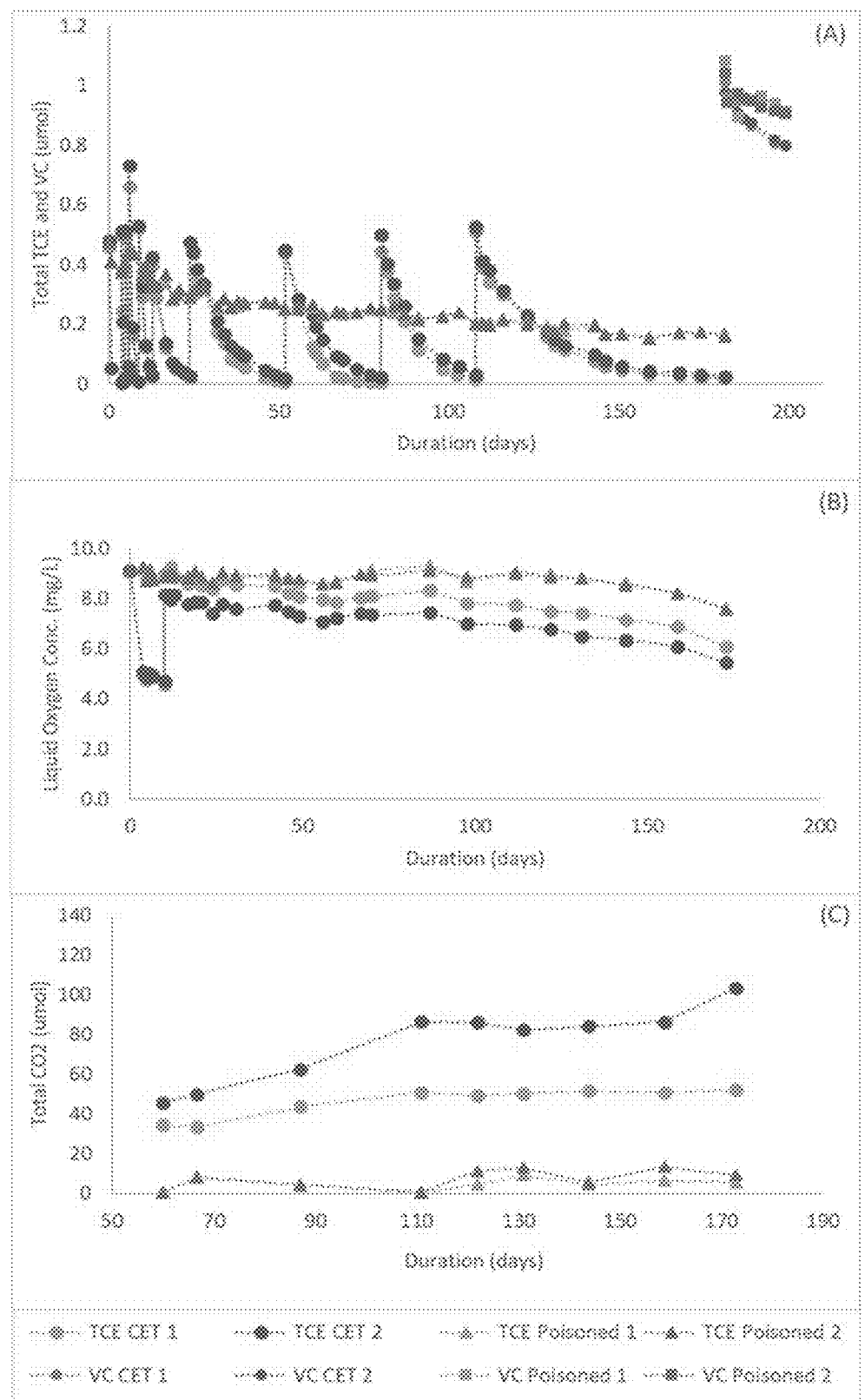
FIG. 46 provides information concerning cometabolic transformation of TCE, oxygen utilization, and $CO_2$ production rates.

The set-up for the batch experiments with G4 co-encapsulated with TPhOS included two coencapsulated treatments and two coencapsulated bottles poisoned with sodium azide (0.2% w/w) with 2 g beads per reactor. The gellan gum beads were coencapsulated at a biomass loading of 1.45 $mg_{TSS}/g_{bead}$ and 1.85% (w/w) TPhOS. TCE was added at concentrations of ~400 ppb. Results of this experiment can be seen in FIG. 46, showing cometabolic transformation of TCE, oxygen utilization, and $CO_2$ production rates. Oxygen utilization (FIG. 46B) has been low at an average rate of 0.65 umol $O_2$/day. For comparison, the oxygen utilization rates in the co-encapsulated 21198 and T2BOS reactors was an average of 0.55 umol $O_2$/day. S low rates of CO2 production (FIG. 47C) support the slow rates of $O_2$ utilization. FIG. 46A shows continuous transformation of TCE over 180 days. TCE appears to have reached steady state the past four additions of TCE at a first-order rate of approximately 0.12 $day^{-1}$. These rates are comparable to those achieved with the long-term treatment of 1,4-dioxane by 21198 encapsulated with TBOS and T2BOS (FIG. 42). The attainment of steady-state rates indicates that the phenol released by TPhOS is likely sustaining a constant biomass of KR1 in the beads. No visible growth in suspension is seen in the active treatments compared to the poisoned controls. Higher rates of VC and cis-DCE transformation would be expected, based on the results of kinetic studies shown in FIG. 45.

Example 22

This example demonstrates that prolonged cometabolic transformation of TCE can be achieved upon mixing of co-encapsulated cells with aquifer solids and groundwater, microcosms were constructed with aquifer solids that appeared to be fine-grained clay silts from Fort Carson, CO a site with 1,4-dioxane and TCE contamination. Artificial groundwater was made to replicate groundwater chemistry at the site. The aquifer solids and artificial groundwater were combined to yield a concentration of 52 g aquifer solids/L groundwater and mixed as a slurry before distributing 55 mL into each microcosm. The set-up includes an abiotic control, a control with co-encapsulated beads and propyne (2% v/v in the headspace) as a monooxygenase inhibitor, and triplicates of active co-encapsulated treatments. Toluene grown G4 was co-encapsulated at a mass of 0.85 mg TSS/g bead with 2% (w/w) TPhOS. All treatments, except the abiotic control, had 2 g beads added for a total biomass of 1.7 mg TSS per microcosm. TCE concentrations in the solids were low; therefore, TCE was added to bring the aqueous concentrations to ~660 ppb.

Figure 47:
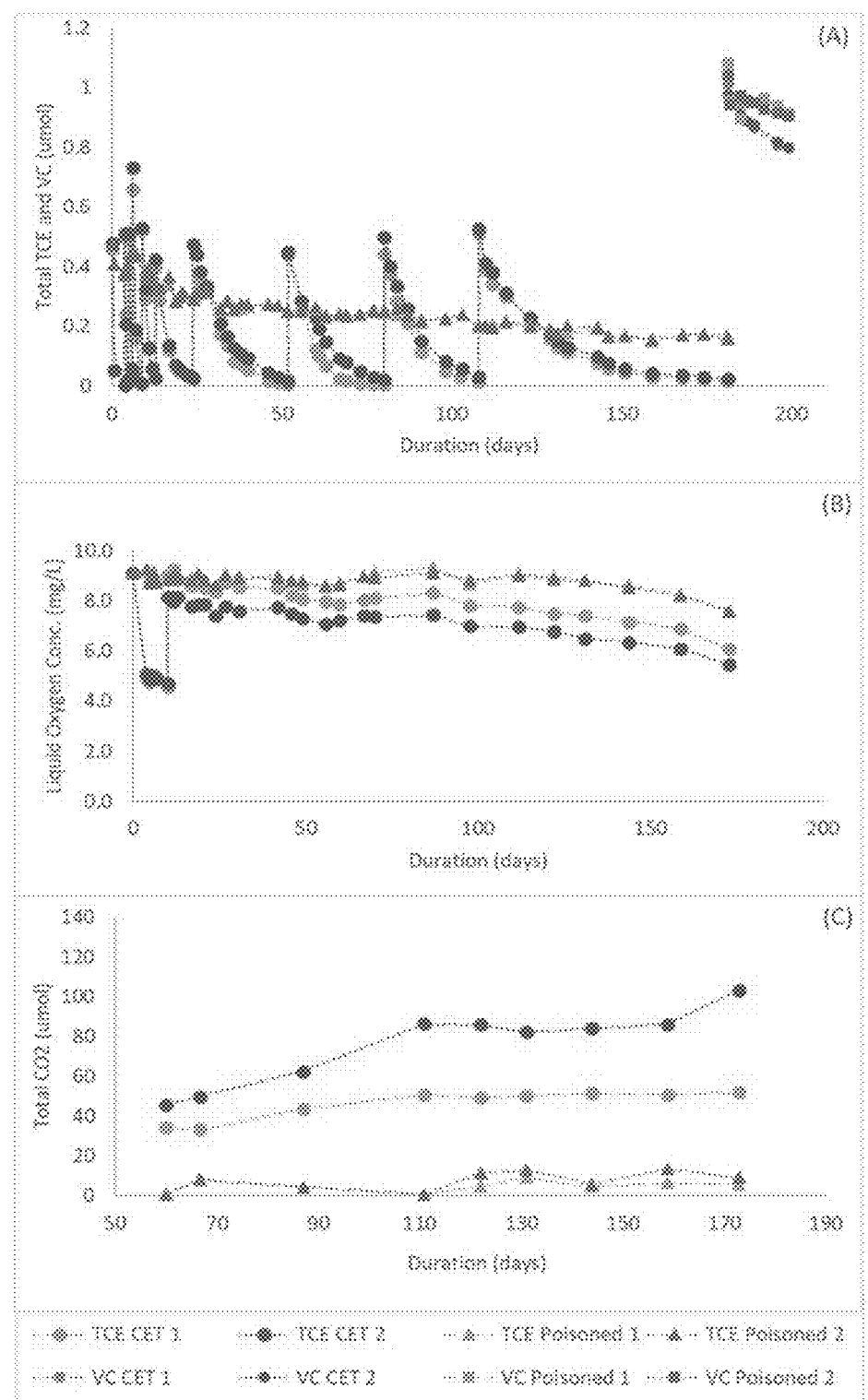
FIG. 47 provides information concerning cometabolic transformation of (A) cis-DCE, (B) TCE, (C) $O_2$ production, and (D) $CO_2$ production in Fort Carson microcosms. (CET)—Coencapsulated treatments with G4 and 1.85% (w/w) TPhOS.

As can be seen in FIG. 47B, the initial TCE was completely transformed in 2.5 days. TCE transformation then slowed considerably. On day 6, cis-DCE was added to all treatments at a liquid concentration of ~600 ppb to verify cometabolic activity, given that it has a higher rate of transformation by G4. FIG. 48A shows complete transformation of the initial cis-DCE addition occurred over the course of 30 days.

The rates of TCE slowed in the microcosm as compared to the pure media experiment (FIG. 47A), which may partly be due to nutrient limitations. On day 45, a concentrated phosphate buffer (1 mL of 2 M) was amended to all bottles, and the rates of cis-DCE transformation increased and continued transformation of a third addition of TCE was observed. Transformation rates stalled again around 120 days, at which point an IC analysis showed complete depletion of nitrate and phosphate.

Example 23

This example concerns treating groundwater using continuous flow conditions, the technology can be used to from permeable reactive barrier for subsurface remediation or for the treatment of wastewater and industrial wastewater using column reactors. Examples are provided for columns packed with gellan-gum beads co-encapsulated with 21198 and TBOS and 21198 and T2BOS. Based on batch experimental results with T2BOS, the hydrolysis rate is about 30 times slower than TBOS and therefore, can promote longer-term treatment with less oxygen consumption.

Columns #1 and #2 were packed with gellan-gum beads co-encapsulated with 21198 and TBOS. Over 150 pore volumes (PV) groundwater contaminated with a mixture of cis-DCE, 1,1,1-TCA and 1,4-dioxane, each at 250 μg/L, were treated over a period of approximately 135 days. The columns dimensions and operating conditions are provide in Table 23.

TABLE 23

Column #1 and #2 operation conditions as well as estimated parameters based on the bromide tracer tests

| | Column #1 | Column#2 | Unit |
|---|---|---|---|
| Dispersion Coefficient | 0.10 | 0.10 | cm^2/hr |
| Column Length | 15.9 | 14.1 | cm |
| Flow Rate | 1.0 | 1.0 | mL/hr |
| Flow Rate | 24 | 24 | mL/day |
| Cross Sectional Area | 4.91 | 4.91 | cm^2 |
| Superficial Velocity | 4.89 | 4.89 | cm/day |
| Avg. Linear Velocity | 0.28 | 0.31 | cm/hr |
| Volume | 78 | 69.18 | mL |
| Residence Time | 56 | 46 | hr |
| Empty Bed Contact Time | 78 | 69.18 | hr |
| Porosity | 0.72 | 0.67 | |

Figure 48:
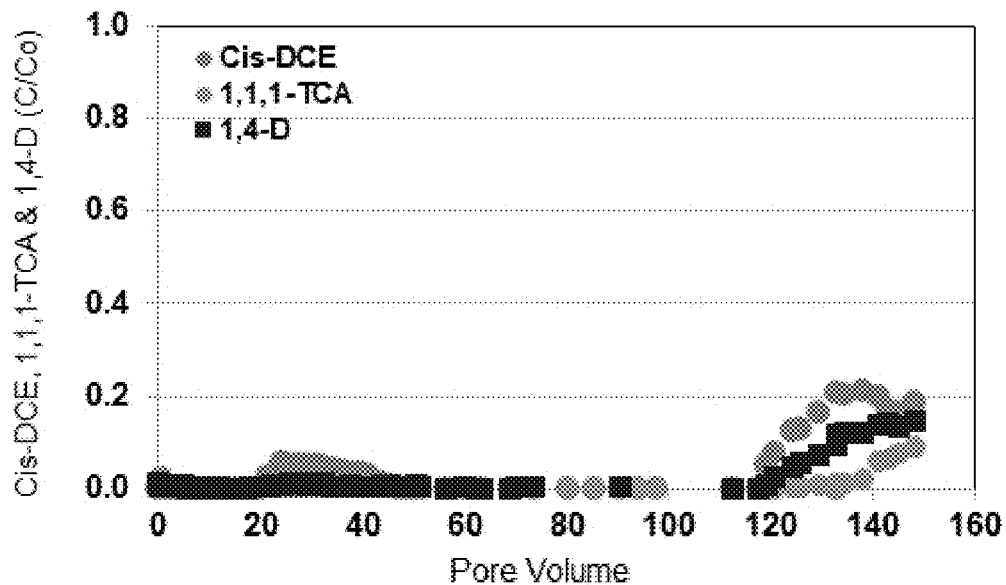
FIG. 48 provides effluent cis-DCE, 1,1,1-TCA, and 1,4-Dioxane concentration histories normalized to the influent concentration (C/Co) for Column #1 packed with gellan-gum beads co-encapsulated with 10% TBOS and ATCC 21198.
Figure 49:
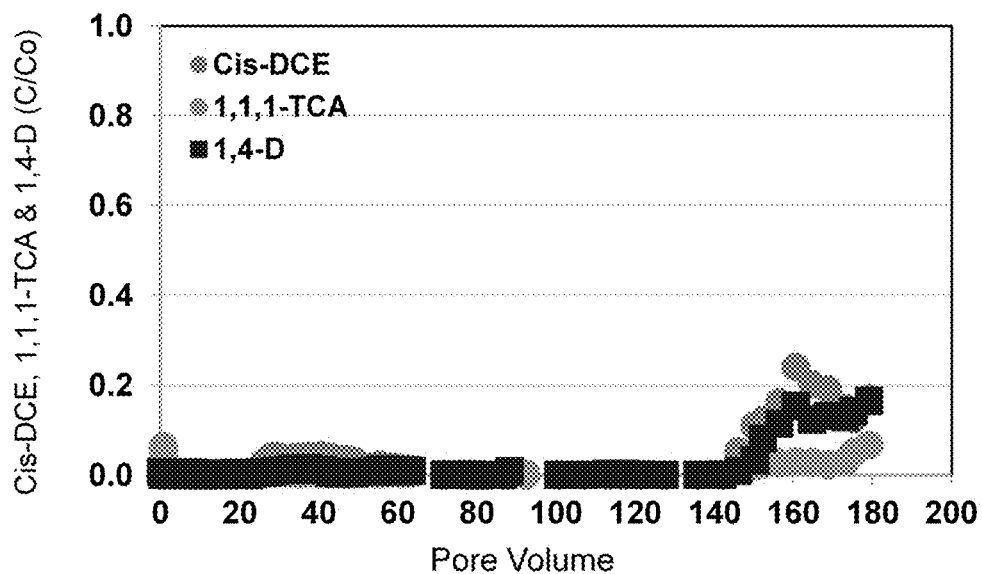
FIG. 49 provides effluent cis-DCE, 1,1,1-TCA, and 1,4-Dioxane concentration histories normalized to the influent concentration (C/Co) for Column #2 packed with gellan-gum beads co-encapsulated with 10% TBOS and ATCC 21198.
Figure 50:
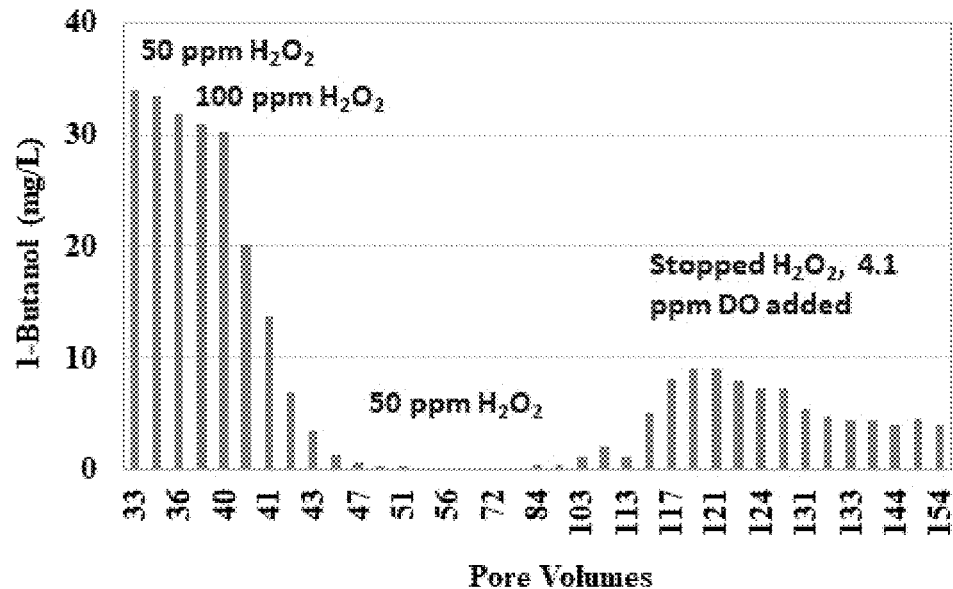
FIG. 50 provides 1-Butanol effluent concentration histories in Column #1 during the addition of different $H_2O_2$ and DO concentrations.
Figure 51:
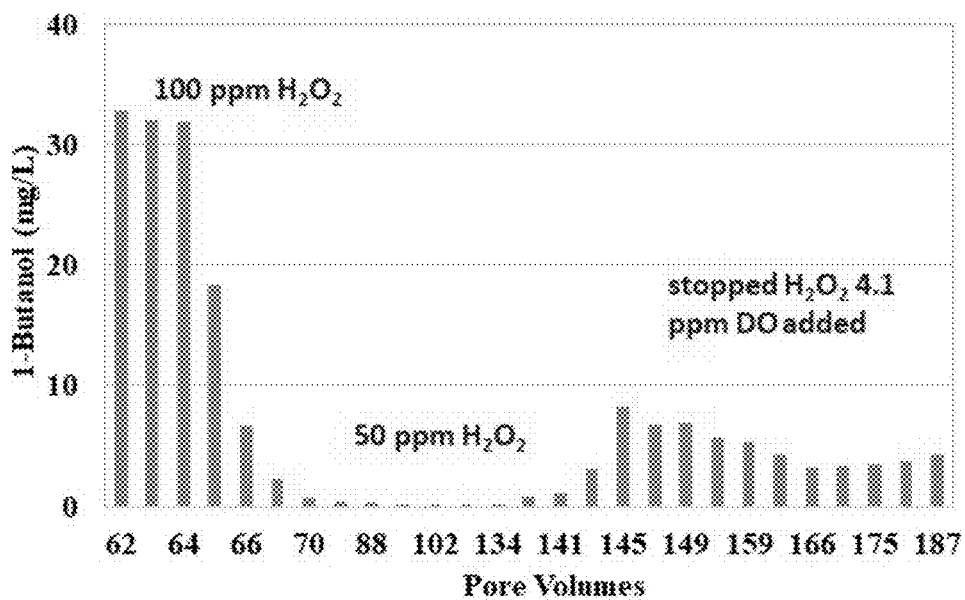
FIG. 51 provides 1-Butanol effluent concentration histories in Column #2 during the addition of different $H_2O_2$ and DO concentrations.

The transformation results are presented in FIGS. 48 and 49. Early on in the study, the effluent dissolved oxygen (DO) concentrations were reduced to ~0 mg/L, creating anaerobic conditions at the top of the columns. During this period the DO influent concentration was 12 mg/l. 1-butanol concentrations in the column effluent, resulting from TBOS hydrolysis in the anaerobic zone, as high as 35 mg/L, were observed (FIGS. 50 and 51). The addition of hydrogen peroxide ($H_2O_2$) as an additional DO source was started after 33 pore volumes (PV) of flow in Column #1 and 62 PV in Column #2. This resulted in a gradual decrease 1-butanol in the column effluent, with concentrations decreasing to below detection in Column #1 and Column #2 by 56 and 106 PV, respectively.

An increase in the extent of cometabolic transformation resulting from the biostimulation of the beads throughout the columns is shown in FIGS. 48 and 49. Plotted on the y-axis is the column effluent concentration normalized to the influent concentration (C/Co). Greater than 99% removal of cis-DCE, 1,1,1-TCA, and 1,4-dioxane was achieved at flow-rates of 1 and 2 mL/hr, representing hydraulic residence times of approximately 2 and 1 days, respectively. At about 60 PV (Column #1) and 100 PV (Column #2) the flow was increased to 4 mL/hr, resulting in a hydraulic residence of about 0.5 day. Very high extends of COCs transformation (>99%) and 1-butanol utilization were maintained.

At 100 PV in Column #1 and 134 PV in Column #2 the influent DO concentration was reduced to 4.2 mg/L by stopping $H_2O_2$ addition. In response to this change, the 1-butanol increased from below detection to about 10 mg/L, which is about 30% of the concentration observed prior to the addition of $H_2O_2$ at 33 and 62 PV, in Column #1 and Column #2, respectively (FIGS. 50 and 51). These effluent 1-butanol concentrations likely represent the steady-state rate of hydrolysis in the column with long-term operation. The effluents concentrations of cis-DCE, 1,1,1-TCA and 1,4-dioxane increased upon reducing DO, illustrating oxygen utilization is required for cometabolism to occur (FIGS. 48 and 49). About 80% removal of cis-DCE, 1,1,1-TCA, and 1,4-dioxane was maintained even at these very low influent DO concentrations. Approximately 600 μg/L of COCs are being continuously transformed with the consumption of 4 mg/L of DO. This corresponds to a transformation yield of 0.15 mg COC per mg of $O_2$, which is a very high oxygen, based transformation yield for a cometabolic process, and is more in the range of that achieved in a direct aerobic metabolic process.

Column #3 is packed with gellan-gum beads co-encapsulated with ATCC 21198 and T2BOS. Cometabolic transformation of the mixture 1,1,1-TCA, cis-DCE and 1,4-

Dioxane (250 µg/L each) has been maintained for over 15 PV. Greater than 99% removal of cis-DCE, 1,1,1-TCA, and 1,4-dioxane is being achieved with a hydraulic residence time of 1 day. The DO concentration being fed the column is 14 mg/L, which was reduced to ~0 mg/L in the column effluent. These results show effective cometabolism is being achieved with gellan-gum beads co-encapsulated with T2BOS and 21198, with only the addition of oxygenated groundwater.

Figure 52:
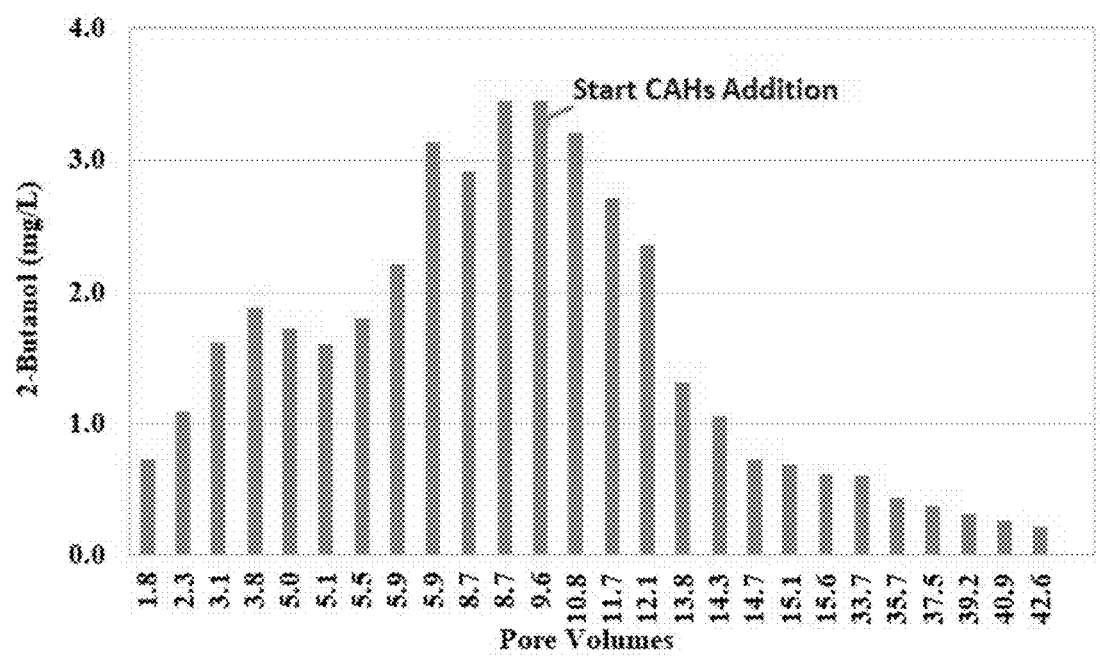
FIG. 52 provides 2-butanol concentration history in Column #3 during at flowrates of 1 mL/hr and 2 mL/hr at an influent DO concentration and 14 mg/L.

Initially, 2-butanol concentrations in the column effluent increased to a maximum of 3.5 mg/L, but then gradually decreased to around 0.2 mg/L (FIG. 52). The maximum 2-butanol concentration of 3.5 mg/L was much lower than the 35 mg/L 1-butanol concentration observed at the start of the Column #1 and Column #2 tests (FIGS. 50 and 51). This order of magnitude lower concentration is consistent with the much lower rate of T2BOS hydrolysis, compared to TBOS. The gradual decrease of 2-butanol concentration in the column indicates the increase in the biomass concentration of 21198 in the gellan-gum beads with time. Due to the slower rate of hydrolysis, the biomass is much lower in the gellan-gum beads. Column #3 showed a faint orange color after 40 PV of flow, compared to that observed in Column #1 supporting the much lower biomass in the beads this column.

Overall Columns #1, #2 and #3 data show ATCC 21198 when co-encapsulated in gellan-gum beads containing 10% TBOS or T2BOS, continuously transforms a mixture of cis-DCE, 1,1,1-TCA and 1,4-dioxane, achieving over 99% removal. These high extents of removal were achieved with very short hydraulic residence time of ~12 hours. Biostimulation of 21198 within the beads was indicate by the gradual utilization of 1-butanol and 2-butanol produced within the beads. Based on the lower oxygen consumption, T2BOS was more effective than TBOS, since $H_2O_2$ addition was not needed to achieve over 99% removal of the COC mixture. The gellan-gum beads have remained physically stable for over 150 PVs and over 135 days. No loss in the columns' permeability was observed. The continuous cometabolic treatment to very low concentrations demonstrate the potential of creating permeable reactive barriers with the beads for in-situ treatment of COC mixtures. The results also demonstrate that the co-encapsulated bead columns could be used to treat disinfection by-products and emerging contaminants of concern in domestic wastewater, drinking water and for industrial wastewater treatment.

Example 24

This example provides proof that co-metabolizing cultures could be induced by or gain energy from products of co-encapsulated SRCs. ATCC 21198 was encapsulated in alginate macro-beads. Two batches of alginate macro-beads were created; one containing ATCC 21198 at a biomass loading of ~0.5 $mg_{TSS}/g_{bead}$ alone and one containing ATCC 21198 co-encapsulated with TBOS at biomass loading of ~0.5 $mg_{TSS}/g_{bead}$ and TBOS mass loading of ~5% (w/w).

Four grams of beads were added to separate reactors to reach a final cell concentration of ~10 $mg_{TSS}/L$ and when applicable TBOS concentration of ~1000 mg/L. Abiotic controls were used to ensure contaminant transformation was due to the addition of ATCC 21198, and in this experiment 4 grams of alginate beads, that were created without an addition of ATCC 21198, were added to abiotic controls to ensure the creation of beads was sterile and free from contamination. Reactors were spiked with the chosen CoC mixture; 1,1,1-TCA (~250 ppb), cDCE (~250 ppb), and 1,4-D (~500 ppb); and were monitored over a period of ~200 days for respiration data (O2/CO2), substrate data (SRC/alcohols), and contaminant data (1,1,1-TC A, cDCE, and 1,4-D).

A summary of the treatments examined within this experiment are presented in Table 24.

TABLE 24

Proof of Concept #1 reactor treatment summary.

| | | | Reactor Contents | | | |
|---|---|---|---|---|---|---|
| Treatment Name | Abbreviations | Number of Reactors | Beads (4 g) | Cells (2 $mg_{TSS}$) | TBOS (624 µmol) | CoCs |
| Abiotic Control | AC | 3 | ✓ | — | — | ✓ |
| Encapsulated Cell Remediation Control | EC | 3 | ✓ | ✓ | — | ✓ |
| Co-encapsulated Cell Substrate Control | CECS | 3 | ✓ | ✓ | ✓ | — |
| Co-encapsulated Cell Remediation | CECR | 3 | ✓ | ✓ | ✓ | ✓ |

Encapsulated cell remediation controls (EC) were created in order to determine if utilization of substrates produced by co-encapsulated TBOS in the co-encapsulated remediation reactors (CECR) increased cells remediation potential in relation to cells encapsulated alone. Co-encapsulated substrate control reactors (CECS) were created such that substrate utilization could still be observed if the mass of contaminants added were to inhibit encapsulated cultures.

Contaminant Transformation Observations

All reactors received only a single addition of contaminants due to minimal contaminant transformation over the duration of this experiment (FIG. 35C-E) The stark contrast between the cometabolism data presented in FIG. 35 and data presented in section 4.3 for alginate-encapsulated cultures is likely due to the flawed encapsulation method used within this study having caused cell death prior to reactor creation. However, it is possible that to a lesser degree, that cells grown up under slightly different growth conditions may exhibit higher transformation durations and/or capacities due to the level of energy stored during growth.[115]

Figure 53:
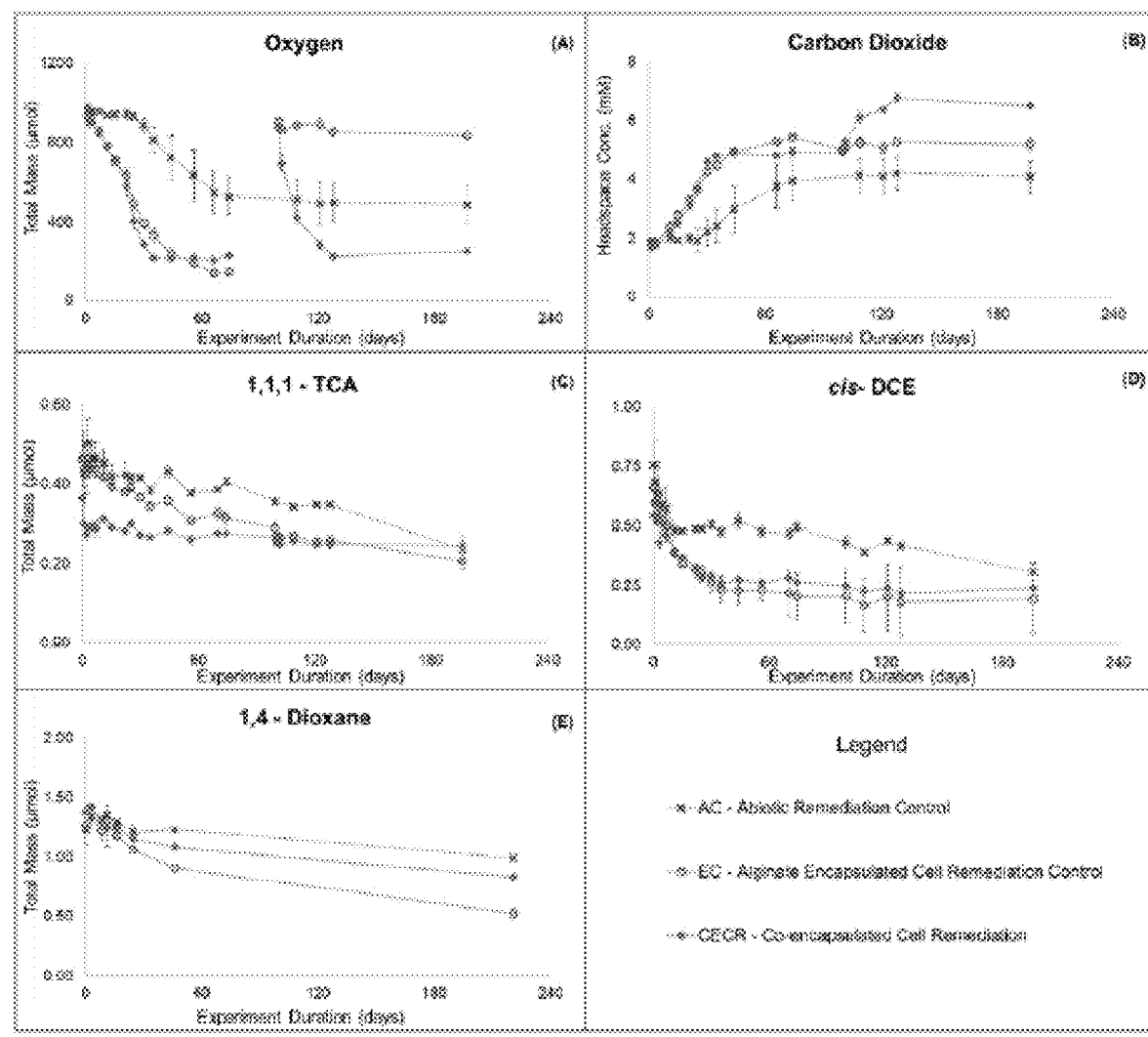
FIG. 53 provides information concerning long-term alginate encapsulated and co-encapsulated cell cometabolic transformation study.

FIG. 53 provides data concerning long-term alginate encapsulated and co-encapsulated cell cometabolic transformation study (A-B) Respiration data $O_2$ measurements reported as ~180 mol is assumed to be near zero due to vacuum created within reactors. $CO_2$ data are presented in terms of measured headspace concentrations due to speciation of $CO_2$ in carbonate system in the aqueous phase and lack of pH measurements throughout experiment. (C-E)

Contamination transformation on data. A single contaminant addition was made to each reactor. Data points are averages between triplicate reactors in each treatment and errors bars are 95%, confidence intervals.

Examining contaminant transformation data from the initial contaminant masses present in bottles to the final data point taken at ~200 days, suggests that there is not a significant difference, as determined by overlapping 95% confidence intervals, between cometabolically active treatments (EC/CECR) and the abiotic control, other than 1,4-dioxane. However, the majority of transformation observed in active treatments occurred over the first 60 days whereas, disappearance of contaminants within the abiotic controls happened after ~120 days (FIG. 53). This suggests that low amounts ATCC 21198 were active upon addition to reactors, though the lack of transformation after 60 days suggests that cometabolizing cultures are no longer active or induced. Initial inactivation occurred during the encapsulation process and transformation likely halted due to transformation capacities of impaired cells being met and decay of cometabolic enzymes over the long-term experiment. The limited contaminant transformation observed in this experiment highlights the importance of the work conducted to optimize encapsulation methods, presented in section 4.2, such that cells maintain viability post-encapsulation and the reduction in remediation potential observed here is mitigated.

Cellular Respiration and SRS Observations

The above contaminant transformation data provide little to no evidence of growth or induction of ATCC 21198 by slowly releasing substrates. However, respiration and substrate data provide evidence that an aerobic microbe within these reactors was utilizing Or and producing $CO_2$, and therefore, consuming substrates (FIG. 53). FIG. 36 presents the same respiration data as FIG. 53, though respiration time-series data for co-encapsulated cell reactors that did not received an addition of contaminants is included. Also, identifiers for the addition of Or is included.

Figure 54:
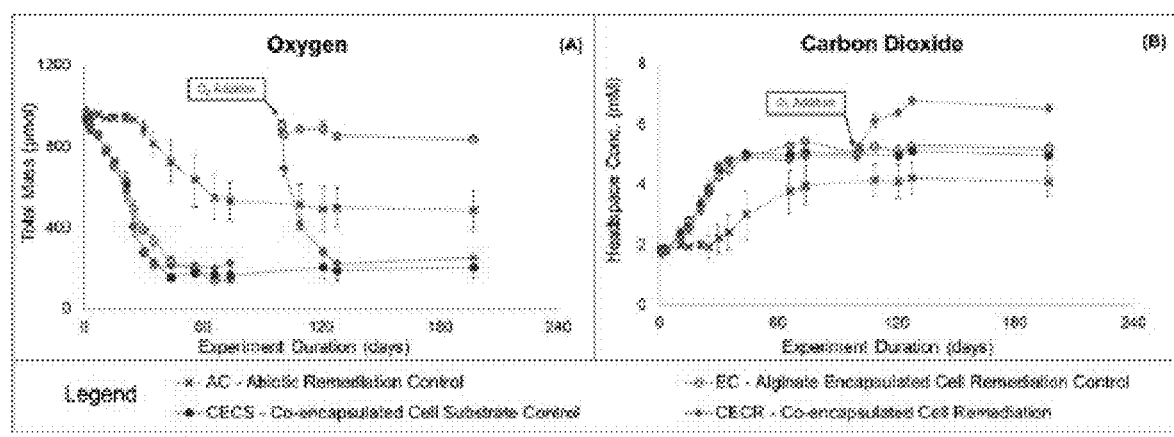
FIG. 54 provides information concerning a long-term alginate encapsulated and co-encapsulated cell cometabolic transformation study.

FIG. 54 provides information concerning a long-term alginate encapsulated and co-encapsulated cell cometabolic transformation study. (A-B) Respiration data. $O_2$ measurements reported as ~180 μmol is assumed to be near zero due to vacuum created within reactors. $CO_2$ data are presented in terms of measured headspace concentrations due to speciation of $CO_2$ in carbonate system in the aqueous phase and lack of pH measurements throughout experiment. $O_2$ was refreshed at ~100 days in EC and CECR reactors. AC. EC, and CECR reactors contain CoC mixture, data presented in FIG. 52. Data points are averages between triplicate reactors in each treatment and errors bars are 95% confidence intervals.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A composition for remediating 1,4-dioxane, 1,1,1-trichloroethane (1,1,1-TCA) and/or dichloroethene (DCE), comprising:
   microbial cells obtained from *Rhodococcus rhodochrous* ATCC 21198;
   at least one orthosilicate co-metabolism substrate selected from tetrabutyl orthosilicate (TBOS), tetra-sec-butyl orthosilicate (T2BOS), and combinations thereof, to induce selected enzyme production by the microbial cells; and
   a bead having at least one dimension of at least 1 millimeter or greater encapsulating the microbial cells and the at least one co-metabolism substrate.

2. A method for remediating 1,4-dioxane, 1,1,1-TCA and/or DCE, comprising:
   providing a composition according to claim 1; and
   contacting 1,4-dioxane, 1,1,1-TCA and/or DCE with the composition.

* * * * *